US006465430B1

(12) United States Patent
Dower et al.

(10) Patent No.: US 6,465,430 B1
(45) Date of Patent: *Oct. 15, 2002

(54) PEPTIDES AND COMPOUNDS THAT BIND TO A THROMBOPOIETIN RECEPTOR

(75) Inventors: William J. Dower, Menlo Park; Ronald W. Barrett, Saratoga; Steven E. Cwirla, Menlo Park; David J. Duffin, East Palo Alto; Christian M. Gates, Morgan Hill; Sherril S. Haselden, Santa Cruz; Larry C. Mattheakis, Cupertino; Peter J. Schatz, Mountain View; Christopher R. Wagstrom, Los Altos; Nicholas C. Wrighton, Palo Alto, all of CA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/549,090

(22) Filed: Apr. 13, 2000

Related U.S. Application Data

(63) Continuation of application No. 08/973,225, filed as application No. PCT/US96/09623 on Jun. 7, 1996, now Pat. No. 6,083,913, which is a continuation of application No. 08/485,301, filed on Jun. 7, 1995, now abandoned, which is a continuation of application No. 08/478,128, filed on Jun. 7, 1995, now abandoned.

(51) Int. Cl.$^7$ .................... A61K 38/00; A61K 39/00; C07K 5/00; C07K 7/00
(52) U.S. Cl. .................... 514/13; 514/14; 514/15; 424/185.1
(58) Field of Search ................ 514/13, 14, 15; 424/185.1

(56) References Cited

U.S. PATENT DOCUMENTS

| 5,141,851 A | | 8/1992 | Brown et al. |
|---|---|---|---|
| 5,143,854 A | | 9/1992 | Pirrung et al. |
| 5,270,170 A | | 12/1993 | Schatz et al. |
| 5,326,558 A | | 7/1994 | Turner et al. |
| 5,338,665 A | | 8/1994 | Schatz et al. |
| 5,358,934 A | | 10/1994 | Borovsky et al. |
| 5,384,331 A | | 1/1995 | Kogan et al. |
| 5,411,942 A | | 5/1995 | Widmer et al. |
| 5,869,451 A | * | 2/1999 | Dower et al. .................. 514/13 |
| 5,932,546 A | | 8/1999 | Barrett et al. |
| 6,083,913 A | * | 7/2000 | Dower et al. .................. 514/13 |

FOREIGN PATENT DOCUMENTS

| EP | 0 690 127 A1 | 1/1995 |
|---|---|---|
| EP | 0 668 352 A1 | 2/1995 |
| EP | 0 675 201 A1 | 3/1995 |
| GB | 2 285 446 A | 7/1995 |
| WO | WO 90/15070 | 12/1990 |
| WO | WO 91/07988 | 6/1991 |
| WO | WO 91/08752 | 6/1991 |
| WO | WO 93/25221 | 12/1993 |
| WO | WO 95/11922 | 5/1995 |
| WO | WO 95/18858 | 7/1995 |
| WO | WO 95/21626 | 8/1995 |
| WO | WO 95/21919 | 8/1995 |
| WO | WO 95/21920 | 8/1995 |
| WO | WO 95/28907 | 11/1995 |
| WO | WO 96/17062 A1 | 6/1996 |
| WO | WO 96/17062 | 6/1996 |
| WO | WO 96/17067 | 6/1996 |

OTHER PUBLICATIONS

Caras et al., "Signal peptide for protein secretion directing glycophospholipid membrane anchor attachment", Science, vol. 243:1196–1198 (1989).
Cwirla et al., "Peptides on phage: A vast library of peptides for identifying ligands", Proc. Natl. Acad. Sci. USA, vol. 87:6378–6382 (1990).
Dower et al., The search for molecular diversity (II): Recombinant and synthetic randomized peptide libraries:, Ann. Rep. Med. Chem., vol. 26:271–280 (1991).
Dower et al., "High efficiency transformation of E.coli by high voltage electroporation", Nucleic Acids Research, vol. 16:6127 (1988).
Fodor et al., "Light–directed, spatially addressable parallel chemical synthesis", Science, vol. 251:767–773 (1991).
Harker, "Kinetics of thrombopoiesis", J. Clin. Invest., vol. 47:458–465 (1968).
Kaushansky et al., "Promotion of megakaryocyte progenitor expansion and differentiation by the c–Mpl ligand thrombopoietin", Nature, vol. 369:568–571 (1994).
Kojima et al., Molecular cloning and expression of megakaryocyte potentiating factor cDNA, J. Biol. Chem., vol. 270:21984–21990 (1995).
Kuter et al., "The purification of megapoietin: A physiological regulator of megakaryocyte growth and platelet production", Proc. Natl. Acad. Sci. USA, vol. 91:11104–11108 (1994).
McDonald, "Thrombopoietin—Its biology, clinical aspects and possibilites", Am. J. Pediatric Hematology/Oncology, vol. 14:8–21 (1992).
Metcalf, "Thrombopoietin—at last", Nature, vol. 369:519–520 (1994).
Methia et al., "Oligodeoxynucleotides antisense to the proto–oncogene c–mpl specifically inhibit in vitro megakaryocytopoiesis", Blood, vol. 82:1395–1401 (1993).
Mossmann, "Rapid colorimetirc assays for cellular growth and survival: Application to proliferation and cytotoxicity assays", J. Immunol. Methods, vol. 65:55–63 (1983).

(List continued on next page.)

Primary Examiner—Avis M. Davenport
(74) Attorney, Agent, or Firm—Virginia C. Bennett

(57) ABSTRACT

Receptors are peptides and peptide mimetics that bind to and activate the thrombopoietin receptor. Such peptides and peptide mimetics are useful in methods for treating hematological disorders and particularly, thrombocytopenia resulting from chemotherapy, radiation therapy, or bone marrow transfusions as well as in diagnostic methods employing labeled peptides and peptide mimetics.

20 Claims, 15 Drawing Sheets

OTHER PUBLICATIONS

Or et al., Cysteine alkylation in unprotected peptides: Synthesis of a carbavasopressin analogue by intramolecular cysteine alkylation, J. Org. Chem., vol. 56:3146–3149 (1991).

de Sauvage et al., "Stimulation of megakaryoctyopoiesis and thrombopoiesis by the c–Mpl ligand", Nature, vol. 369:533–538 (1994).

Souyri et al., A putative truncated cytokine receptor gene transduced by the myeloproliferative leukemia virus immortalizes hematopoietic progenitors, Cell, vol. 63:1137–1147 (1990).

Vigon et al., "Molecular cloning and characterization of MPL, the human hormolog of the v–mpl oncogene: Identification of a member of the hematopoietic growth factor receptor superfamily", Proc. Natl. Acad. Sci. USA, vol. 89:5640–5644 (1992).

Verber et al., "The design of metabolically–stable peptide analogs", Trends in Neurosciences (TINS), pp. 392–396 (1990).

Wendling et al., "The oncogene V–MPL, A putative truncated cytokine receptor which immortalizes hematopoietic progenitors", L'Inserm, pp. 145–146 (1992).

Wendling et al., c–Mpl ligand is a humoral regulator of megakaryocytopoisis, Nature:571–574 (1994).

Kato et al., Purification and Characterization of Thrombopoietin38 , J. Biochem, vol. 118:229–236 (1995).

Wada et al., "Characterization of the Truncated Thrombopoietin Variants", Biophysical Research Communications, vol. 213:1091–1098 (1995).

Barker et al., "Cyclic RGE peptide analogues as antiplatelet antithrombotics", J. Med. Chem., vol. 35:2040–2048 (1992).

Bartley et al., "Identification and cloning of a megakaryocyte growth and development factor that is a ligand for the cytokine receptor Mpl", Cell, vol. 77:1117–1124 (1994).

Bazan, "Structural design and molecular evolution of a cytokine receptor superfamily", Proc. Natl. Acad. Sci. USA, vol. 87:6934–6938 (1990).

* cited by examiner pJS142 Library Vector, cloning sites at 3' end of lacI gene:

```
---lacI-------><-------------linker--------------->
                                       Sfi I                              Eag I
       Xho I                Stu I           Hpa I           Sfi I    Msc I          Sal I
       L  E  S  G  Q  V  V  H  G  E  Q  V  G  G  E  A  S  G  A  V  N  G  R  G  L  A  G  Q  *
       CTCGAGAGCGGGCAGgtggtgcatgggagcaggtggtggtgaggCCTCCGGGGGCCGTTAACGGCCGTGGCCAATAAgtcgac
       GAGCTCTCGCCCGTCcaccacgtaccctcgtccaccaccactcCGGAGGCCCCGGCAATTGCCGGCACCGGTTATTcagctg
```

FIG. 4B library Construction after SfiI digestion:

```
---lacI-------><-------------linker--------------><library>
                                                                                          Library Oligo
                                       BspE I                                                  ↓
       Xho I                Stu I                 G  G  G  Xₙ  *                Msc I          Sal I
       L  E  S  G  Q  V  V  H  G  E  Q  V  G  G  E  A  S                                      ON-830
       CTCGAGAGCGGGCAGgtggtgcatgggagcaggtggtggtgaggCCTCCG gagtggt(NNK)ₙtaactaagtaaagc TGGCCAATAAgtcgac
       GAGCTCTCGCCCGTCcaccacgtaccctcgtccaccaccactcCGGA ggcctccacca              attgattcatt TCGACCGGTTATTcagctg
                                                    ↑
                                                 ON-829
```

FIG. 4C pELM3/pELM15 MBP vector cloning sites:

```
---MBP--->  <-----------------linker--------------------->  <----Xa
            Sac I
  Q   T   N   S   S   N   N   N   N   N   N   N   N   L   G   I   E
 CAG ACT AAT TCG AGC TCG AAC AAC AAT AAC AAC AAC AAC CTC GGG ATC GAG
 GTC TGA TTA AGC TCG AGC TTG TTG TTA TTG TTG TTG TTG GAG CCC TAG CTC Xa--->    <--------------------cloning sites------------------------->
          Age I  Pml I    Sma I   EcoR I  BamH I   Xba I   Sal I   Pst I   Hind III
  G   R   T   G   H   V   A   R   E   F   G   S   S   R   V   D   L   Q   A   S
 GGA AGG ACC GGT CAC GTG GCC CGG GAA TTC GGA TCC TCT AGA GTC GAC CTG CAG GCA AGC TT
 CCT TCC TGG CCA GTG CAC CGG GCC CTT AAG CCT AGG AGA TCT CAG CTG GAC GTC CGT TCG AA
```

FIG. 5A pELM3/pELM15 after subcloning of library insert:

```
Xa--->   <----linker--->  <library>                                     Msc I           Sal I
  G   R   T   G   G   G   X_n        *
 GGA AGG ACC GGA GGT GGT  (NNK)_n  TAA CTA AGT AAA GCT GGC CAA TAA GTC GAC
 CCT TCC TGG CCT CCA CCA  (NNM)_n  ATT GAT TCA TTT CGA CCG GTT ATT CAG CTG
```

FIG. 5B pCMG14 Library Vector, cloning sites at 3' end of Headpiece Dimer gene:

```
------Headpiece------><----linker---->
                      Sfi I           Eag I
                    Stu I      Hpa I      Sfi I    Msc I      Sal I
   E  A  A  M  A  E  L  N  Y  I  P  R  S  Q  E  A  S  G  A  V  N  G  R  G  L  A  G  Q  *
GAAGCGGCGATGGCGGAGCTGAATTACATTCCCcggtcgcaggagGCCTCCGGGGCCGTTAACGGCCGTGGCCTAGCTGGCCAATAAgtcgac
CTTCGCCGCTACCGCCTCGACTTAATGTAAGGGccagcgtcctcCGGAGGCCCCGGCAATTGCCGGCACCGGATCGACCGGTTATTcagctg
```

FIG. 6B

Library Construction after SfiI digestion:

```
------Headpiece------><----linker---->   <library>
                                    BspE I
Xho I                             Stu I                                       Msc I       Sal I
   E  A  A  M  A  E  L  N  Y  I  P  R  S  Q  E  A  S  G  G  G     X12  *
GAAGCGGCGATGGCGGAGCTGAATTACATTCCCcggtcgcaggagGCCTCCG gaggtggt (NNK)12 taactaagtaaagc TGGCCAATAAgtcgac
CTTCGCCGCTACCGCCTCGACTTAATGTAAGGGccagcgtcctcCGGA ggcctccacca        attgattcatt TCGACCGGTTATTcagctg
                              ↑                                   ↑
                           ON-829                               ON-830
                                                    ↗
                                                ON-1679
```

FIG. 6C

SEQUENCE LISTING (1) GENERAL INFORMATION:

(iii) NUMBER OF SEQUENCES: 232

(2) INFORMATION FOR SEQ ID NO: 1:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 1:

Trp Ser Xaa Trp Ser
1               5

(2) INFORMATION FOR SEQ ID NO: 2:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 2:

Xaa Xaa Xaa Xaa Xaa Xaa Xaa
1               5

(2) INFORMATION FOR SEQ ID NO: 3:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 3:

```
Xaa Gly Xaa Xaa Xaa Xaa Xaa Trp Xaa
1               5

(2) INFORMATION FOR SEQ ID NO: 4:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 4:

Xaa Gly Pro Thr Leu Arg Xaa Trp Xaa
1               5

(2) INFORMATION FOR SEQ ID NO: 5:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 5:

Xaa Xaa Gly Xaa Xaa Xaa Xaa Xaa Trp Xaa
1               5                   10

(2) INFORMATION FOR SEQ ID NO: 6:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 6:

Gly Gly Cys Ala Asp Gly Pro Thr Leu Arg Glu Trp Ile Ser Phe Cys
1               5                   10                  15

Gly Gly (2) INFORMATION FOR SEQ ID NO: 7:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 7:

Gly Asn Ala Asp Gly Pro Thr Leu Arg Gln Trp Leu Glu Gly Arg Arg
1               5                   10                  15

Pro Lys Asn (2) INFORMATION FOR SEQ ID NO: 8:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear
```

(ii) MOLECULE TYPE: peptide (xi) SEQUENCE DESCRIPTION: SEQ ID NO: 8:

Gly Gly Cys Ala Asp Gly Pro Thr Leu Arg Glu Trp Ile Ser Phe Cys
1               5                   10                  15
Gly Gly Lys (2) INFORMATION FOR SEQ ID NO: 9:

(i) SEQUENCE CHARACTERISTICS:
                (A) LENGTH: 18 amino acids
                (B) TYPE: amino acid
                (C) STRANDEDNESS: <Unknown>
                (D) TOPOLOGY: linear (ii) MOLECULE TYPE: peptide (xi) SEQUENCE DESCRIPTION: SEQ ID NO: 9:

Thr Ile Lys Gly Pro Thr Leu Arg Gln Trp Leu Lys Ser Arg Glu His
1               5                   10                  15
Thr Ser (2) INFORMATION FOR SEQ ID NO: 10:

(i) SEQUENCE CHARACTERISTICS:
                (A) LENGTH: 18 amino acids
                (B) TYPE: amino acid
                (C) STRANDEDNESS: <Unknown>
                (D) TOPOLOGY: linear (ii) MOLECULE TYPE: peptide (xi) SEQUENCE DESCRIPTION: SEQ ID NO: 10:

Ser Ile Glu Gly Pro Thr Leu Arg Glu Trp Leu Thr Ser Arg Thr Pro
1               5                   10                  15
His Ser (2) INFORMATION FOR SEQ ID NO: 11:

(i) SEQUENCE CHARACTERISTICS:
                (A) LENGTH: 19 amino acids
                (B) TYPE: amino acid
                (C) STRANDEDNESS: <Unknown>
                (D) TOPOLOGY: linear (ii) MOLECULE TYPE: peptide (xi) SEQUENCE DESCRIPTION: SEQ ID NO: 11:

Leu Ala Ile Glu Gly Pro Thr Leu Arg Gln Trp Leu His Gly Asn Gly
1               5                   10                  15
Arg Asp Thr (2) INFORMATION FOR SEQ ID NO: 12:

(i) SEQUENCE CHARACTERISTICS:
                (A) LENGTH: 14 amino acids
                (B) TYPE: amino acid
                (C) STRANDEDNESS: <Unknown>
                (D) TOPOLOGY: linear (ii) MOLECULE TYPE: peptide (xi) SEQUENCE DESCRIPTION: SEQ ID NO: 12:

Cys Ala Asp Gly Pro Thr Leu Arg Glu Trp Ile Ser Phe Cys
1               5                   10

(2) INFORMATION FOR SEQ ID NO: 13:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 13:

```
Ile Glu Gly Pro Thr Leu Arg Gln Trp Leu Ala Ala Arg Ala
1               5                   10
```

(2) INFORMATION FOR SEQ ID NO: 14:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 14:

```
Cys Xaa Xaa Xaa Xaa Xaa Xaa
1               5
```

(2) INFORMATION FOR SEQ ID NO: 15:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 15:

```
Gly Gly Cys Thr Leu Arg Glu Trp Leu His Gly Gly Phe Cys Gly Gly
1               5                   10                  15
```

(2) INFORMATION FOR SEQ ID NO: 16:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 16:

```
Xaa Cys Xaa Xaa Xaa Xaa Xaa Xaa
1               5
```

(2) INFORMATION FOR SEQ ID NO: 17:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 17:

```
Ile Glu Gly Pro Thr Leu Arg Gln Trp Leu Ala Ala Arg Ala Lys
```

(2) INFORMATION FOR SEQ ID NO: 18:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 15
        (D) OTHER INFORMATION: /product= "Beta-ala"

(xi) SEQUENCE DESCRIPTION: SEQ ID NO: 18:

```
Ile Glu Gly Pro Thr Leu Arg Gln Trp Leu Ala Ala Arg Ala Xaa Lys
 1               5                  10                  15
```

(2) INFORMATION FOR SEQ ID NO: 19:

(i) SEQUENCE CHARACTERISTICS:
        (A) LENGTH: 93 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..84

(xi) SEQUENCE DESCRIPTION: SEQ ID NO: 19:

```
CTC GAG AGC GGG CAG GTG GTG CAT GGG GAG CAG GTG GGT GGT GAG GCC         48
Leu Glu Ser Gly Gln Val Val His Gly Glu Gln Val Gly Gly Glu Ala
 1               5                  10                  15

TCC GGG GCC GTT AAC GGC CGT GGC CTA GCT GGC CAA TAAGTCGAC              93
Ser Gly Ala Val Asn Gly Arg Gly Leu Ala Gly Gln
                20                  25
```

(2) INFORMATION FOR SEQ ID NO: 20:

(i) SEQUENCE CHARACTERISTICS:
        (A) LENGTH: 28 amino acids
        (B) TYPE: amino acid
        (D) TOPOLOGY: linear (ii) MOLECULE TYPE: protein (xi) SEQUENCE DESCRIPTION: SEQ ID NO: 20:

```
Leu Glu Ser Gly Gln Val Val His Gly Glu Gln Val Gly Gly Glu Ala
 1               5                  10                  15

Ser Gly Ala Val Asn Gly Arg Gly Leu Ala Gly Gln
                20                  25
```

(2) INFORMATION FOR SEQ ID NO: 21:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 21:

```
Xaa Xaa Xaa Xaa Xaa Thr Leu Arg Glu Trp Leu Xaa Xaa Xaa Xaa
1               5                   10                  15

Xaa Xaa
```

(2) INFORMATION FOR SEQ ID NO: 22:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 22:

```
Xaa Xaa Xaa Xaa Xaa Xaa Thr Leu Arg Glu Trp Leu Xaa Xaa Xaa Xaa
1               5                   10                  15

Xaa Xaa Xaa
```

(2) INFORMATION FOR SEQ ID NO: 23:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 23:

```
Xaa Xaa Xaa Xaa Xaa Thr Leu Arg Glu Trp Leu Xaa Xaa Xaa Xaa Xaa
1               5                   10                  15

Xaa Xaa
```

(2) INFORMATION FOR SEQ ID NO: 24:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 24:

```
Xaa Xaa Xaa Xaa Xaa Thr Leu Arg Glu Phe Leu Xaa Xaa Xaa Xaa Xaa
1               5                   10                  15

Xaa Xaa
```

(2) INFORMATION FOR SEQ ID NO: 25:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 25:

```
Arg Glu Gly Pro Thr Leu Arg Gln Trp Met
1               5                   10
```

(2) INFORMATION FOR SEQ ID NO: 26:

(i) SEQUENCE CHARACTERISTICS:

(A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 26:

Arg Glu Gly Pro Thr Leu Arg Gln Trp Met
1               5                   10

(2) INFORMATION FOR SEQ ID NO: 27:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 27:

Ser Arg Gly Met Thr Leu Arg Glu Trp Leu
1               5                   10

(2) INFORMATION FOR SEQ ID NO: 28:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 28:

Glu Gly Pro Thr Leu Arg Gly Trp Leu Ala
1               5                   10

(2) INFORMATION FOR SEQ ID NO: 29:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 29:

Arg Glu Gly Gln Thr Leu Lys Glu Trp Leu
1               5                   10

(2) INFORMATION FOR SEQ ID NO: 30:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 30:

Glu Arg Gly Pro Phe Trp Ala Lys Ala Cys
1               5                   10

(2) INFORMATION FOR SEQ ID NO: 31:

(i) SEQUENCE CHARACTERISTICS:
    (A) LENGTH: 10 amino acids
    (B) TYPE: amino acid
    (C) STRANDEDNESS: <Unknown>
    (D) TOPOLOGY: linear (ii) MOLECULE TYPE: peptide (xi) SEQUENCE DESCRIPTION: SEQ ID NO: 31:

Arg Glu Gly Pro Arg Cys Val Met Trp Met
1               5                   10

(2) INFORMATION FOR SEQ ID NO: 32:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 32:

Cys Ser Gly Leu Thr Leu Arg Glu Trp Leu Val Cys
1               5                   10

(2) INFORMATION FOR SEQ ID NO: 33:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 33:

Cys Leu Thr Gly Pro Phe Val Thr Gln Trp Leu Tyr Glu Cys
1               5                   10

(2) INFORMATION FOR SEQ ID NO: 34:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 34:

Cys Gly Glu Gly Leu Thr Leu Thr Gln Trp Leu Glu His Cys
1               5                   10

(2) INFORMATION FOR SEQ ID NO: 35:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 35:

Cys Arg Ala Gly Pro Thr Leu Leu Glu Trp Leu Thr Leu Cys
1               5                   10

(2) INFORMATION FOR SEQ ID NO: 36:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 36:

Cys Arg Ala Gly Pro Thr Leu Leu Glu Trp Leu Thr Leu Cys
1               5                   10

(2) INFORMATION FOR SEQ ID NO: 37:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 37:

Cys Arg Gln Gly Pro Thr Leu Thr Ala Trp Leu Leu Glu Cys
1               5                   10

(2) INFORMATION FOR SEQ ID NO: 38:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 38:

Cys Ala Asp Gly Pro Thr Leu Arg Glu Trp Ile Ser Phe Cys
1               5                   10

(2) INFORMATION FOR SEQ ID NO: 39:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 39:

Cys Glu Leu Val Gly Pro Ser Leu Met Ser Trp Leu Thr Cys
1               5                   10

(2) INFORMATION FOR SEQ ID NO: 40:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 40:

Cys Gly Thr Glu Gly Pro Thr Leu Ser Thr Trp Leu Asp Cys
1               5                   10

(2) INFORMATION FOR SEQ ID NO: 41:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 41:

```
Cys Asp Gln Leu Gly Val Thr Leu Ser Arg Trp Leu Glu Cys
1               5                   10
```

(2) INFORMATION FOR SEQ ID NO: 42:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 42:

```
Ser Gly Thr Gly Leu Thr Leu Arg Glu Trp Leu Gly Ser Phe Ser Leu
1               5                   10                  15
Leu Ser
```

(2) INFORMATION FOR SEQ ID NO: 43:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 43:

```
Cys Pro Glu Gly Pro Thr Leu Leu Gln Trp Leu Lys Arg Gly Tyr Ser
1               5                   10                  15
Ser Cys
```

(2) INFORMATION FOR SEQ ID NO: 44:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 44:

```
Arg Gly Asp Gly Pro Thr Leu Ser Gln Trp Leu Tyr Ser Leu Met Ile
1               5                   10                  15
Met Cys
```

(2) INFORMATION FOR SEQ ID NO: 45:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 45:

Met Val Ala Gly Pro Thr Leu Arg Glu Phe Ile Ala Ser Leu Pro Ile
1               5                   10                  15

His Cys (2) INFORMATION FOR SEQ ID NO: 46:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 46:

Ser Met Gln Gly Pro Thr Phe Arg Glu Trp Val Ser Met Met Lys Val
1               5                   10                  15

Leu Cys (2) INFORMATION FOR SEQ ID NO: 47:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 47:

Ser Val Gln Cys Gly Pro Thr Leu Arg Gln Trp Leu Ala Ala Arg Asn
1               5                   10                  15

His Leu Ser (2) INFORMATION FOR SEQ ID NO: 48:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 48:

Gly Asn Ala Asp Gly Pro Thr Leu Arg Gln Trp Leu Glu Gly Arg Arg
1               5                   10                  15

Pro Lys Asn (2) INFORMATION FOR SEQ ID NO: 49:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 49:

Ser Val Arg Cys Gly Pro Thr Leu Arg Gln Trp Leu Ala Ala Arg Thr
1               5                   10                  15

His Leu Ser (2) INFORMATION FOR SEQ ID NO: 50:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 50:

```
Leu Ala Ile Glu Gly Pro Thr Leu Arg Gln Trp Leu His Gly Asn Gly
1               5                   10                  15

Arg Asp Thr
```

(2) INFORMATION FOR SEQ ID NO: 51:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 51:

```
His Gly Arg Val Gly Pro Thr Leu Arg Glu Trp Lys Thr Gln Val Ala
1               5                   10                  15

Thr Lys Lys
```

(2) INFORMATION FOR SEQ ID NO: 52:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 52:

```
Cys Ala Asp Gly Pro Thr Leu Arg Glu Trp Ile Ser Phe Cys
1               5                   10
```

(2) INFORMATION FOR SEQ ID NO: 53:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 53:

```
Ile Ser Asp Gly Pro Thr Leu Lys Glu Trp Leu Ser Val Thr Arg Gly
1               5                   10                  15

Ala Ser
```

(2) INFORMATION FOR SEQ ID NO: 54:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 54:

Ser Ile Glu Gly Pro Thr Leu Arg Glu Trp Leu Thr Ser Arg Thr Pro
1               5                   10                  15
His Ser (2) INFORMATION FOR SEQ ID NO: 55:

(i) SEQUENCE CHARACTERISTICS:
            (A) LENGTH: 18 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 55:

Thr Ile Lys Gly Pro Thr Leu Arg Gln Trp Leu Lys Ser Arg Glu His
1               5                   10                  15
Thr Ser (2) INFORMATION FOR SEQ ID NO: 56:

(i) SEQUENCE CHARACTERISTICS:
            (A) LENGTH: 19 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 56:

Gly Asn Ala Asp Gly Pro Thr Leu Arg Gln Trp Leu Glu Gly Arg Arg
1               5                   10                  15
Pro Lys Asn (2) INFORMATION FOR SEQ ID NO: 57:

(i) SEQUENCE CHARACTERISTICS:
            (A) LENGTH: 18 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 57:

Ser Ile Glu Gly Pro Thr Leu Arg Glu Trp Leu Thr Ser Arg Thr Pro
1               5                   10                  15
His Ser (2) INFORMATION FOR SEQ ID NO: 58:

(i) SEQUENCE CHARACTERISTICS:
            (A) LENGTH: 18 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 58:

Ile Ser Asp Gly Pro Thr Leu Lys Glu Trp Leu Ser Val Thr Arg Gly
1               5                   10                  15

Ala Ser (2) INFORMATION FOR SEQ ID NO: 59:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 59:

Cys Ser Leu Glu Asp Leu Arg Lys Arg Cys
1               5                   10

(2) INFORMATION FOR SEQ ID NO: 60:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 60:

Cys Arg Arg Ser Glu Leu Leu Glu Arg Cys
1               5                   10

(2) INFORMATION FOR SEQ ID NO: 61:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 61:

Cys Thr Phe Lys Gln Phe Leu Asp Gly Cys
1               5                   10

(2) INFORMATION FOR SEQ ID NO: 62:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 62:

Cys Thr Arg Gly Glu Trp Leu Arg Cys Cys
1               5                   10

(2) INFORMATION FOR SEQ ID NO: 63:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 63:

```
Cys Thr Leu Arg Gln Trp Leu Gln Gly Cys
1               5                   10
```

(2) INFORMATION FOR SEQ ID NO: 64:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 64:

```
Cys Thr Leu Glu Glu Leu Arg Ala Cys Cys
1               5                   10
```

(2) INFORMATION FOR SEQ ID NO: 65:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 65:

```
Cys Thr Arg Glu Glu Leu Met Arg Leu Cys
1               5                   10
```

(2) INFORMATION FOR SEQ ID NO: 66:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 66:

```
Cys Gln Arg Ala Asp Leu Ile Asn Phe Cys
1               5                   10
```

(2) INFORMATION FOR SEQ ID NO: 67:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 67:

```
Cys Asn Arg Asn Asp Leu Leu Leu Phe Cys
1               5                   10
```

(2) INFORMATION FOR SEQ ID NO: 68:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 68:

Cys Thr Arg Thr Glu Trp Leu His Gly Cys
1               5                   10

(2) INFORMATION FOR SEQ ID NO: 69:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 69:

Cys Thr Leu Glu Phe Met Asn Gly Cys
1               5

(2) INFORMATION FOR SEQ ID NO: 70:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 70:

Cys Ser Leu Gly Glu Leu Arg Arg Leu Cys
1               5                   10

(2) INFORMATION FOR SEQ ID NO: 71:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 71:

Cys Asn Ile Asn Gln Leu Arg Ser Ile Cys
1               5                   10

(2) INFORMATION FOR SEQ ID NO: 72:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 72:

Cys Thr Met Arg Gln Phe Leu Val Cys Cys
1               5                   10

(2) INFORMATION FOR SEQ ID NO: 73:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 73:

Cys Thr Arg Ser Glu Trp Leu Glu Arg Cys
1               5                   10

(2) INFORMATION FOR SEQ ID NO: 74:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 74:

Cys Thr Leu His Glu Tyr Leu Ser Gly Cys
1               5                   10

(2) INFORMATION FOR SEQ ID NO: 75:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 75:

Cys Thr Arg Glu Glu Leu Leu Arg Gln Cys
1               5                   10

(2) INFORMATION FOR SEQ ID NO: 76:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 76:

Cys Thr Phe Arg Glu Phe Val Asn Gly Cys
1               5                   10

(2) INFORMATION FOR SEQ ID NO: 77:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 77:

Cys Ser Arg Ala Asp Phe Leu Ala Ala Cys
1               5                   10

(2) INFORMATION FOR SEQ ID NO: 78:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear

```
        (ii) MOLECULE TYPE: peptide (xi) SEQUENCE DESCRIPTION: SEQ ID NO: 78:

Cys Ser Cys Ala Gln Val Val Gln Cys Cys
1               5                   10

(2) INFORMATION FOR SEQ ID NO: 79:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 79:

Cys Thr Leu Arg Gln Trp Ile Leu Leu Gly Met Cys
1               5                   10

(2) INFORMATION FOR SEQ ID NO: 80:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 80:

Cys Thr Leu Arg Glu Trp Leu His Gly Gly Phe Cys
1               5                   10

(2) INFORMATION FOR SEQ ID NO: 81:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 81:

Cys Thr Leu Arg Ala Trp Leu Met Ser Glu Thr Cys
1               5                   10

(2) INFORMATION FOR SEQ ID NO: 82:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 82:

Cys Thr Leu Arg Ala Trp Leu Met Glu Ser Cys Cys
1               5                   10

(2) INFORMATION FOR SEQ ID NO: 83:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear
```

(ii) MOLECULE TYPE: peptide (xi) SEQUENCE DESCRIPTION: SEQ ID NO: 83:

Cys Thr Phe Gln Val Trp Lys Leu Ala Arg Asn Cys
1               5                   10

(2) INFORMATION FOR SEQ ID NO: 84:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 84:

Cys Leu Leu Arg Glu Trp Leu Asp Xaa Arg Thr Cys
1               5                   10

(2) INFORMATION FOR SEQ ID NO: 85:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 85:

Cys Val Leu Arg Glu Trp Leu Leu Xaa Xaa Ser Cys
1               5                   10

(2) INFORMATION FOR SEQ ID NO: 86:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 86:

Cys Leu Leu Ser Glu Phe Leu Ala Gly Gln Gln Cys
1               5                   10

(2) INFORMATION FOR SEQ ID NO: 87:

(i) SEQUENCE CHARACTERISTICS:
            (A) LENGTH: 14 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 87:

Cys Ser Leu Arg Gln Tyr Leu Asp Phe Gly Leu Gly Ser Cys
1               5                   10

(2) INFORMATION FOR SEQ ID NO: 88:

(i) SEQUENCE CHARACTERISTICS:
            (A) LENGTH: 14 amino acids
            (B) TYPE: amino acid
            (C) STRANDEDNESS: <Unknown>

(D) TOPOLOGY: linear (ii) MOLECULE TYPE: peptide (xi) SEQUENCE DESCRIPTION: SEQ ID NO: 88:

Cys Thr Leu Gln Glu Leu Lys Gln Ser Ser Leu Tyr Glu Cys
1               5                   10

(2) INFORMATION FOR SEQ ID NO: 89:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 89:

Cys Asp Leu Ser Glu Leu Lys Thr His Gly Tyr Ala Tyr Cys
1               5                   10

(2) INFORMATION FOR SEQ ID NO: 90:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 90:

Cys Lys Leu Ser Asp Trp Leu Met Asn Gly Val Ala Ala Cys
1               5                   10

(2) INFORMATION FOR SEQ ID NO: 91:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 91:

Cys Ser Leu Gln Glu Phe Leu Ser His Gly Gly Tyr Val Cys
1               5                   10

(2) INFORMATION FOR SEQ ID NO: 92:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 92:

Cys Ser Leu Lys Glu Phe Leu His Ser Gly Leu Met Gln Cys
1               5                   10

(2) INFORMATION FOR SEQ ID NO: 93:

(i) SEQUENCE CHARACTERISTICS:
        (A) LENGTH: 14 amino acids
        (B) TYPE: amino acid

```
        (C) STRANDEDNESS: <Unknown>
        (D) TOPOLOGY: linear (ii) MOLECULE TYPE: peptide (xi) SEQUENCE DESCRIPTION: SEQ ID NO: 93:

Cys Thr Phe Arg Gln Leu Leu Glu Tyr Gly Val Ser Ser Cys
1               5                   10

(2) INFORMATION FOR SEQ ID NO: 94:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 94:

Cys Thr Met Arg Glu Phe Leu Val Ala Ser Gly Val Ala Cys
1               5                   10

(2) INFORMATION FOR SEQ ID NO: 95:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 95:

Cys Thr Leu Ala Glu Phe Leu Ala Ser Gly Val Glu Gln Cys
1               5                   10

(2) INFORMATION FOR SEQ ID NO: 96:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 96:

Cys Thr Leu Ala Glu Phe Leu Ala Ser Gly Val Glu Gln Cys
1               5                   10

(2) INFORMATION FOR SEQ ID NO: 97:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 97:

Cys Thr Leu Lys Glu Trp Leu Val Ser His Glu Val Trp Cys
1               5                   10

(2) INFORMATION FOR SEQ ID NO: 98:

(i) SEQUENCE CHARACTERISTICS:
        (A) LENGTH: 14 amino acids
```

```
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 98:

Cys Thr Leu Arg Glu Phe Leu Ser Leu Gly Met Asn Ala Cys
1               5                   10

(2) INFORMATION FOR SEQ ID NO: 99:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 99:

Cys Thr Leu Arg Glu Phe Leu Asp Pro Thr Thr Ala Val Cys
1               5                   10

(2) INFORMATION FOR SEQ ID NO: 100:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 100:

Cys Ser Leu Leu Glu Phe Leu Ala Leu Gly Val Ala Leu Cys
1               5                   10

(2) INFORMATION FOR SEQ ID NO: 101:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 101:

Gly Gly Gly Arg Gly Cys Thr Leu Lys Gln Trp Lys Gln Gly Asp Cys
1               5                   10                  15

Gly Arg Ser (2) INFORMATION FOR SEQ ID NO: 102:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 102:

Cys Asn Arg Ser Gln Leu Leu Ala Ala Cys
1               5                   10

(2) INFORMATION FOR SEQ ID NO: 103:
```

```
    (i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 103:

Cys Thr Leu Gln Gln Trp Leu Ser Gly Cys
1               5                   10

(2) INFORMATION FOR SEQ ID NO: 104:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 104:

Cys Thr Leu Arg Glu Phe Lys Ala Gly Cys
1               5                   10

(2) INFORMATION FOR SEQ ID NO: 105:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 105:

Cys Thr Arg Ala Gln Phe Leu Lys Gly Cys
1               5                   10

(2) INFORMATION FOR SEQ ID NO: 106:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 106:

Cys Thr Leu Arg Glu Phe Asn Arg Gly Cys
1               5                   10

(2) INFORMATION FOR SEQ ID NO: 107:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 107:

Cys Thr Leu Ser Asp Phe Lys Arg Gly Cys
1               5                   10
```

```
(2) INFORMATION FOR SEQ ID NO: 108:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 108:

Cys Thr Phe Arg Gln Trp Lys Glu Ala Cys
1               5                   10

(2) INFORMATION FOR SEQ ID NO: 109:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 109:

Cys Thr Leu Ser Glu Phe Arg Gly Gly Cys
1               5                   10

(2) INFORMATION FOR SEQ ID NO: 110:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 110:

Cys Thr Leu Gln Glu Phe Leu Glu Gly Cys
1               5                   10

(2) INFORMATION FOR SEQ ID NO: 111:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 111:

Cys Thr Leu Gln Gln Trp Lys Asp Gly Cys
1               5                   10

(2) INFORMATION FOR SEQ ID NO: 112:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 112:

Cys Thr Arg Ser Gln Trp Leu Glu Gly Cys
1               5                   10
```

(2) INFORMATION FOR SEQ ID NO: 113:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 113:

```
Cys Ser Leu Gln Glu Phe Lys His Gly Cys
1               5                   10
```

(2) INFORMATION FOR SEQ ID NO: 114:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 114:

```
Cys Thr Leu Gly Glu Trp Lys Arg Gly Cys
1               5                   10
```

(2) INFORMATION FOR SEQ ID NO: 115:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 115:

```
Cys Thr Leu Trp Gly Cys Gly Lys Arg Gly Cys
1               5                   10
```

(2) INFORMATION FOR SEQ ID NO: 116:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 116:

```
Cys Thr Leu Gln Glu Trp Arg Gly Gly Cys
1               5                   10
```

(2) INFORMATION FOR SEQ ID NO: 117:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 117:

```
Cys Thr Arg Leu Ser Gly Cys Trp Leu Cys
1               5                   10
```

(2) INFORMATION FOR SEQ ID NO: 118:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 118:

Cys Thr Arg Thr Gln Trp Leu Leu Asp Cys
1               5                   10

(2) INFORMATION FOR SEQ ID NO: 119:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 119:

Cys Thr Leu Ala Glu Phe Arg Arg Gly Cys
1               5                   10

(2) INFORMATION FOR SEQ ID NO: 120:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 120:

Cys Thr Ser Thr Gln Trp Leu Leu Ala Cys
1               5                   10

(2) INFORMATION FOR SEQ ID NO: 121:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 121:

Cys Ser Arg Ser Gln Phe Leu Arg Ser Cys
1               5                   10

(2) INFORMATION FOR SEQ ID NO: 122:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 122:

Cys Thr Leu Arg Glu Trp Leu Glu Gly Cys

```
1               5                    10
```

(2) INFORMATION FOR SEQ ID NO: 123:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 123:

```
Cys Thr Leu Arg Glu Phe Leu Leu Met Gly Ala Cys
1               5                    10
```

(2) INFORMATION FOR SEQ ID NO: 124:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 124:

```
Cys Thr Leu Lys Glu Trp Leu Leu Trp Ser Ser Cys
1               5                    10
```

(2) INFORMATION FOR SEQ ID NO: 125:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 125:

```
Cys Thr Leu Leu Glu Trp Leu Arg Asn Pro Val Cys
1               5                    10
```

(2) INFORMATION FOR SEQ ID NO: 126:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 126:

```
Cys Thr Leu Arg Gln Trp Leu Gly Asp Ala Trp Cys
1               5                    10
```

(2) INFORMATION FOR SEQ ID NO: 127:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 127:

```
Cys Thr Leu Gly Gln Trp Leu Gln Met Gly Met Cys
1               5                   10
```

(2) INFORMATION FOR SEQ ID NO: 128:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 128:

```
Cys Thr Leu Arg Glu Trp Val Phe Ala Gly Leu Cys
1               5                   10
```

(2) INFORMATION FOR SEQ ID NO: 129:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 129:

```
Cys Leu Leu Leu Glu Phe Leu Ser Gly Ala Asp Cys
1               5                   10
```

(2) INFORMATION FOR SEQ ID NO: 130:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 130:

```
Cys Thr Leu Gly Glu Phe Leu Ala Gly His Leu Cys
1               5                   10
```

(2) INFORMATION FOR SEQ ID NO: 131:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 131:

```
Cys Arg Leu Arg Glu Phe Leu Val Asp Leu Thr Cys
1               5                   10
```

(2) INFORMATION FOR SEQ ID NO: 132:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 132:

Cys Ser Phe Arg Ser Trp Leu Val Asp Gln Thr Cys
1               5                   10

(2) INFORMATION FOR SEQ ID NO: 133:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 133:

Cys Thr Leu Arg Glu Trp Leu Glu Asp Leu Gly Cys
1               5                   10

(2) INFORMATION FOR SEQ ID NO: 134:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 134:

Cys Thr Leu Gln Asp Trp Leu Val Ser Trp Thr Cys
1               5                   10

(2) INFORMATION FOR SEQ ID NO: 135:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 135:

Cys Thr Leu Ser Glu Trp Leu Ser Glu Leu Ser Cys
1               5                   10

(2) INFORMATION FOR SEQ ID NO: 136:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 136:

Cys Thr Leu Met Gln Trp Leu Gly Gly Trp Pro Cys
1               5                   10

(2) INFORMATION FOR SEQ ID NO: 137:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide

```
        (xi) SEQUENCE DESCRIPTION: SEQ ID NO: 137:

Cys Thr Leu Arg Glu Trp Leu Ser Tyr Gly Thr Cys
1               5                   10

(2) INFORMATION FOR SEQ ID NO: 138:

(i) SEQUENCE CHARACTERISTICS:
          (A) LENGTH: 12 amino acids
          (B) TYPE: amino acid
          (C) STRANDEDNESS: <Unknown>
          (D) TOPOLOGY: linear (ii) MOLECULE TYPE: peptide (xi) SEQUENCE DESCRIPTION: SEQ ID NO: 138:

Cys Thr Leu Gln Glu Trp Leu Ser Gly Gly Leu Cys
1               5                   10

(2) INFORMATION FOR SEQ ID NO: 139:

(i) SEQUENCE CHARACTERISTICS:
          (A) LENGTH: 18 amino acids
          (B) TYPE: amino acid
          (C) STRANDEDNESS: <Unknown>
          (D) TOPOLOGY: linear (ii) MOLECULE TYPE: peptide (xi) SEQUENCE DESCRIPTION: SEQ ID NO: 139:

Gly Ser His Gly Cys Thr Leu Arg Glu Trp Leu Cys Met Lys Ile Val
1               5                   10                  15

Pro Cys (2) INFORMATION FOR SEQ ID NO: 140:

(i) SEQUENCE CHARACTERISTICS:
          (A) LENGTH: 18 amino acids
          (B) TYPE: amino acid
          (C) STRANDEDNESS: <Unknown>
          (D) TOPOLOGY: linear (ii) MOLECULE TYPE: peptide (xi) SEQUENCE DESCRIPTION: SEQ ID NO: 140:

Gln Trp Gln Gly Cys Thr Leu Arg Asp Cys Ile Leu Arg Gly Val Phe
1               5                   10                  15

Trp Ser (2) INFORMATION FOR SEQ ID NO: 141:

(i) SEQUENCE CHARACTERISTICS:
          (A) LENGTH: 18 amino acids
          (B) TYPE: amino acid
          (C) STRANDEDNESS: <Unknown>
          (D) TOPOLOGY: linear (ii) MOLECULE TYPE: peptide (xi) SEQUENCE DESCRIPTION: SEQ ID NO: 141:

Ser Val Asn Ser Cys Thr Leu Arg Glu Phe Leu Thr Gly Cys Arg Val
1               5                   10                  15

Phe Cys (2) INFORMATION FOR SEQ ID NO: 142:

(i) SEQUENCE CHARACTERISTICS:
```

(A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 142:

Ser Tyr Asp Gly Cys Thr Leu Arg His Trp Leu Met Asp Ile Tyr Gly
1               5                  10                  15

Asp Cys (2) INFORMATION FOR SEQ ID NO: 143:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 143:

Gln Arg Ser Gly Cys Thr Leu Arg Asp Trp Val Leu Leu Asn Cys Leu
1               5                  10                  15

Ala Ser (2) INFORMATION FOR SEQ ID NO: 144:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 144:

Asn Tyr Arg Gly Cys Thr Leu Ser Gln Trp Val Ser Glu Gln Ile Val
1               5                  10                  15

Gly Cys (2) INFORMATION FOR SEQ ID NO: 145:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 145:

Gly Arg Ser Gly Cys Thr Leu Arg Glu Tyr Leu Gly Gly Met Cys Tyr
1               5                  10                  15

Leu Ser (2) INFORMATION FOR SEQ ID NO: 146:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 146:

Ala Ser Trp Tyr Cys Thr Val Pro Glu Leu Met Glu Met Gln Leu Pro
1               5                   10                  15
Glu Cys (2) INFORMATION FOR SEQ ID NO: 147:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 147:

Gly Ser Thr Gly Cys Thr Leu Arg Glu Xaa Leu His Met Leu Gly Leu
1               5                   10                  15
Asp Cys (2) INFORMATION FOR SEQ ID NO: 148:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 148:

Ala Cys Glu Gly Cys Thr Leu Arg Gln Trp Leu Glu Tyr Val Arg Val
1               5                   10                  15
Gly Cys (2) INFORMATION FOR SEQ ID NO: 149:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 149:

Ala Gln Arg Gly Cys Thr Leu Gln Tyr Phe Val Ser Tyr Gly Xaa Asp
1               5                   10                  15
Met Cys (2) INFORMATION FOR SEQ ID NO: 150:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 150:

Gly Val Cys Gly Cys Thr Leu Arg Glu Phe Leu Ala Ile Pro His Thr
1               5                   10                  15
Ser Cys (2) INFORMATION FOR SEQ ID NO: 151:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 151:

```
Ser Glu Gly Gly Cys Thr Leu Arg Glu Trp Val Ala Ser Ser Leu Ala
 1               5                  10                  15
Asn Cys
```

(2) INFORMATION FOR SEQ ID NO: 152:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 152:

```
Ser Asn Ser Arg Cys Thr Leu Arg Glu Trp Ile Ile Gln Gly Cys Asp
 1               5                  10                  15
Phe Ser
```

(2) INFORMATION FOR SEQ ID NO: 153:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 153:

```
Ser Asn Ser Arg Cys Thr Leu Arg Glu Trp Ile Ile Gln Gly Cys Asp
 1               5                  10                  15
Phe Ser
```

(2) INFORMATION FOR SEQ ID NO: 154:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 154:

```
Cys Leu Gly Cys Thr Leu Ser Gln Trp Arg Lys Arg Thr Arg Cys Asp
 1               5                  10                  15
Thr His
```

(2) INFORMATION FOR SEQ ID NO: 155:

(i) SEQUENCE CHARACTERISTICS:
        (A) LENGTH: 17 amino acids
        (B) TYPE: amino acid
        (C) STRANDEDNESS: <Unknown>

(D) TOPOLOGY: linear (ii) MOLECULE TYPE: peptide (xi) SEQUENCE DESCRIPTION: SEQ ID NO: 155:

Tyr Arg Gly Cys Ser Arg Ala Gln Leu Leu Gly Gly Glu Cys Arg Lys
1               5                   10                  15

Lys (2) INFORMATION FOR SEQ ID NO: 156:

(i) SEQUENCE CHARACTERISTICS:
            (A) LENGTH: 17 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 156:

Gly Arg Gly Cys Thr Leu Lys Gln Trp Lys Gln Gly Asp Cys Gly Arg
1               5                   10                  15

Ser (2) INFORMATION FOR SEQ ID NO: 157:

(i) SEQUENCE CHARACTERISTICS:
            (A) LENGTH: 19 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 157:

Val Arg Gly Gly Cys Ala Leu Arg Asp Trp Val Ala Gly Glu Cys Phe
1               5                   10                  15

Asp Trp Thr (2) INFORMATION FOR SEQ ID NO: 158:

(i) SEQUENCE CHARACTERISTICS:
            (A) LENGTH: 19 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 158:

Leu Trp Arg Gly Cys Thr Leu Asn Gly Phe Lys Ser Arg His Cys Gly
1               5                   10                  15

Ser Pro Glu (2) INFORMATION FOR SEQ ID NO: 159:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 159:

Cys Thr Leu Arg Ser Trp Lys His Arg Gly Cys Ala Pro (2) INFORMATION FOR SEQ ID NO: 160:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 160:

Gly Arg Gly Cys Thr Arg Ala Gln Trp Leu Ala Gly Cys Cys Thr Gly
1               5                   10                  15
His (2) INFORMATION FOR SEQ ID NO: 161:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 161:

Arg Ala Gly Cys Thr Leu Arg Glu Phe Arg Lys Gly Cys Leu Ala Leu
1               5                   10                  15

(2) INFORMATION FOR SEQ ID NO: 162:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 162:

Lys Arg Gly Cys Thr Leu Ala Glu Met Ile Arg Gly Cys Asn Arg Ser
1               5                   10                  15
Asn (2) INFORMATION FOR SEQ ID NO: 163:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 163:

Gly Arg Gly Cys Thr Leu Lys Gln Trp Lys Gln Gly Asp Cys Gly Arg
1               5                   10                  15
Ser (2) INFORMATION FOR SEQ ID NO: 164:

(i) SEQUENCE CHARACTERISTICS:
        (A) LENGTH: 19 amino acids
        (B) TYPE: amino acid
        (C) STRANDEDNESS: <Unknown>

(D) TOPOLOGY: linear (ii) MOLECULE TYPE: peptide (xi) SEQUENCE DESCRIPTION: SEQ ID NO: 164:

Arg Trp Arg Gly Cys Ser Leu Ala Lys Leu Lys Lys Gly Ala Ala Cys
1               5                   10                  15

Gly Arg Gly (2) INFORMATION FOR SEQ ID NO: 165:

(i) SEQUENCE CHARACTERISTICS:
            (A) LENGTH: 16 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 165:

Arg Gly Gly Cys Thr Leu Arg Glu Trp Arg Arg Val Arg Val Ile Asn
1               5                   10                  15

(2) INFORMATION FOR SEQ ID NO: 166:

(i) SEQUENCE CHARACTERISTICS:
            (A) LENGTH: 17 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 166:

Gly Arg Gly Cys Thr Leu Lys Gln Trp Lys Gln Gly Asp Cys Gly Arg
1               5                   10                  15

Ser (2) INFORMATION FOR SEQ ID NO: 167:

(i) SEQUENCE CHARACTERISTICS:
            (A) LENGTH: 17 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 167:

Arg Tyr Gly Cys Thr Arg His Gln Trp Leu Val Gly Thr Cys Val Arg
1               5                   10                  15

His (2) INFORMATION FOR SEQ ID NO: 168:

(i) SEQUENCE CHARACTERISTICS:
            (A) LENGTH: 8 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 168:

Gly Pro Thr Leu Arg Gln Trp Leu
1               5

(2) INFORMATION FOR SEQ ID NO: 169:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 169:

ACCACCTCCG G                                        11

(2) INFORMATION FOR SEQ ID NO: 170:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 170:

TTACTTAGTT A                                        11

(2) INFORMATION FOR SEQ ID NO: 171:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 171:

GAGGTGGTNN NTAACTAAGT AAAGC                          25

(2) INFORMATION FOR SEQ ID NO: 172:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "Pen"

(xi) SEQUENCE DESCRIPTION: SEQ ID NO: 172:

Xaa Ala Asp Gly Pro Thr Leu Arg Glu Trp Ile Ser Phe Cys
1                 5                     10

(2) INFORMATION FOR SEQ ID NO: 173:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 173:

Ala Asp Gly Pro Thr Leu Arg Glu Trp Ile Ser Phe Cys
1               5                   10

(2) INFORMATION FOR SEQ ID NO: 174:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "Homocys"

(xi) SEQUENCE DESCRIPTION: SEQ ID NO: 174:

Xaa Ala Asp Gly Pro Thr Leu Arg Glu Trp Ile Ser Phe Cys
1               5                   10

(2) INFORMATION FOR SEQ ID NO: 175:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "D-Cys"

(ix) FEATURE:
        (A) NAME/KEY: Modified-site
        (B) LOCATION: 14
        (D) OTHER INFORMATION: /product= "D-Cys"

(xi) SEQUENCE DESCRIPTION: SEQ ID NO: 175:

Xaa Ala Asp Gly Pro Thr Leu Arg Glu Trp Ile Ser Phe Xaa
1               5                   10

(2) INFORMATION FOR SEQ ID NO: 176:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 14
        (D) OTHER INFORMATION: /product= "D-Cys"

(xi) SEQUENCE DESCRIPTION: SEQ ID NO: 176:

Cys Ala Asp Gly Pro Thr Leu Arg Glu Trp Ile Ser Phe Xaa
1               5                   10

(2) INFORMATION FOR SEQ ID NO: 177:

(i) SEQUENCE CHARACTERISTICS:
        (A) LENGTH: 14 amino acids

```
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "D-Pen"

(ix) FEATURE:
        (A) NAME/KEY: Modified-site
        (B) LOCATION: 14
        (D) OTHER INFORMATION: /product= "D-Cys"

(xi) SEQUENCE DESCRIPTION: SEQ ID NO: 177:

Xaa Ala Asp Gly Pro Thr Leu Arg Glu Trp Ile Ser Phe Xaa
1               5                   10

(2) INFORMATION FOR SEQ ID NO: 178:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "Homocys"

(ix) FEATURE:
        (A) NAME/KEY: Modified-site
        (B) LOCATION: 14
        (D) OTHER INFORMATION: /product= "Homocys"

(xi) SEQUENCE DESCRIPTION: SEQ ID NO: 178:

Xaa Ala Asp Gly Pro Thr Leu Arg Glu Trp Ile Ser Phe Xaa
1               5                   10

(2) INFORMATION FOR SEQ ID NO: 179:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 13
        (D) OTHER INFORMATION: /product= "Homocys"

(xi) SEQUENCE DESCRIPTION: SEQ ID NO: 179:

Ala Asp Gly Pro Thr Leu Arg Glu Trp Ile Ser Phe Xaa
1               5                   10

(2) INFORMATION FOR SEQ ID NO: 180:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide
```

```
    (ix) FEATURE:
        (A) NAME/KEY: Modified-site
        (B) LOCATION: 13
        (D) OTHER INFORMATION: /product= "Pen"

(xi) SEQUENCE DESCRIPTION: SEQ ID NO: 180:

Ala Asp Gly Pro Thr Leu Arg Glu Trp Ile Ser Phe Xaa
1               5                   10

(2) INFORMATION FOR SEQ ID NO: 181:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 181:

Lys Ala Asp Gly Pro Thr Leu Arg Glu Trp Ile Ser Phe Glu
1               5                   10

(2) INFORMATION FOR SEQ ID NO: 182:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 182:

Glu Ala Asp Gly Pro Thr Leu Arg Glu Trp Ile Ser Phe Lys
1               5                   10

(2) INFORMATION FOR SEQ ID NO: 183:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 183:

Ala Asp Gly Pro Thr Leu Arg Glu Trp Ile Ser Phe Glu
1               5                   10

(2) INFORMATION FOR SEQ ID NO: 184:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "Pen"

(ix) FEATURE:
        (A) NAME/KEY: Modified-site
        (B) LOCATION: 14
        (D) OTHER INFORMATION: /product= "Pen"
```

(xi) SEQUENCE DESCRIPTION: SEQ ID NO: 184:

Xaa Ala Asp Gly Pro Thr Leu Arg Glu Trp Ile Ser Phe Xaa
1               5                   10

(2) INFORMATION FOR SEQ ID NO: 185:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 185:

Cys Ile Glu Gly Pro Thr Leu Arg Gln Trp Leu Ala Ala Arg Ala
1               5                   10                  15

(2) INFORMATION FOR SEQ ID NO: 186:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 186:

Cys Ala Asp Gly Pro Thr Leu Arg Glu Trp Ile Ser Phe
1               5                   10

(2) INFORMATION FOR SEQ ID NO: 187:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 187:

Ser Val Gln Cys Gly Pro Thr Leu Arg Gln Trp Leu Ala Ala Arg Asp
1               5                   10                  15

His Leu Ser (2) INFORMATION FOR SEQ ID NO: 188:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 188:

Met Val Gly Pro Thr Leu Arg Ser Gly Cys
1               5                   10

(2) INFORMATION FOR SEQ ID NO: 189:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 189:

Asp Gly Pro Thr Leu Arg Glu Trp Ile Ser Phe Cys
1               5                   10

(2) INFORMATION FOR SEQ ID NO: 190:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 190:

Gly Pro Thr Leu Arg Glu Trp Ile Ser Phe Cys
1               5                   10

(2) INFORMATION FOR SEQ ID NO: 191:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 191:

Pro Thr Leu Arg Glu Trp Ile Ser Phe Cys
1               5                   10

(2) INFORMATION FOR SEQ ID NO: 192:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 192:

Thr Leu Arg Glu Trp Ile Ser Phe Cys
1               5

(2) INFORMATION FOR SEQ ID NO: 193:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 193:

Ile Glu Gly Pro Thr Leu Arg Gln Trp Leu Ala Ala Arg Ala
1               5                   10

(2) INFORMATION FOR SEQ ID NO: 194:

(i) SEQUENCE CHARACTERISTICS:
        (A) LENGTH: 16 amino acids
        (B) TYPE: amino acid
        (C) STRANDEDNESS: <Unknown>

(D) TOPOLOGY: linear (ii) MOLECULE TYPE: peptide (xi) SEQUENCE DESCRIPTION: SEQ ID NO: 194:

Cys Ile Glu Gly Pro Thr Leu Arg Gln Trp Leu Ala Ala Arg Ala Cy
1               5                   10                  15

(2) INFORMATION FOR SEQ ID NO: 195:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 195:

Ile Glu Gly Pro Thr Leu Arg Gln Trp Leu Ala Ala Arg Lys
1               5                   10

(2) INFORMATION FOR SEQ ID NO: 196:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 14
        (D) OTHER INFORMATION: /product= "Beta-ala"

(xi) SEQUENCE DESCRIPTION: SEQ ID NO: 196:

Ile Glu Gly Pro Thr Leu Arg Gln Trp Leu Ala Ala Arg Xaa Lys
1               5                   10                  15

(2) INFORMATION FOR SEQ ID NO: 197:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 197:

Ile Glu Gly Pro Thr Leu Arg Gln Trp Leu Ala Ala Lys
1               5                   10

(2) INFORMATION FOR SEQ ID NO: 198:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 13
        (D) OTHER INFORMATION: /product= "Beta-ala"

(xi) SEQUENCE DESCRIPTION: SEQ ID NO: 198:

```
Ile Glu Gly Pro Thr Leu Arg Gln Trp Leu Ala Ala Xaa Lys
1               5                  10
```

(2) INFORMATION FOR SEQ ID NO: 199:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 199:

```
Glu Gly Pro Thr Leu Arg Gln Trp Leu Ala Ala Arg Ala Lys
1               5                  10
```

(2) INFORMATION FOR SEQ ID NO: 200:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 14
        (D) OTHER INFORMATION: /product= "Beta-ala"

(xi) SEQUENCE DESCRIPTION: SEQ ID NO: 200:

```
Glu Gly Pro Thr Leu Arg Gln Trp Leu Ala Ala Arg Ala Xaa Lys
1               5                  10                  15
```

(2) INFORMATION FOR SEQ ID NO: 201:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 201:

```
Glu Gly Pro Thr Leu Arg Gln Trp Leu Ala Ala Arg Lys
1               5                  10
```

(2) INFORMATION FOR SEQ ID NO: 202:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 13
        (D) OTHER INFORMATION: /product= "Beta-ala"

(xi) SEQUENCE DESCRIPTION: SEQ ID NO: 202:

```
Glu Gly Pro Thr Leu Arg Gln Trp Leu Ala Ala Arg Xaa Lys
1               5                  10
```

(2) INFORMATION FOR SEQ ID NO: 203:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 203:

Glu Gly Pro Thr Leu Arg Gln Trp Leu Ala Ala Lys
1               5                   10

(2) INFORMATION FOR SEQ ID NO: 204:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 12
        (D) OTHER INFORMATION: /product= "Beta-ala"

(xi) SEQUENCE DESCRIPTION: SEQ ID NO: 204:

Glu Gly Pro Thr Leu Arg Gln Trp Leu Ala Ala Xaa Lys
1               5                   10

(2) INFORMATION FOR SEQ ID NO: 205:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 205:

Cys Thr Arg Ala Gln Phe Leu Lys Gly Cys
1               5                   10

(2) INFORMATION FOR SEQ ID NO: 206:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 206:

Cys Asn Ile Asn Gln Leu Arg Ser Ile Cys
1               5                   10

(2) INFORMATION FOR SEQ ID NO: 207:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 207:

Cys Asn Arg Ser Gln Leu Leu Ala Ala Cys
1               5                   10

(2) INFORMATION FOR SEQ ID NO: 208:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 208:

Cys Thr Ser Thr Gln Trp Leu Leu Ala Cys
1               5                   10

(2) INFORMATION FOR SEQ ID NO: 209:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 209:

Cys Gln Arg Ala Asp Leu Ile Asn Phe Cys
1               5                   10

(2) INFORMATION FOR SEQ ID NO: 210:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 210:

Cys Leu Leu Ser Glu Phe Leu Ala Gly Gln Gln Cys
1               5                   10

(2) INFORMATION FOR SEQ ID NO: 211:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 211:

Cys Thr Phe Gln Val Trp Lys Leu Ala Arg Asn Cys
1               5                   10

(2) INFORMATION FOR SEQ ID NO: 212:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 212:

Cys Thr Leu Gly Gln Trp Leu Gln Met Gly Met Cys
1               5                   10

(2) INFORMATION FOR SEQ ID NO: 213:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 213:

Cys Leu Thr Gly Pro Phe Val Thr Gln Trp Leu Tyr Glu Cys
1               5                   10

(2) INFORMATION FOR SEQ ID NO: 214:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 214:

Cys Thr Leu Arg Glu Phe Leu Asp Pro Thr Thr Ala Val Cys
1               5                   10

(2) INFORMATION FOR SEQ ID NO: 215:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 215:

Cys Gly Thr Glu Gly Pro Thr Leu Ser Thr Trp Leu Asp Cys
1               5                   10

(2) INFORMATION FOR SEQ ID NO: 216:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 216:

Cys Glu Leu Val Gly Pro Ser Leu Met Ser Trp Leu Thr Cys
1               5                   10

(2) INFORMATION FOR SEQ ID NO: 217:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 217:

Cys Ser Leu Lys Glu Phe Leu His Ser Gly Leu Met Gln Cys
1               5                   10

(2) INFORMATION FOR SEQ ID NO: 218:

(i) SEQUENCE CHARACTERISTICS:
           (A) LENGTH: 14 amino acids
           (B) TYPE: amino acid
           (C) STRANDEDNESS: <Unknown>
           (D) TOPOLOGY: linear (ii) MOLECULE TYPE: peptide (xi) SEQUENCE DESCRIPTION: SEQ ID NO: 218:

Cys Thr Leu Ala Glu Phe Leu Ala Ser Gly Val Glu Gln Cys
1               5                   10

(2) INFORMATION FOR SEQ ID NO: 219:

(i) SEQUENCE CHARACTERISTICS:
           (A) LENGTH: 14 amino acids
           (B) TYPE: amino acid
           (C) STRANDEDNESS: <Unknown>
           (D) TOPOLOGY: linear (ii) MOLECULE TYPE: peptide (xi) SEQUENCE DESCRIPTION: SEQ ID NO: 219:

Cys Thr Leu Lys Glu Trp Leu Val Ser His Glu Val Trp Cys
1               5                   10

(2) INFORMATION FOR SEQ ID NO: 220:

(i) SEQUENCE CHARACTERISTICS:
           (A) LENGTH: 16 amino acids
           (B) TYPE: amino acid
           (C) STRANDEDNESS: <Unknown>
           (D) TOPOLOGY: linear (ii) MOLECULE TYPE: peptide (xi) SEQUENCE DESCRIPTION: SEQ ID NO: 220:

Cys Ile Glu Gly Pro Thr Leu Arg Gln Trp Leu Ala Ala Arg Ala Cys
1               5                   10                  15

(2) INFORMATION FOR SEQ ID NO: 221:

(i) SEQUENCE CHARACTERISTICS:
           (A) LENGTH: 10 amino acids
           (B) TYPE: amino acid
           (C) STRANDEDNESS: <Unknown>
           (D) TOPOLOGY: linear (ii) MOLECULE TYPE: peptide (xi) SEQUENCE DESCRIPTION: SEQ ID NO: 221:

Arg Glu Gly Pro Thr Leu Arg Gln Trp Met
1               5                   10

(2) INFORMATION FOR SEQ ID NO: 222:

(i) SEQUENCE CHARACTERISTICS:
           (A) LENGTH: 14 amino acids
           (B) TYPE: amino acid
           (C) STRANDEDNESS: <Unknown>
           (D) TOPOLOGY: linear

```
    (ii) MOLECULE TYPE: peptide (xi) SEQUENCE DESCRIPTION: SEQ ID NO: 222:

Arg Glu Gly Pro Thr Leu Arg Gln Trp Leu Met Ser Arg Ser
  1               5                  10

(2) INFORMATION FOR SEQ ID NO: 223:

(i) SEQUENCE CHARACTERISTICS:
        (A) LENGTH: 92 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..63

(xi) SEQUENCE DESCRIPTION: SEQ ID NO: 223:

CTC GAG AGC GGG CAG GTG GTG CAT GGG GAG CAG GTG GGT GGT GAG GCC      48
Leu Glu Ser Gly Gln Val Val His Gly Glu Gln Val Gly Gly Glu Ala
  1               5                  10                  15

TCC GGA GGT GGT NNK TAACTAAGTA AAGCTGGCCA ATAAGTCGA                  92
Ser Gly Gly Gly Xaa
                20

(2) INFORMATION FOR SEQ ID NO: 224:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO: 224:

Leu Glu Ser Gly Gln Val Val His Gly Glu Gln Val Gly Gly Glu Ala
  1               5                  10                  15

Ser Gly Gly Gly Xaa
                20

(2) INFORMATION FOR SEQ ID NO: 225:

(i) SEQUENCE CHARACTERISTICS:
        (A) LENGTH: 122 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..120

(xi) SEQUENCE DESCRIPTION: SEQ ID NO: 225:

CAG ACT AAT TCG AGC TCG AAC AAC AAC AAT AAC AAT AAC AAC AAC          48
Gln Thr Asn Ser Ser Ser Asn Asn Asn Asn Asn Asn Asn Asn Asn
  1               5                  10                  15

CTC GGG ATC GAG GGA AGG ACC GGT CAC GTG GCC CGG GAA TTC GGA TCC      96
Leu Gly Ile Glu Gly Arg Thr Gly His Val Ala Arg Glu Phe Gly Ser
                 20                  25                  30

TCT AGA GTC GAC CTG CAG GCA AGC TT                                  122
Ser Arg Val Asp Leu Gln Ala Ser
                 35                  40
```

(2) INFORMATION FOR SEQ ID NO: 226:

(i) SEQUENCE CHARACTERISTICS:
        (A) LENGTH: 40 amino acids
        (B) TYPE: amino acid
        (D) TOPOLOGY: linear (ii) MOLECULE TYPE: protein (xi) SEQUENCE DESCRIPTION: SEQ ID NO: 226:

```
Gln Thr Asn Ser Ser Ser Asn Asn Asn Asn Asn Asn Asn Asn Asn
 1               5                  10                  15

Leu Gly Ile Glu Gly Arg Thr Gly His Val Ala Arg Glu Phe Gly Ser
                20                  25                  30

Ser Arg Val Asp Leu Gln Ala Ser
            35                  40
```

(2) INFORMATION FOR SEQ ID NO: 227:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..21

(xi) SEQUENCE DESCRIPTION: SEQ ID NO: 227:

```
GGA AGG ACC GGA GGT GGT NNK TAACTAAGTA AAGCTGGCCA ATAAGTCGAC         51
Gly Arg Thr Gly Gly Gly Xaa
 1               5
```

(2) INFORMATION FOR SEQ ID NO: 228:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO: 228:

```
Gly Arg Thr Gly Gly Gly Xaa
 1               5
```

(2) INFORMATION FOR SEQ ID NO: 229:

(i) SEQUENCE CHARACTERISTICS:
        (A) LENGTH: 93 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..84

(xi) SEQUENCE DESCRIPTION: SEQ ID NO: 229:

```
GAA GCG GCG ATG GCG GAG CTG AAT TAC ATT CCC CGG TCG CAG GAG GCC     48
Glu Ala Ala Met Ala Glu Leu Asn Tyr Ile Pro Arg Ser Gln Glu Ala
 1               5                  10                  15
```

-continued

```
TCC GGG GCC GTT AAC GGC CGT GGC CTA GCT GGC CAA TAAGTCGAC        93
Ser Gly Ala Val Asn Gly Arg Gly Leu Ala Gly Gln
            20                  25
```

(2) INFORMATION FOR SEQ ID NO: 230:

(i) SEQUENCE CHARACTERISTICS:
        (A) LENGTH: 28 amino acids
        (B) TYPE: amino acid
        (D) TOPOLOGY: linear (ii) MOLECULE TYPE: protein (xi) SEQUENCE DESCRIPTION: SEQ ID NO: 230:

```
Glu Ala Ala Met Ala Glu Leu Asn Tyr Ile Pro Arg Ser Gln Glu Ala
 1               5                  10                  15

Ser Gly Ala Val Asn Gly Arg Gly Leu Ala Gly Gln
            20                  25
```

(2) INFORMATION FOR SEQ ID NO: 231:

(i) SEQUENCE CHARACTERISTICS:
        (A) LENGTH: 126 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..96

(xi) SEQUENCE DESCRIPTION: SEQ ID NO: 231:

```
GAA GCG GCG ATG GCG GAG CTG AAT TAC ATT CCC CGG TCG CAG GAG GCC       48
Glu Ala Ala Met Ala Glu Leu Asn Tyr Ile Pro Arg Ser Gln Glu Ala
 1               5                  10                  15

TCC GGA GGT GGT NNK NNK NNK NNK NNK NNK NNK NNK NNK NNK NNK NNK       96
Ser Gly Gly Gly Xaa Xaa Xaa Xaa Xaa Xaa Xaa Xaa Xaa Xaa Xaa Xaa
            20                  25                  30

TAACTAAGTA AAGCTGGCCA ATAAGTCGAC                                      126
```

(2) INFORMATION FOR SEQ ID NO: 232:

(i) SEQUENCE CHARACTERISTICS:
        (A) LENGTH: 32 amino acids
        (B) TYPE: amino acid
        (D) TOPOLOGY: linear (ii) MOLECULE TYPE: protein (xi) SEQUENCE DESCRIPTION: SEQ ID NO: 232:

```
Glu Ala Ala Met Ala Glu Leu Asn Tyr Ile Pro Arg Ser Gln Glu Ala
 1               5                  10                  15

Ser Gly Gly Gly Xaa Xaa Xaa Xaa Xaa Xaa Xaa Xaa Xaa Xaa Xaa Xaa
            20                  25                  30
```

PEPTIDES AND COMPOUNDS THAT BIND TO A THROMBOPOIETIN RECEPTOR

CROSS-REFERENCE TO RELATED CASES

This application is being filed as a continuation of Ser. No. 08/973,225, which was filed Dec. 4, 1997 which is a 371 PCT/US96/09623 filed Jun. 7, 1996, which is a continuation of U.S. application Ser. No. 08/485,301 filed Jun. 7, 1995 (now abandoned) which is a continuation of U.S. application Ser. No. 08/478,128 filed Jun. 7, 1995 (now abandoned).

BACKGROUND OF THE INVENTION

The present invention provides peptides and compounds that bind to and activate the thrombopoietin receptor (c-mpl or TPO-R) or otherwise act as a TPO agonist. The invention has application in the fields of biochemistry and medicinal chemistry and particularly provides TPO agonists for use in the treatment of human disease.

Megakaryocytes are bone marrow-derived cells, which are responsible for producing circulating blood platelets. Although comprising <0.25% of the bone marrow cells in most species, they have >10 times the volume of typical marrow cells. See Kuter et. al. *Proc. Natl. Acad. Sci. USA* 91:11104–11108 (1994). Megakaryocytes undergo a process known as endomitosis whereby they replicate their nuclei but fail to undergo cell division and thereby give rise to polyploid cells. In response to a decreased platelet count, the endomitotic rate increases, higher ploidy megakaryocytes are formed, and the number of megakaryocytes may increase up to 3-fold. See Harker *J. Clin. Invest.* 47:458–465 (1968). In contrast, in response to an elevated platelet count, the endomitotic rate decreases, lower ploidy megakaryocytes are formed, and the number of megakaryocytes may decrease by 50%.

The exact physiological feedback mechanism by which the mass of circulating platelets regulates the endomitotic rate and number of bone marrow megakaryocytes is not known. The circulating thrombopoietic factor involved in mediating this feedback loop is now thought to be thrombopoietin (TPO). More specifically, TPO has been shown to be the main humoral regulator in situations involving thrombocytopenia. See, e.g., Metcalf *Nature* 369:519–520 (1994). TPO has been shown in several studies to increase platelet counts, increase platelet size, and increase isotope incorporation into platelets of recipient animals. Specifically, TPO is thought to affect megakaryocytopoiesis in several ways: (1) it produces increases in megakaryocyte size and number; (2) it produces an increase in DNA content, in the form of polyploidy, in megakaryocytes; (3) it increases megakaryocyte endomitosis; (4) it produces increased maturation of megakaryocytes; and (5) it produces an increase in the percentage of precursor cells, in the form of small acetylcholinesterase-positive cells, in the bone marrow.

Because platelets (thrombocytes) are necessary for blood clotting and when their numbers are very low a patient is at serious risk of death from catastrophic hemorrhage, TPO has Potential useful application in both the diagnosis and the treatment of various hematological disorders, for example, diseases primarily due to platelet defects. Ongoing clinical trials with TPO have indicated that TPO can be administered safely to patients. in addition, recent studies have provided a basis for the projection of efficacy of TPO therapy in the treatment of thrombocytopenia, and particularly thrombocytopenia resulting from chemotherapy, radiation therapy, or bone marrow transplantation as treatment for cancer or lymphoma. See, e.g., McDonald (1992) *Am. J. Ped. Hematology/Oncology* 14:8–21 (1992).

The gene encoding TPO has been cloned and characterized. See Kuter et al. *Proc. Natl. Acad. Sci. USA* 91:11104–11108 (1994); Barley et al. *Cell* 77:1117–1124 (1994) ; Kaushansky et al. *Nature* 369:568–571 (1994); Wendling et al. *Nature* 369:571–574 (1994); and Sauvage et al. *Nature* 369:533–538 (1994). Thrombopoietin is a glycoprotein with at least two forms, with apparent molecular masses of 25 kDa and 31 kDa, with a common N-terminal amino acid sequence. See, Bartley et al. *Cell* 77:1117–1124 (1994). Thrombopoietin appears to have two distinct regions separated by a potential Arg-Arg cleavage site. The amino-terminal region is highly conserved in man and mouse, and has some homology with erythropoietin and interferon-a and interferon-b. The carboxy-terminal region shows wide species divergence.

The DNA sequences and encoded peptide sequences for human TPO-R (also known as c-mpl) have been described. See Vigon et al. *Proc. Natl. Acad. Sci. USA* 89:5640–5644 (1992). TPO-R is a member of the haematopoietin growth factor receptor family, a family characterized by a common structural design of the extracellular domain, including four conserved C residues in the N-terminal portion and a WSXWS motif (SEQ ID NO:1) close to the transmembrane region. See Bazan *Proc. Natl. Acad. Sci. USA* 87:6934–6938 (1990). Evidence that this receptor plays a functional role in hematopoiesis includes observations that its expression is restricted to spleen, bone marrow, or fetal liver in mice (see Souyri et al. *Cell* 63:1137–1147 (1990)) and to megakaryocytes, platelets, and $CD34^+$ cells in humans (see Methia et al. *Blood* 82:1395–1401 (1993)). Furthermore, exposure of $CD34^+$ cells to synthetic oligonucleotides antisense to mpl RNA significantly inhibits the appearance of megakaryocyte colonies without affecting erythroid or myeloic colony formation. Some workers postulate that the receptor functions as a homodimer, similar to the situation with the receptors for G-CSF and erythropoietin.

The availability of cloned genes for TPO-R facilitates the search for agonists of this important receptor. The availability of the recombinant receptor protein allows the study of receptor-ligand interaction in a variety of random and semi-random peptide diversity generation systems. These systems include the "peptides on plasmids" system described in U.S. Pat. Nos. 5,270,170 and 5,338,665; the "peptides on phase" system described in U.S. patent application Ser. No. 07/718,577, filed Jun. 20, 1991, U.S. patent application Ser. No. 07/541,108, filed Jun. 20, 1990, and in Cwirla et al., *Proc. Natl. Acad. Sci. USA* 87:6378–6382 (1990); the "polysome" system described in U.S. patent application Ser. No. 08/300,262, filed Sep. 2, 1994, which is a continuation-in-part application based on U.S. patent application Ser. No. 08/144,775, filed Oct. 29, 1993 and PCT WO 95/11992; the "encoded synthetic library" system described in U.S. patent application Ser. No. 08/146,886, filed Nov. 12, 1993, Ser. No. 07/946,239, filed Sep. 16, 1992, and Ser. No. 07/762,522, filed Sep. 18, 1991; and the "very large scale immobilized polymer synthesis" system described in U.S. Pat. No. 5,143,854, PCT Patent Publication No. 90/15070, published Dec. 13, 1990; U.S. patent application Ser. No. 07/624,120, filed Dec. 6, 1990; Fodor et al. *Science* 251:767–773 (February/1991); Dower and Fodor *Ann. Rep. Med. Chem.* 26:271–180 (1991); and U.S. patent application Ser. No. 07/805,727, filed Dec. 6, 1991; each of the foregoing patent applications and publications is incorporated herein by reference.

The slow recovery of platelet levels in patients suffering from thrombocytopenia is a serious problem, and has lent urgency to the-search for a blood growth factor agonist able to accelerate platelet regeneration. The present invention provides such an agonist.

SUMMARY OF THE INVENTION

This invention is directed, in part, to the novel and unexpected discovery that defined low molecular weight peptides and peptide mimetics have strong binding properties to the TPO-R and can activate the TPO-R. Accordingly, such peptides and peptide mimetics are useful for therapeutic purposes in treating conditions mediated by TPO (e.g., thrombocytopenia resulting from chemotherapy, radiation therapy, or bone marrow transfusions) as well as for diagnostic purposes in studying the mechanism of hematopoiesis and for the in vitro expansion of megakaroycytes and committed progenitor cells.

Peptides and peptide mimetics suitable for therapeutic and/or diagnostic purposes have an $IC_{50}$ of about 2 mM or less, as determined by the binding affinity assay set forth in Example 3 below wherein a lower $IC_{50}$ correlates to a stronger binding affinity to TPO-R. For pharmaceutical purposes, the peptides and peptidomimetics preferably have an $IC_{50}$ of no more than about 100 µm, more preferably, no more than 500 nM. In a preferred embodiment, the molecular weight of the peptide or peptide mimetic is from about 250 to about 8000 daltons.

When used for diagnostic purposes, the peptides and peptide mimetics preferably are labeled with detectable label and, accordingly, the peptides and peptide mimetics without such a label serve as intermediates in the preparation of labeled peptides and peptide mimetics.

Peptides meeting the defined criteria for molecular weight and binding affinity for TPO-R comprise 9 or more amino acids wherein the amino acids are naturally occurring or synthetic (non-naturally occurring) amino acids. Peptide mimetics include peptides having one or more of the following modifications:

peptides wherein one or more of the peptidyl [—C(O)NR—] linkages (bonds) have been replaced by a non-peptidyl linkage such as a —CH$_2$-carbamate linkage [—CH$_2$—OC(O)NR—]; a phosphonate linkage; a —CH$_2$-sulfonamide [—CH$_2$—S(O)$_2$NR—] linkage; a urea [—NHC(O)NH—] linkage; a —CH$_2$-secondary amine linkage; or an alkylated peptidyl linkage [—C(O)NR$^6$— where R$^6$ is lower alkyl];

peptides wherein the N-terminus is derivatized to a —NRR$^1$ group; to a —NRC(O)R group; to a —NRC(O)OR group; to a —NRS(O)$_2$R group; to a —NHC(O)NHR group where R and R$^1$ are hydrogen or lower alkyl with the proviso that R and R$^1$ are not both hydrogen; to a succinimide group; to a benzyloxycarbonyl-NH—(CBZ—NH—) group; or to a benzyloxycarbonyl-NH— group having from 1 to 3 substituents on the phenyl ring selected from the group consistent of lower alkyl, lower alkoxy, chloro, and bromo; or peptides wherein the C terminus is derivatized to —C(O)R$^2$ where $^2$ is selected from the group consisting of lower alkoxy, and —NR$^3$R$^4$ where R$^3$ and R$^4$ are independently selected from the group consisting of hydrogen and lower alkyl.

Accordingly, preferred peptides and peptide mimetics comprise a compound having:

(1) a molecular weight of less than about 5000 daltons, and (2) a binding affinity to TPO-R as expressed by an $IC_{50}$ of no more than about 100 µm, wherein from zero to all of the —C(O)NH— linkages of the peptide have been replaced by a linkage selected from the group consisting of a —CH$_2$OC(O)NR— linkage; a phosphonate linkage; a —CH$_2$S(O)$_2$NR— linkage; a —CH$_2$NR— linkage; and a —C(O)NR$^6$— linkage; and a —NHC(O)NH— linkage where R is hydrogen or lower alkyl and R$^6$ is lower alkyl, further wherein the N-terminus of said peptide or peptide mimetic is selected from the group consisting of a —NRR$^1$ group; a —NRC(O)R group; a —NRC(O)OR group; a —NRS(O)$_2$R group; a —NHC(O)NHR group; a succinimide group; a benzyloxycarbonyl-NH— group; and a benzyloxycarbonyl-NH— group having from 1 to 3 substituents on the phenyl ring selected from the group consisting of lower alkyl, lower alkoxy, chloro, and bromo, where R and R$^1$ are independently selected from the group consisting of hydrogen and lower alkyl, and still further wherein the C-terminus of said peptide or peptide mimetic has the formula —C(O)R$^2$ where R$^2$ is selected from the group consisting of hydroxy, lower alkoxy, and —NR$^3$R$^4$ where R$^3$ and R$^4$ are independently selected from the group consisting of hydrogen and lower alkyl and where the nitrogen atom of the —NR$^3$R$^4$ group can optionally be the amine group of the N-terminus of the peptide so as to form a cyclic peptide, and physiologically acceptable salts thereof.

In a related embodiment, the invention is directed to a labeled peptide or peptide mimetic comprising a peptide or peptide mimetic described as above having covalently attached thereto a label capable of detection.

In some embodiments of the invention, preferred peptides for use include peptides having a core structure comprising a sequence of amino acids (SEQ ID NO:2):

$X_1$ $X_2$ $X_3$ $X_4$ $X_5$ $X_6$ $X_7$ where $X_1$ is C, L, M, P, Q, V; $X_2$ is F, K, L, N, Q, R, S, T or V; $X_3$ is C, F, I, L, M, R, S, V or W; $X_4$ is any of the 20 genetically coded L-amino acids; $X_5$ is A, D, E, G, K, M, Q, R, S, T, V or Y; $X_6$ is C, F, G, L, M, S, V, W or Y; and $X_7$ is C, G, I, K, L, M, N, R or V.

In a preferred embodiment the core peptide comprises a sequence of amino acids (SEQ ID NO:3):

$X_8$ G $X_1$ $X_2$ $X_3$ $X_4$$X_5$ W $X_7$ where $X_1$ is L, M, P, Q, or V; $X_2$ is F, R, S, or T; $X_3$ is F, L, V, or W; $X_4$ is A, K, L, M, R, S, V, or T; $X_5$ is A, E, G, K, M, Q, R, S, or T; $X_7$ is C, I, K, L, M or V; and each $X_8$ residue is independently selected from any of the 20 genetically coded L-amino acids, their stereoisomeric D-amino acids; and non-natural amino acids. Preferably, each $X_8$ residue is independently selected from any of the 20 genetically coded L-amino acids and their stereoisomeric D-amino acids. In a preferred embodiment (SEQ ID NO:4), $X_1$ is P; $X_2$ is T; $X_3$ is L; $X_4$ is R; $X_5$ is E or Q; and $X_7$ is I or L.

More preferably, the core peptide comprises a sequence of amino acids (SEQ ID NO:5):

$X_9$ $X_8$ G $X_1$ $X_2$ $X_3$ $X_4$ $X_5$ W $X_7$ where $X_9$ is A, C, E, G, I, L, M, P, R, Q, S, T, or V; and $X_9$ is A, C, D, E, K, L, Q, R, S, T, or V. More preferably, $X_9$ is A or I; and $X_8$ is D, E, or K.

Particularly preferred peptides include: (SEQ ID NO:6-13, respectively) G G C A D G P T L R E W I S F C G G; G N A D G P T L R Q W L E G R R P K N; G G C A D G P T L R E W I S F C G G K; T I K G P T L R Q W L K S R E H T S; S I E G P T L R E W L T S R T P H S; L A I E G P T L R Q W L H G N G R D T; C A D G P T L R E W I S F C; and I E G P T L R Q W L A A R A.

In further embodiments of the invention, preferred peptides for use in this invention include peptides having a core structure comprising a sequence of amino acids (SEQ ID NO:14):

C $X_2$ $X_3$ $X_4$ $X_5$ $X_6$ $X_7$ where $X_2$ is K, L, N, Q, R, S, T or V; $X_3$ is C, F, I, L, M, R, S or V; $X_4$ is any of the 20 genetically coded L-amino acids; $X_5$ is A, D, E, G, S, V or Y; $X_6$ is C, F, G, L, M, S, V, W or Y; and $X_7$ is C, G, I, K, L, M, N, R or V. In a more preferred embodiment, $X_4$ is A, E, G, H, K, L, M, P, Q, R, S, T, or W. In a further embodiment, $X_2$ is S or T; $X_3$ is L or R; $X_4$ is R; $X_5$ is D, E, or G; $X_6$ is F, L, or W; and $X_7$ is I, K, L, R, or V. Particularly preferred peptides include (SEQ ID NO:15): G G C T L R E W L H G G F C G G.

In a further embodiment, preferred peptides for use in this invention include peptides having a structure comprising a sequence of amino acids (SEQ ID NO:16):

$X_8$ C $X_2$ $X_3$ $X_4$ $X_5$ $X_6$ $X_7$ where $X_2$ is F, K, L, N, Q, R, S, T or V; $X_3$ is C, F, I, L, M, R, S, V or W; $X_4$ is any of the 20 genetically coded L-amino acids; $X_5$ is A, D, A, G, K, M, Q, R, S, T, V or Y; $X_6$ is C, F, G, L, M, S, V, W or Y; $X_7$ is C, G, I, K, L, M, N, R or V; and $X_8$ is any of the 20 genetically coded L-amino acids. In some embodiments, $X_8$ is preferably G, S, Y, or R.

The compounds described herein are useful for the prevention and treatment of diseases mediated by TPO, and particularly for treating hematological disorders, including but not limited to, thrombocytopenia resulting from chemotherapy, radiation therapy, or bone marrow transfusions. Thus, the present invention also provides a method for treating wherein a patient having a disorder that is susceptible to treatment with a TPO agonist receives, or is administered, a therapeutically effective dose or amount of a compound of the present invention.

The invention also provides for pharmaceutical compositions comprising one or more of the compounds described herein ana a physiologically acceptable carrier. These pharmaceutical compositions can be in a variety of forms including oral dosage forms, as well as inhalable powders and solutions and injectable and infusible solutions.

BRIEF DESCRIPTION OF THE FIGURES

FIG. 1A is a graphical depiction of the results of the TPO-R transfected Ba/F3 cell proliferation assay for selected peptides of the invention:

- ■ designating the results for (SEQ ID NO:8) G G C A D G P T L R E W I S F C G G K (biotin);
- × designating the results for (SEQ ID NO:6) G G C A D G P T L R E W I S F C G G;
- ▲ designating the results for (SEQ ID NO:11) L A I E G P T L R Q W L H G N G R D T;
- ○ designating the results for (SEQ ID NO:7) G N A D G P T L R Q W L E G R R P K N; and
- + designating the results for (SEQ ID NO:9) T I K G P T L R Q W L K S R E H T S.

Figure 1A:
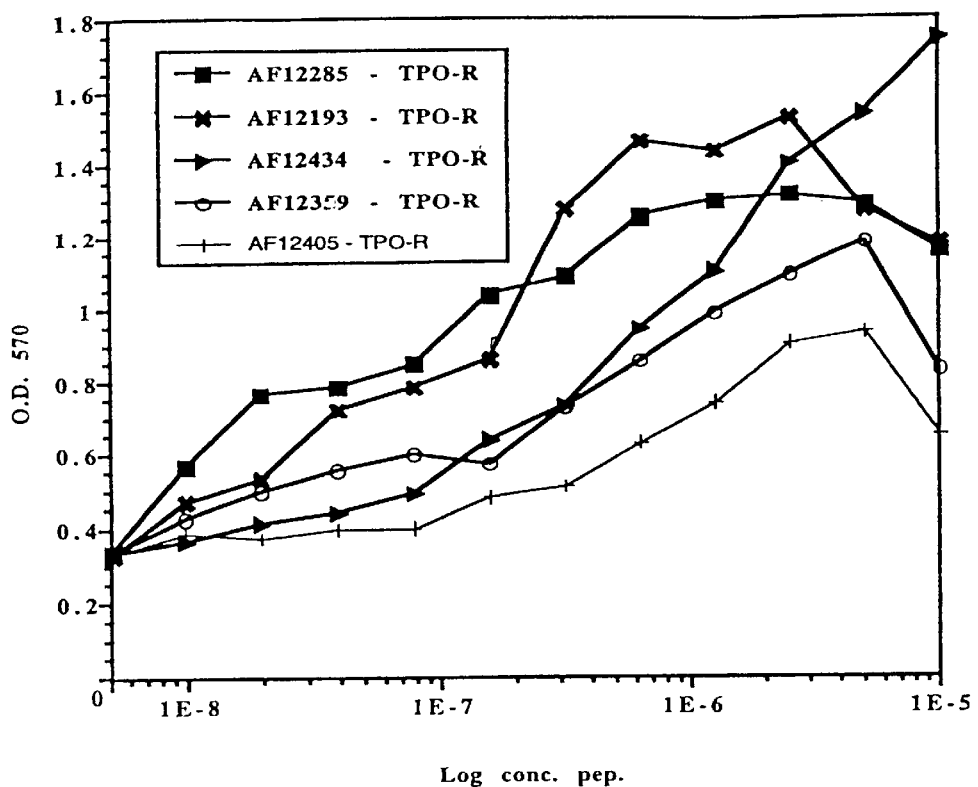
FIGS. 1A–B illustrates the results of a functional assay in the presence of various peptides; the assay is described in Example 2.
Figure 1B:
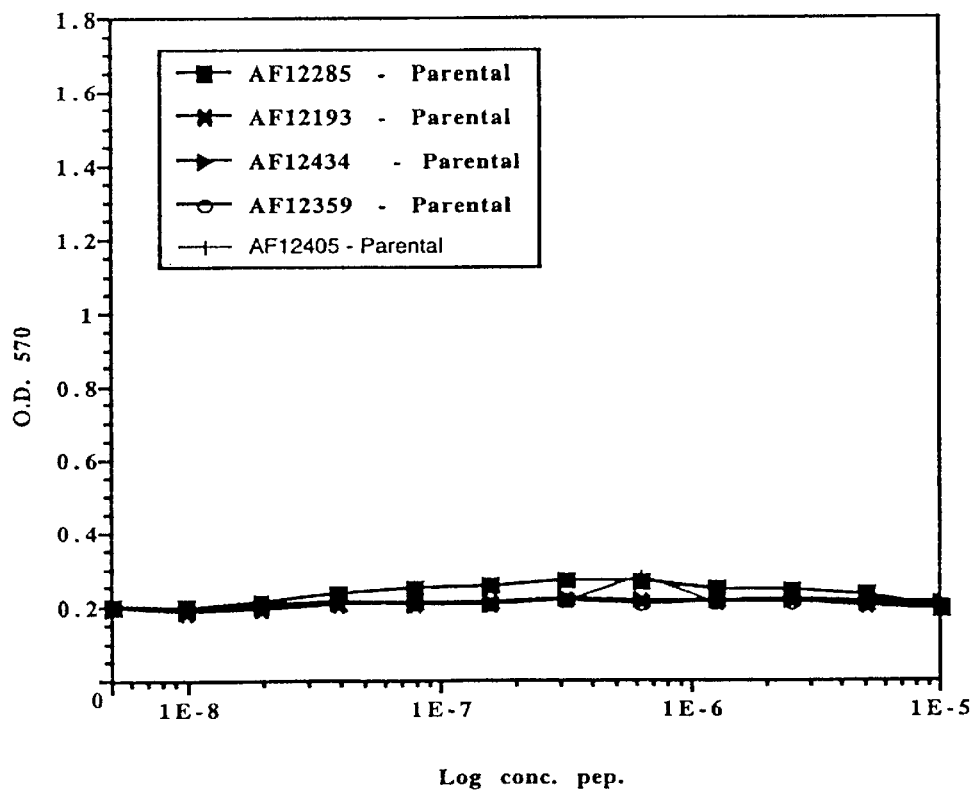

FIG. 1B is a graphical depiction of the results with the same peptides and the parental cell line.

Figure 2A:
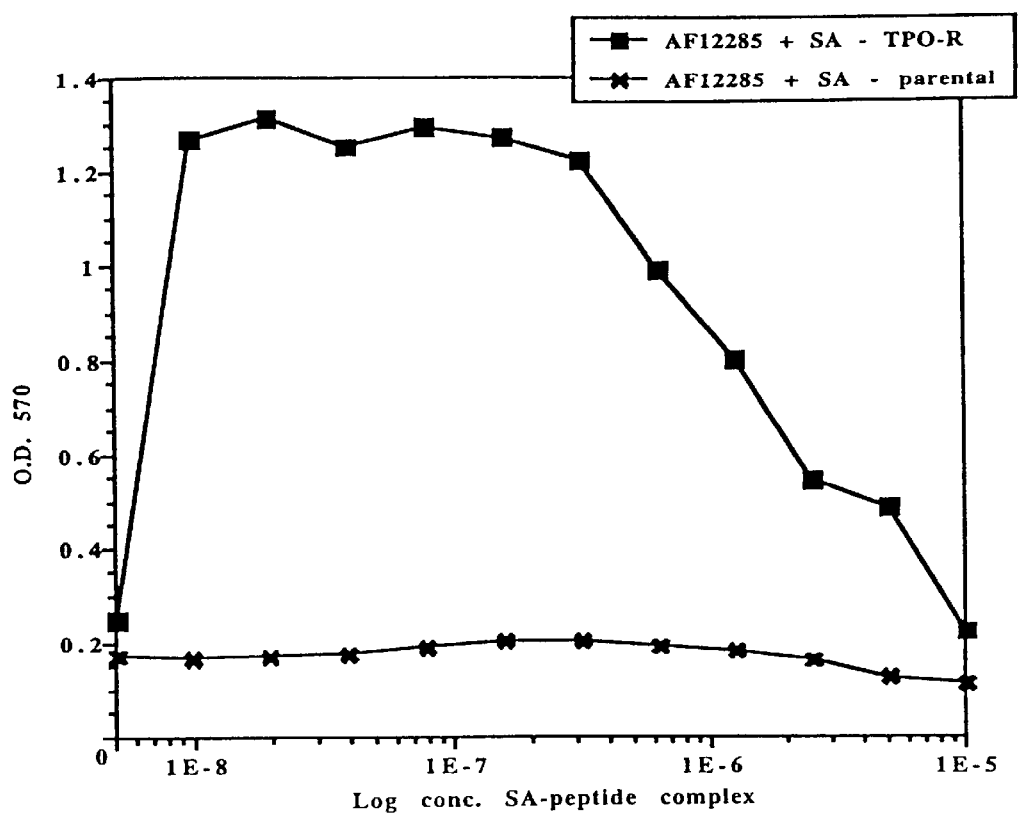
Figure 2B:
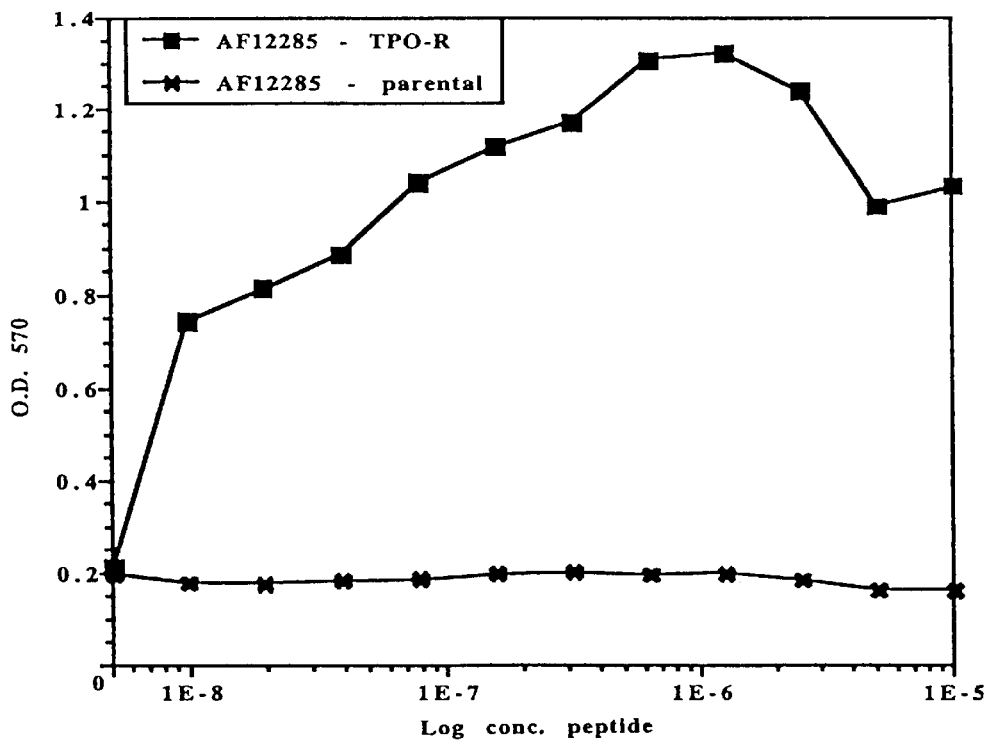
Figure 2C:
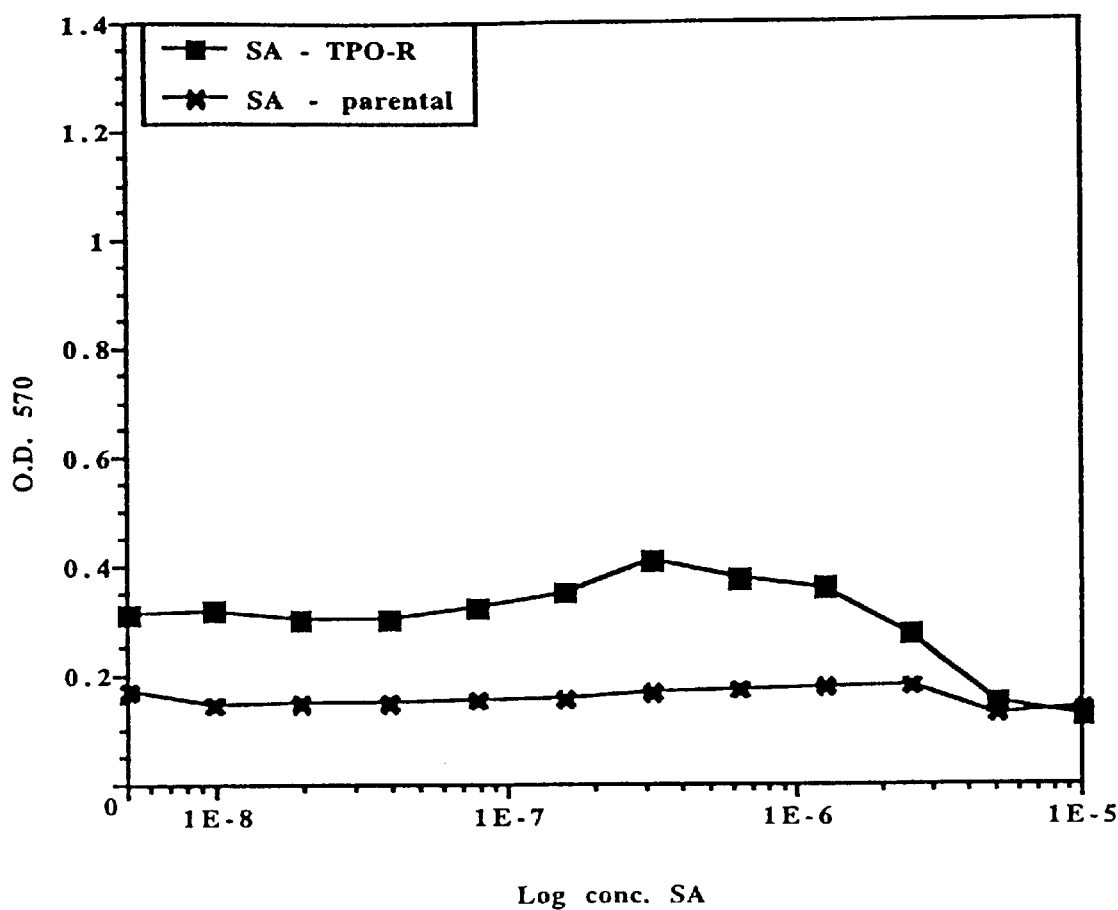

FIGS. 2A–C show the results of peptide oligomerization using the TPO-R transfected Ba/F3 cell proliferation assay. FIG. 2A shows the results of the assay for the complexed biotinylated peptide (AF 12285 with streptavidin (SA)) for both the transfected and parental cell lines. FIG. 2B shows the results of the assay for the free biotinylated peptide (AF 12285) for both the transfected and parental cell lines. FIG. 2C shows the results of the assay for streptavidin alone for both the transfected and parental cell lines.

Figure 3A:
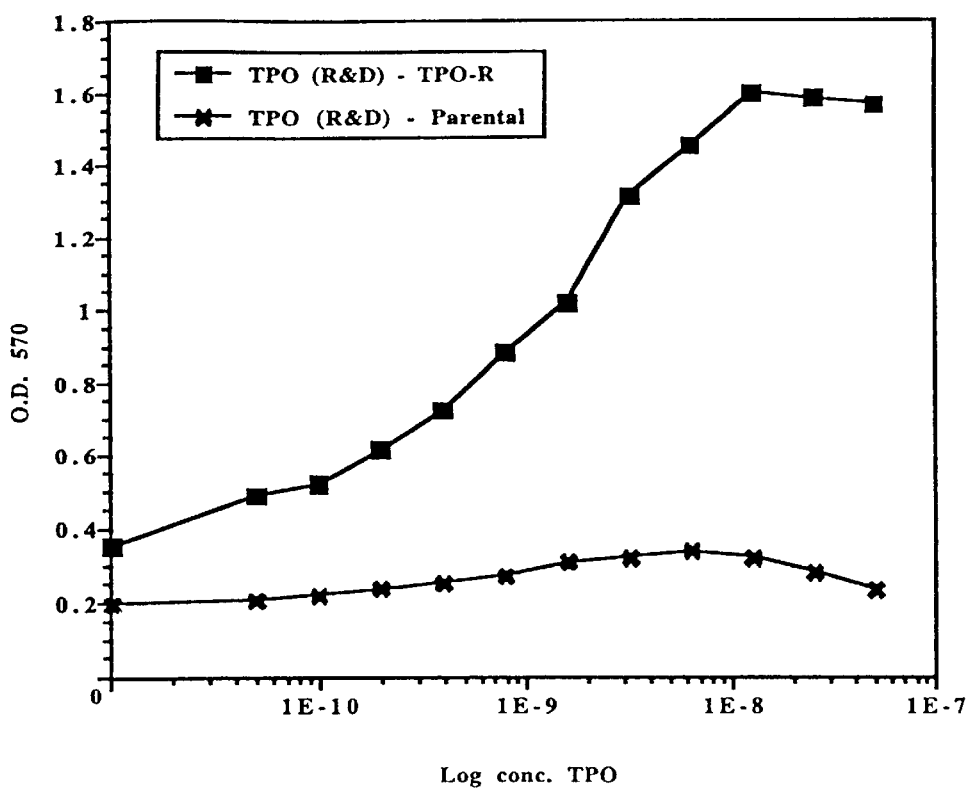
Figure 3B:
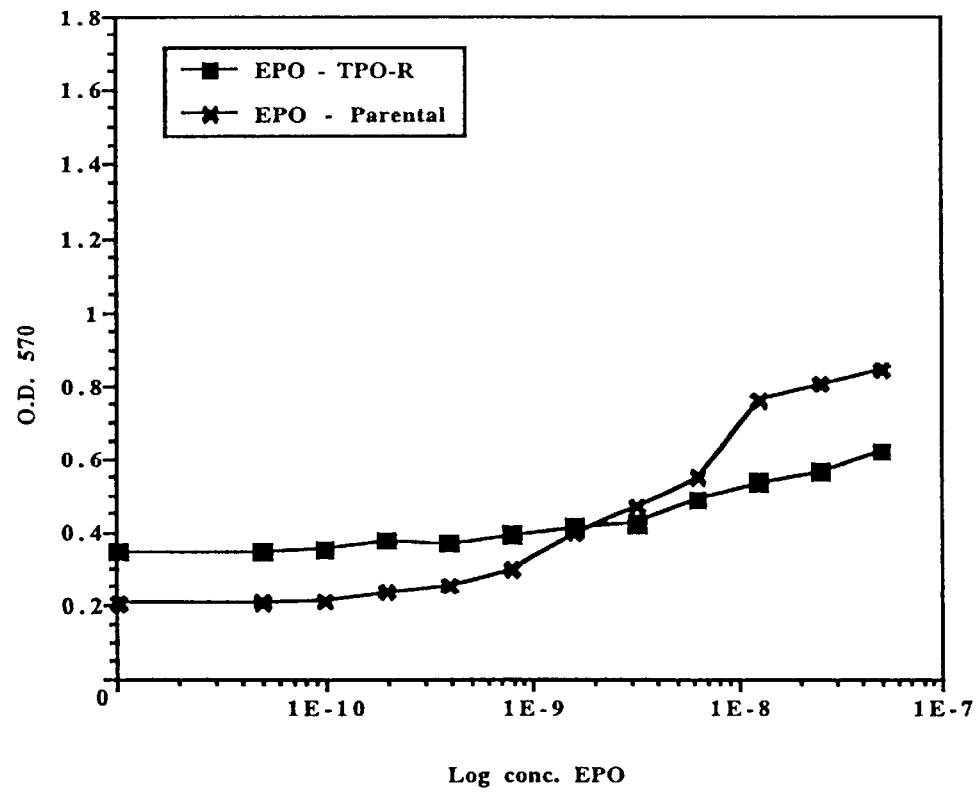
Figure 3C:
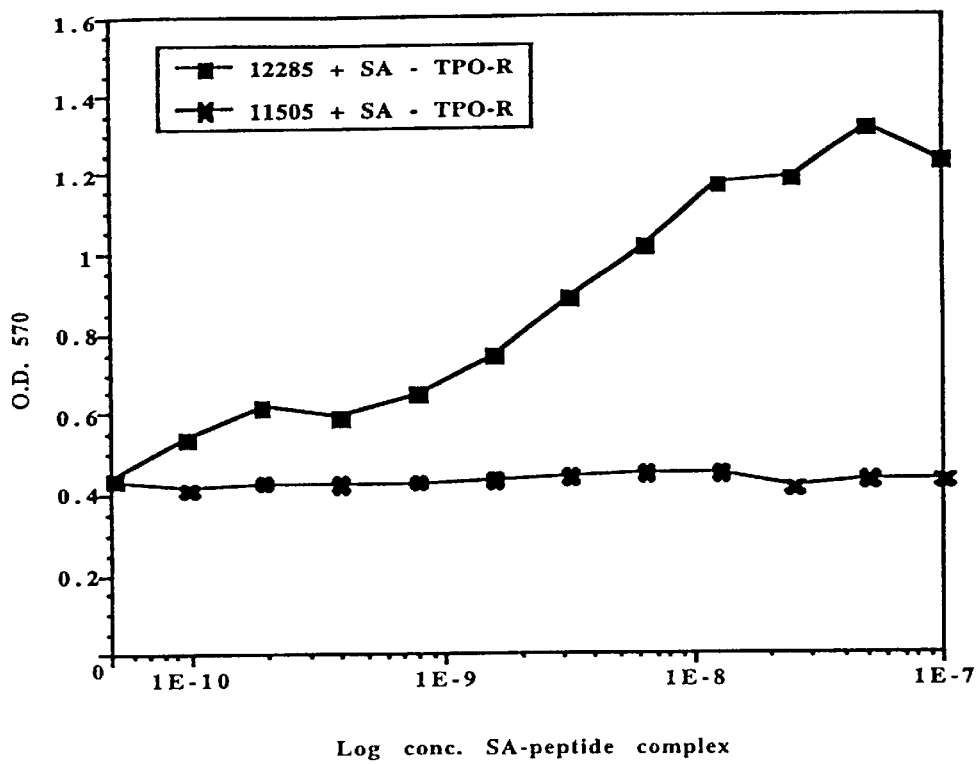
Figure 3D:
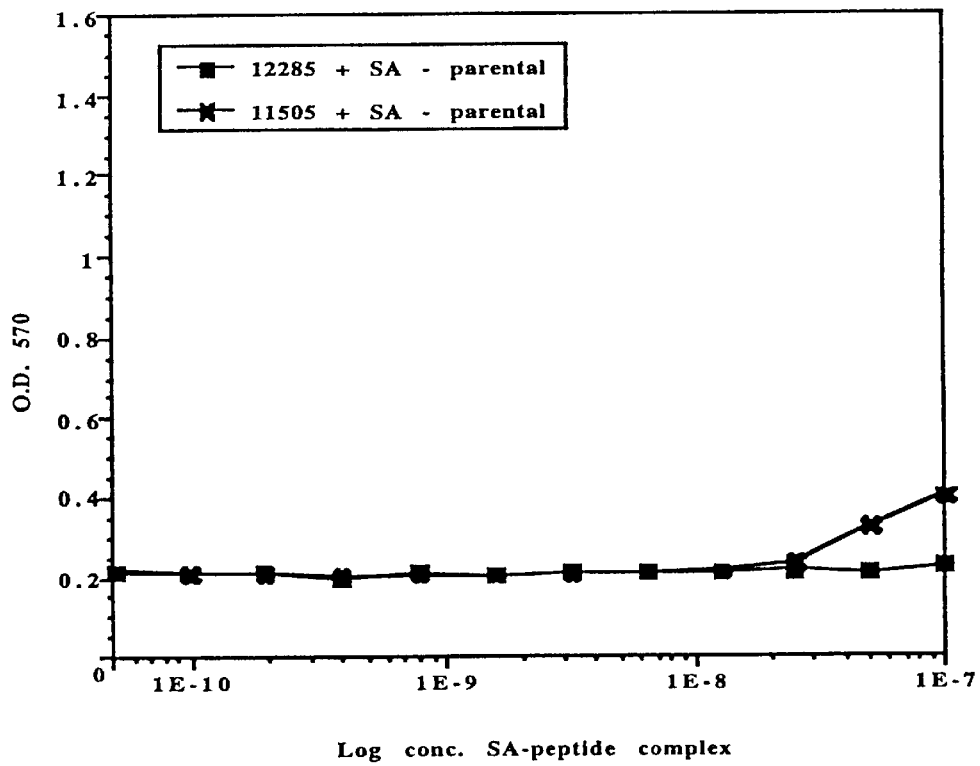
Figure 3E:
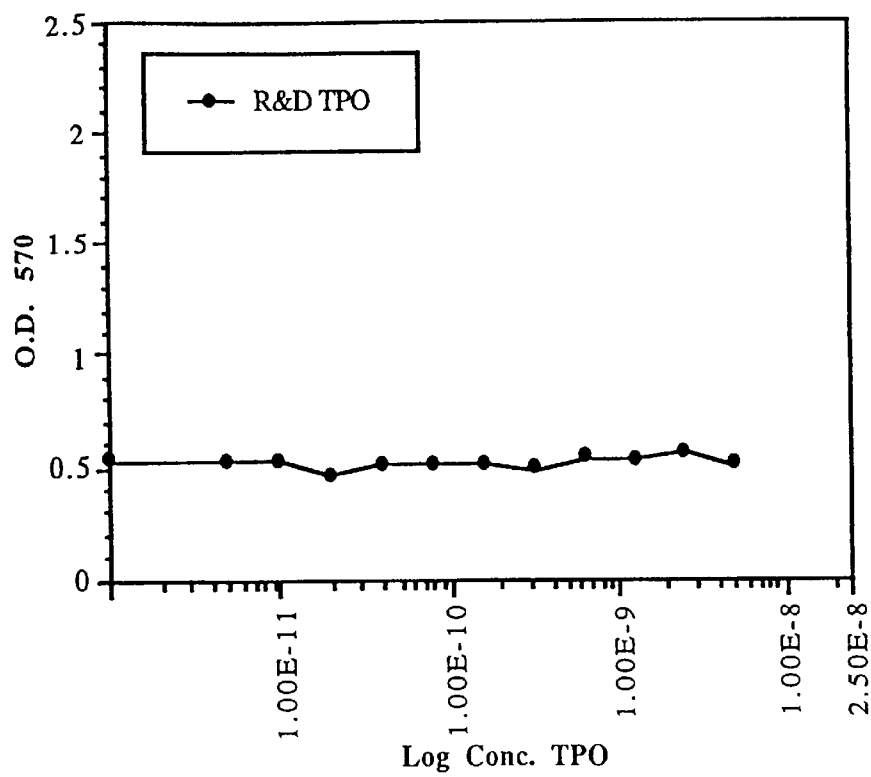
Figure 3F:
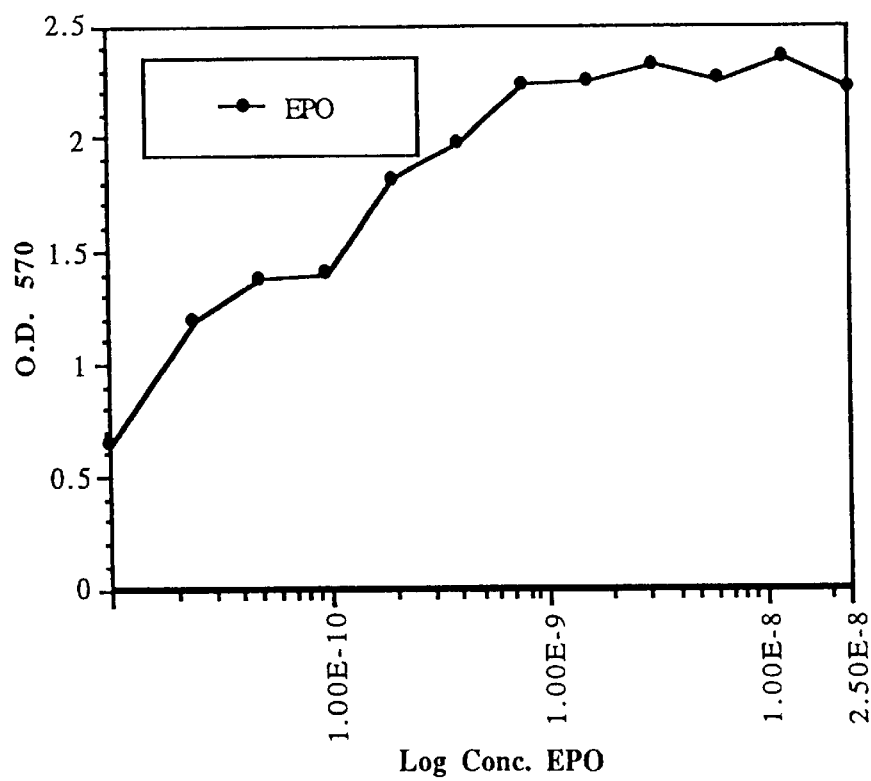
Figure 3G:
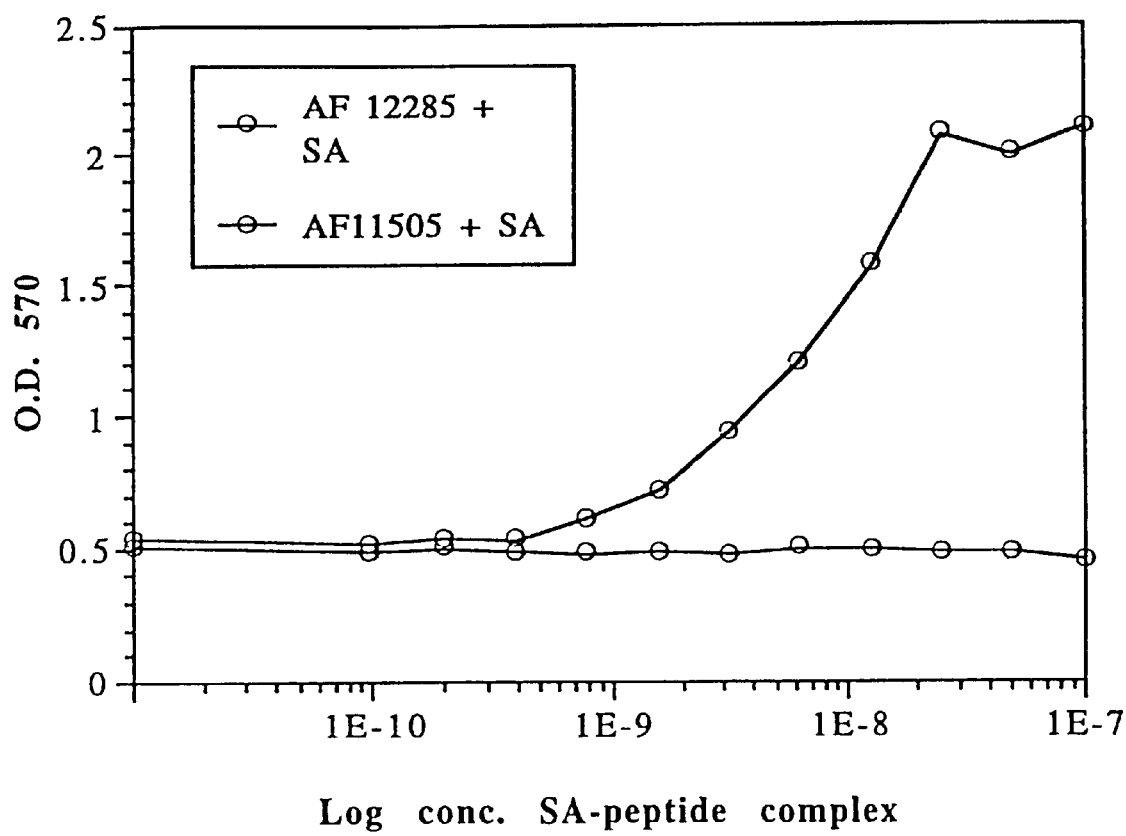

FIGS. 3A–G show the results of a series of control experiments showing the activity of TPO, the peptides of the present invention, EPO, and EPO-R binding peptides in a cell proliferation assay using either the TPO-R transfected Ba/F3 cell line and its corresponding parental line, or an EPO-dependent cell line. FIG. 3A depicts the results for TPO in the cell proliferation assay using the TPO-R transfected Ba/F3 cell line and its corresponding parental line. FIG. 3B depicts the results for EPO in the cell proliferation assay using the TPO-R transfected Ba/F3 cell line and its corresponding parental line. FIG. 3C depicts the results for complexed biotinylated peptide (AF 12285 with streptavidin (SA)) and a complexed form of a biotinylated EPO-R binding peptide (AF 11505 with SA) in the TPO-R transfected Ba/F3 cell line. The results for the corresponding parental cell line are shown in FIG. 3D. FIG. 3E depicts the results for TPO in the cell proliferation assay using the EPO-dependent cell line. FIG. 3F depicts the-results for EPO in the cell proliferation assay using the EPO-dependent cell line. FIG. 3G depicts the results for complexed biotinylated peptide (AF 12885 with streptavidin (SA)) and the complexed form of a biotinylated EPO-R binding peptide (AF 11505 with SA) in the EPO-dependent cell line.

Figure 4A:
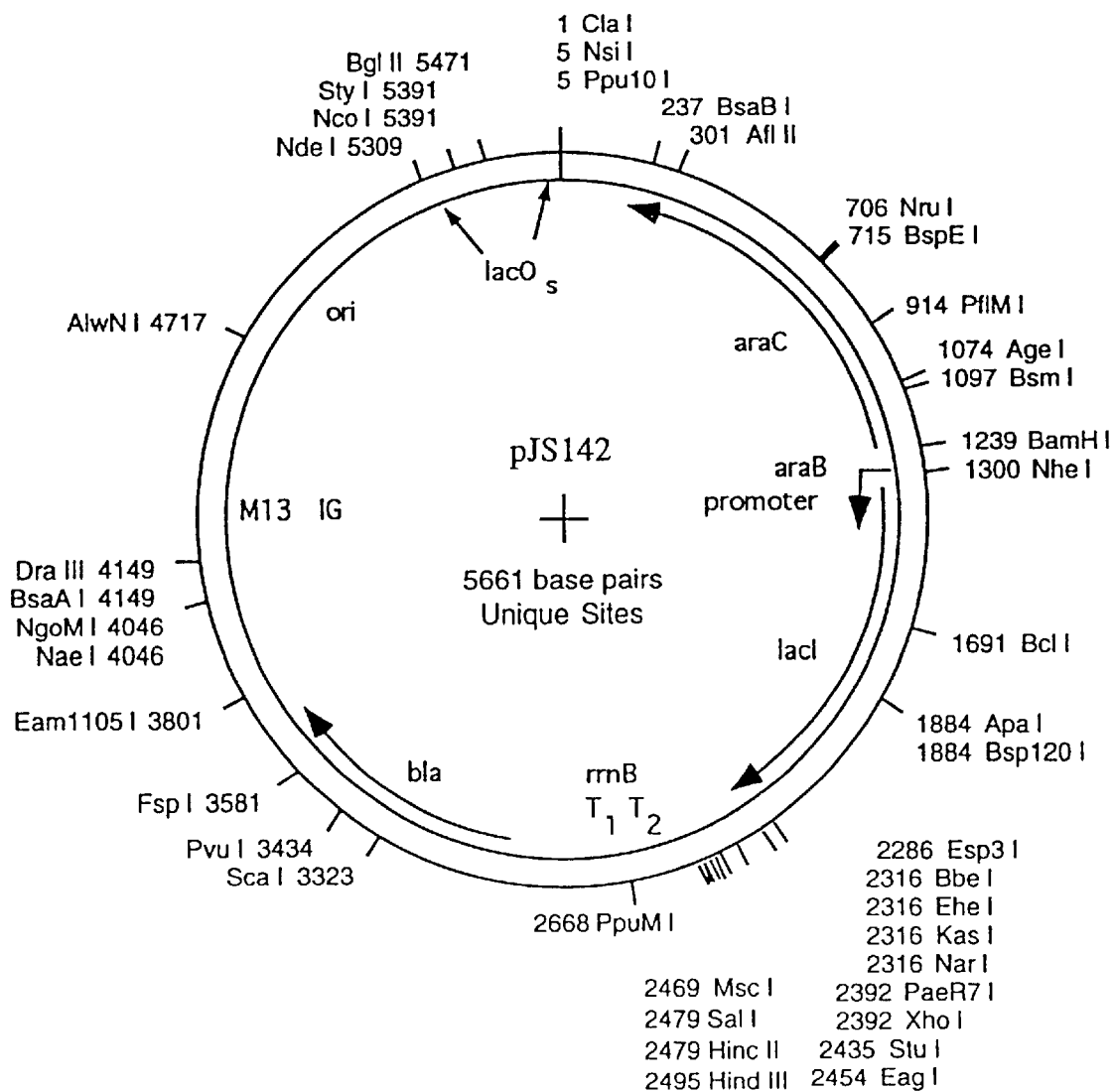

FIGS. 4A–C illustrates the construction of peptides-on-plasmids libraries in vector pJS142. FIG. 4A shows a restriction map and position of the genes. The library plasmid includes the rrnB transcriptional terminator, the bla gene to permit selection on ampicillin, the M13 phage intragenic region (M13 IG) to permit rescue of single-stranded DNA, a plasmid replication origin (ori), two lacO$_s$ sequences, and the araC gene to permit positive and negative regulation of the arab promoter driving expression of the lac fusion gene. FIG. 4B (SEQ ID NOS 19 & 20, respectively) shows the sequence of the cloning region at the 3' end of the lac I gene, including the SfiI and EagI sites used during library construction. FIG. 4C (SEQ ID NOS 223 & 224, respectively) shows the ligation of annealed library oligonucleotides, ON-829 and ON-830, to SfiI sites of pJS142 to produce a library. Single spaces in the sequence indicate sites of ligation.

FIGS. 5A–B illustrate cloning into the pELM3 and pELM15 MBP vectors. FIG. 5A (SEQ ID NOS 225 & 226, respectively) shows the sequence at the 3' end of the malE fusion gene, including the MBP coding sequence, the poly asparagine linker, the factor Xa protease cleavagge site, and the available cloning sites. The remaining portions of the vectors are derived from pMALc2 (pELM3) and pMALp2 (pELM15), available from New England Biolabs. FIG. 5B (SEQ ID NOS 227 & 228, respectively) shows the sequence of the vectors after transfer of the BspEII-ScaI library fragment into AgeI-scaI digested pELM3/pELM15. The transferred sequence includes the sequence encoding the GGG peptide linker from the pJS142 library.

Figure 6A:
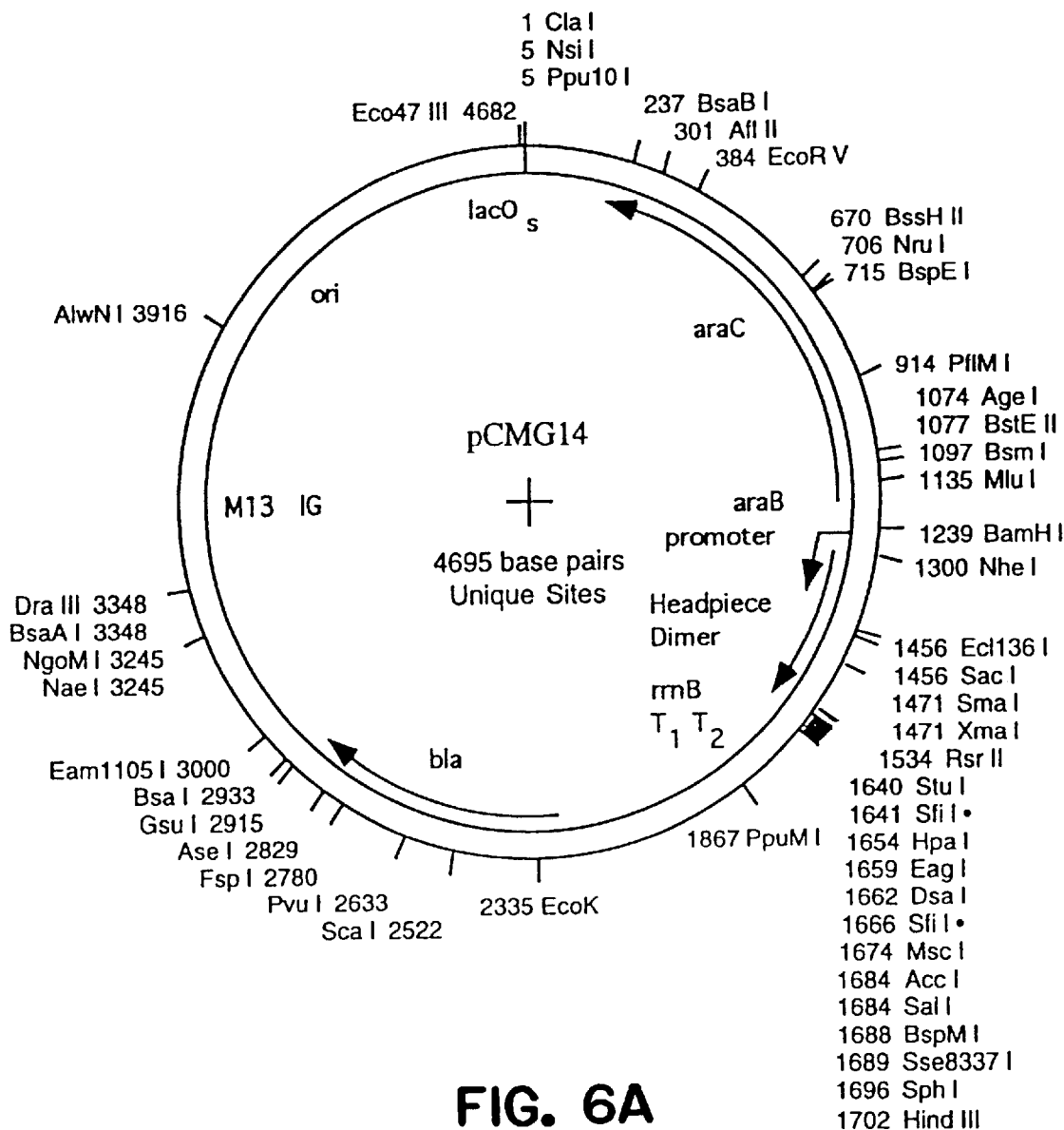

FIG. 6A depicts a restriction map and position of the genes for the construction of headpiece dimer libraries in vector pCMG14. The library plasmid includes: the rrnB transcriptional terminator, the bla gene to permit selection on ampicillin, the M13 phage intragenic region (M13 IG) to permit rescue of single-stranded DNA, a plasmid replication origin (ori), one lacO$_s$ sequence, and the araC gene to permit positive and negative regulation of the araB promoter driving expression of the headpiece dimer fusion gene. FIG. 6B (SEQ ID NOS 229 & 230, respectively) depicts the sequence of the cloning region at the 3' end of the headpiece dimer gene, including the SfiI and EagI sites used during library construction. FIG. 6C (SEQ ID NOS 231 & 232, respectively) shows the ligation of annealed ON-1679, ON-829, and ON-830 to SfiI sites of pCMG14 to produce a library. Singles spaces in the sequence indicate sites of ligation.

Figure 7:
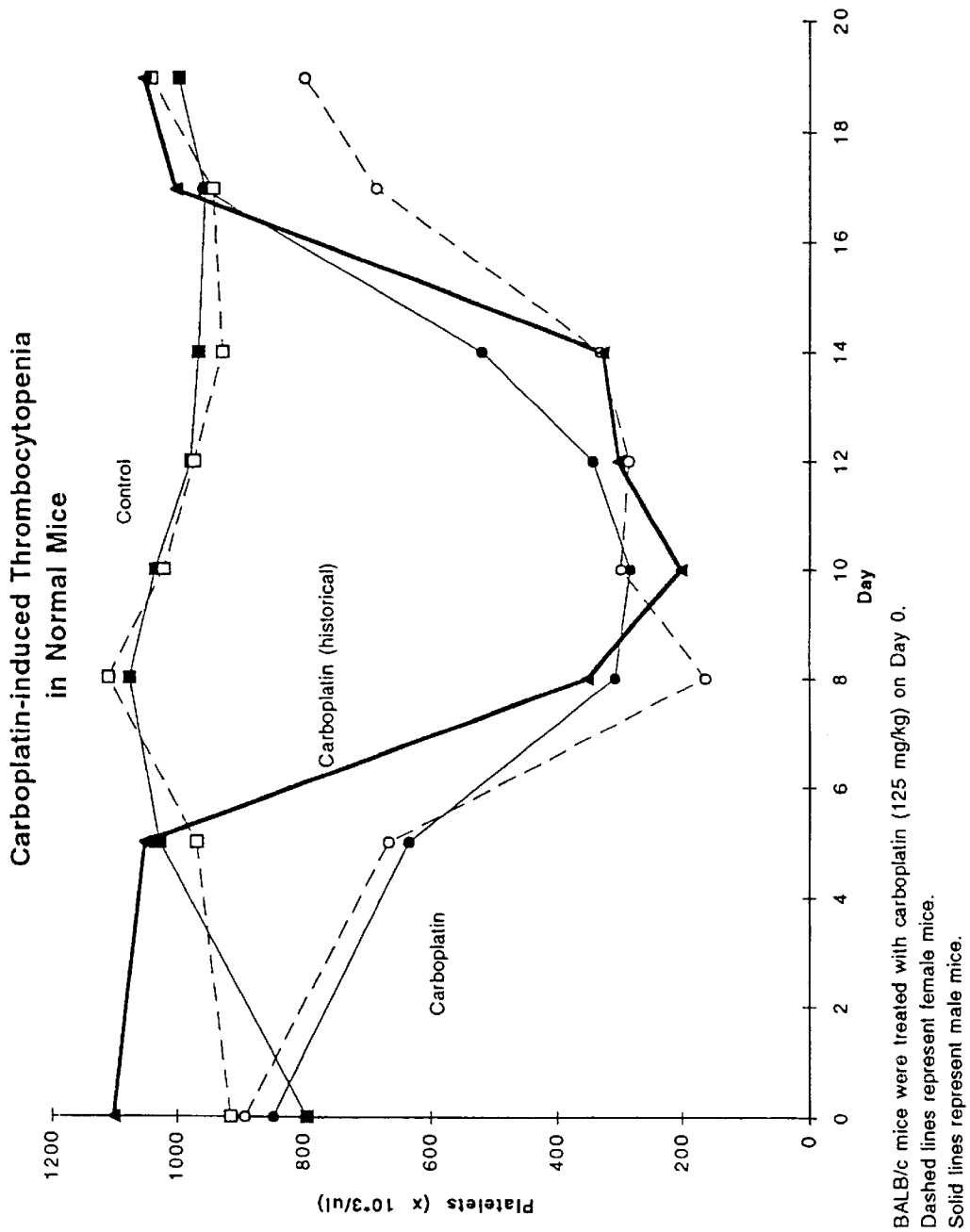
Figure 8:
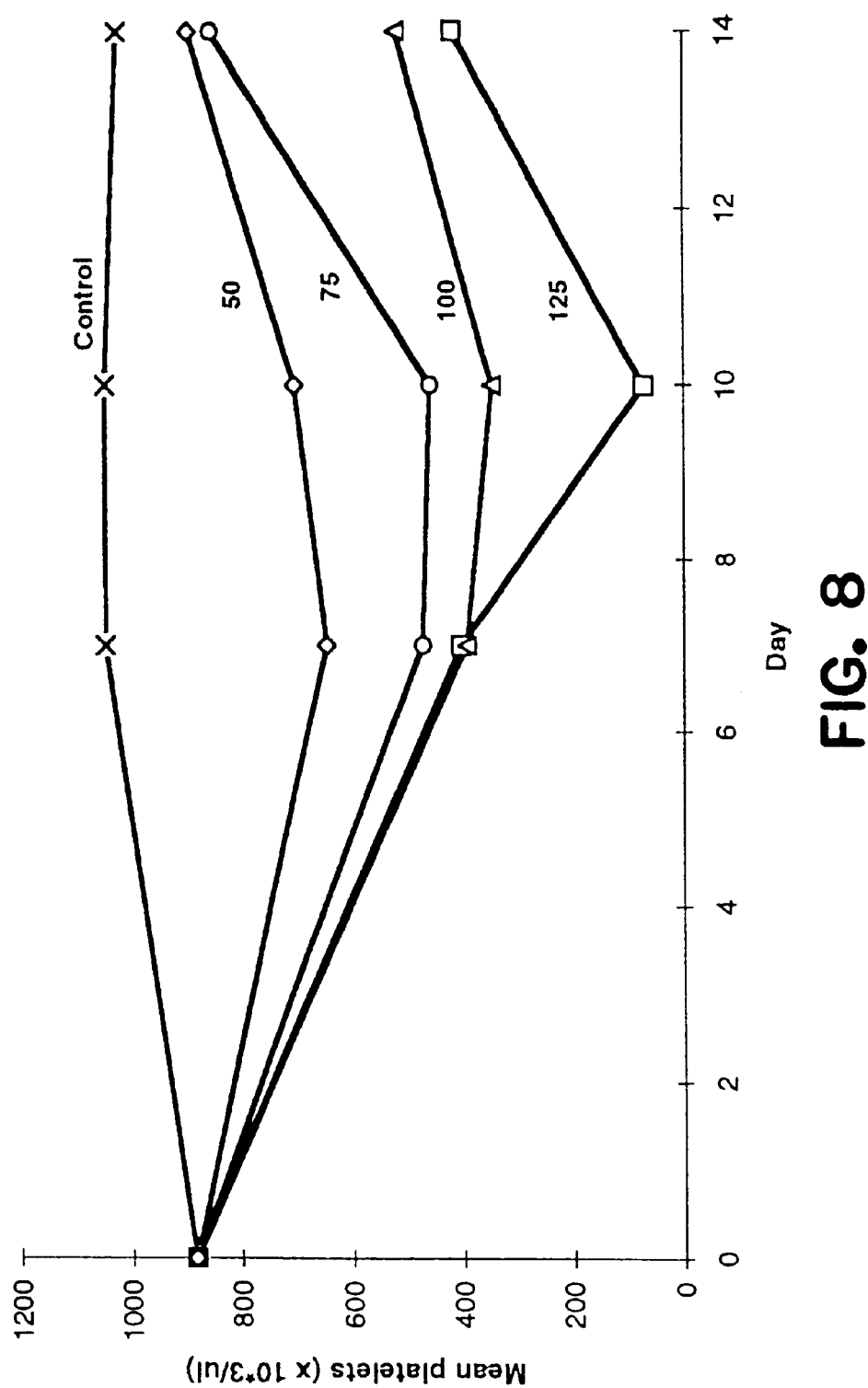
Figure 9:
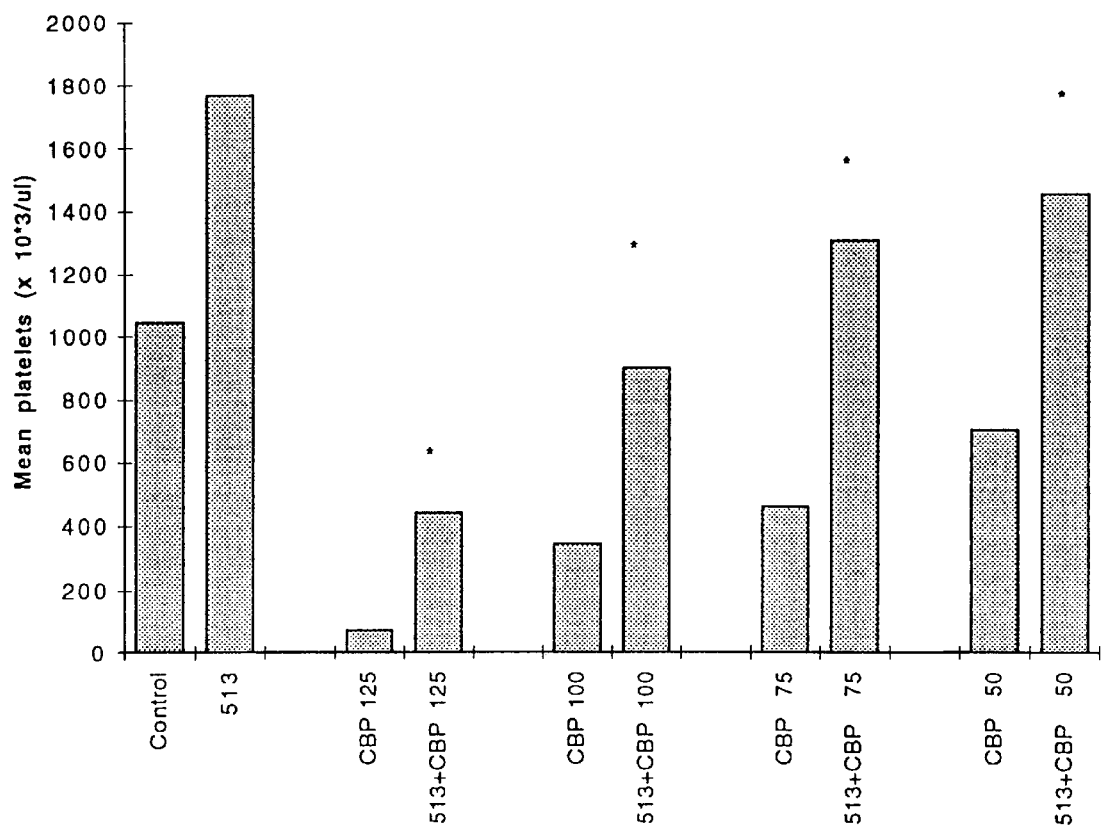

FIGS. 7 to 9 show the results of further assays evaluating activity of the peptides and peptide mimETICS of the invention. In this assay mice are made thrombocytopenic with carboplatin. FIG. 7 depicts typical results when Balb/C mice are treated with carboplatin (125 mg/kg intraperitoneally) on Day 0. The dashed lines represent untreated animals from three experiments. The solid line represent carboplatin-treated groups in three experiments. The heavy solid lines represent historical data. FIG. 8 depicts the effect of carboplatin titration on platelet counts in mice treated with the indicated amounts of carboplatin (in mg/kg, intraperitoneally (ip) on Day 0). FIG. 9 depicts amelioration of carboplatin-induced thrombocytopenia on Day 10 by peptide AF12513 (513). Carboplatin (CBP; 50–125 mg/kg, intraperitoneally) was administered on Day 0. AF12513 (1 mg/kg, ip) was given on Days 1–9.

DESCRIPTION OF SPECIFIC EMBODIMENTS

I. Definitions and General Parameters

The following definitions are set forth to illustrate and define the meaning and scope of the various terms used to describe the invention herein.

"Agonist" refers to a biologically active ligand which binds to its complementary biologically active receptor and activates the latter either to cause a biological response in the receptor or to enhance preexisting biological activity of the receptor.

"Pharmaceutically acceptable salts" refer to the non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. For a description of pharmaceutically acceptable acid addition salts as prodrugs, see Bundgaard, H., supra.

"Pharmaceutically acceptable ester" refers to those esters which retain, upon hydrolysis of the ester bond, the biological effectiveness and properties of the carboxylic acid or alcohol and are not biologically or otherwise undesirable. For a description of pharmaceutically acceptable esters as prodrugs, see Bundgaard, H., ed., *Design of Prodrugs,* Elsevier Science Publishers, Amsterdam (1985). These esters are typically formed from the corresponding carboxylic acid and an alcohol. Generally, ester formation can be accomplished via conventional synthetic techniques. (See, e.g., March *Advanced Organic Chemistry,* 3rd Ed., John Wiley & Sons, New York (1985) p. 1157 and references cited therein, and Mark et al. *Encyclopedia of Chemical Technology,* John Wiley & Sons, New York (1980)). The alcohol component of the ester will generally comprise (i) a $C_2$–$C_{12}$ aliphatic alcohol that can or can not contain one or more double bonds and can or can not contain branched carbons or (ii) a $C_7$–$C_{12}$ aromatic or heteroaromatic alcohols. This invention also contemplates the use of those compositions which are both esters as described herein and at the same time are the pharmaceutically acceptable acid addition salts thereof.

"Pharmaceutically acceptable amide" refers to those amides which retain, upon hydrolysis of the amide bond, the biological effectiveness and properties of the carboxylic acid or amine and are not biologically or otherwise undesirable. For a description of pharmaceutically acceptable amides as prodrugs, see Bundgaard, H., ed., *Desian of Prodrugs,* Elsevier Science Publishers, Amsterdam (1985). These amides are typically formed from the corresponding carboxylic acid and an amine. Generally, amide formation can be accomplished via conventional synthetic techniques. (See, e.g., March *Advanced Organic Chemistry,* 3rd Ed., John Wiley & Sons, New York (1985) p. 1152 and Mark et al. *Encyclopedia of Chemical Technology,* John Wiley & Sons, New York (1980)). This invention also contemplates the use of those compositions which are both amides as described herein and at the same time are the pharmaceutically acceptable acid addition salts thereof.

"Pharmaceutically or therapeutically acceptable carrier" refers to a carrier medium which does not interfere with the effectiveness of the biological activity of the active ingredients and which is not toxic to the host patient.

"Stereoisomer" refers to a chemical compound having the same molecular weight, chemical composition, and constitution as another, but with the atoms grouped differently. That is, certain identical chemical moieties are at different orientations in space and, therefore, when pure, has the ability to rotate the plane of polarized light. However, some pure stereoisomers may have an optical rotation that is so slight that it is undetectable with present instrumentation. The compounds of the instant invention may have one or more asymmetrical carbon atoms and therefore include various stereoisomers. All stereoisomers are included within the scope of the invention.

"Therapeutically- or pharmaceutically-effective amount" as applied to the compositions of the instant invention refers to the amount of composition sufficient to induce a desired biological result. That result can be alleviation of the signs, symptoms, or causes of a disease, or any other desired alteration of a biological system. In the present invention, the result will typically involve a decrease in the immunological and/or inflammatory responses to infection or tissue injury.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. Additionally, Bu is Butoxy, Bzl is benzyl, CHA is cyclohexylamine, Ac is acetyl, Me is methyl, Pen is penicillamine, Aib is amino isobutyric acid, Nva is norvaline, Abu is amino butyric acid, Thi is thienylalanine, OBn is O-benzyl, and hyp is hydroxyproline.

In addition to peptides consisting only of naturally-occurring amino acids, peptidomimetics or peptide analogs are also provided. Peptide analogs are commonly used in the pharmaceutical industry as non-peptide drugs with properties analogous to those of the template peptide. These types of non-peptide compound are termed "peptide mimetic" or "peptidomimetics" (Fauchere, J. *Adv. Drug Res.* 15:29 (1986); Veber and Freidinger *TINS* p.392 (1985); and Evans et al. *J. Med. Chem.* 30:1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as naturally-occurring receptor-binding polypeptide, but have one or more peptide linkages optionally replaced by a linkage selected from the group consisting of: —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods known in the art and further described in the following references: Spatola, A. F. in Chemistry and Biochemistry of Amino Acids, Peptides, and Proteins, B. Weinstein, eds., Marcel Dekker, New York, p. 267 (1983); Spatola, A. F., *Vega Data* (March 1983), Vol. 1, Issue 3, *Peptide Backbone Modifications* (general review); Morley, *Trends Pharm Sci* (1980) pp. 463–468 (general review); Hudson, D. et al., *Int J Pept Prot Res* 14:177–185 (1979) (—CH$_2$NH—, CH$_2$CH$_2$—); Spatola et al. *Life Sci* 38:1243–1249 (1986) (—CH$_2$—S); Hann *J. Chem. Soc Perkin Trans. I* 307–314 (1982) (—CH—CH—, cis and trans); Almquist et al. *J. Med. Chem.* 23:1392–1398 (1980) (—COCH$_2$—); Jennings-White et al. *Tetrahedron Lett* 23:2533 (1982) (—COCH$_2$—); Szelke et al. European Appln, EP 45665 CA (1982): 97:39405 (1982) (—CH(OH) CH$_2$—); Holladay et al. *Tetrahedron. Lett* 24:4401–4404 (1983) (—C(OH)CH$_2$—); and Hruby *Life Sci* 31:189–199 (1982) (—CH$_2$—S—); each of which is incorporated herein by reference. A particularly preferred non-peptide linkage is —CH$_2$NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others, Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) (e.g., immunoglobulin superfamily molecules) to which the peptidomimetic binds to produce the therapeutic effect. Derivitization (e.g., labeling) of peptidomimetics should not substantially interfere with the desired biological or pharmacological activity of the peptidomimetic. Generally, peptidomimetics of receptor-binding peptides bind to the receptor with high affinity and possess detectable biological activity (i.e., are agonistic or antagonistic to one or more receptor-mediated phenotypic changes).

Systematic substitution of one or more amino acids of a consensus sequence with a D-amino acid of the same type (e.g., D-lysine in place of L-lysine) may he used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); or example, by adding internal cysteine residues capable of forming intramolecular disulfide bridges which cyclize the peptide.

Synthetic or non-naturally occuring amino acids refer to amino acids which do not naturally occur in vivo but which, nevertheless, can be incorporated into the peptide structures described herein. Preferred synthetic amino acids are the D-a-amino acids of naturally occurring L-a-amino acid as well as non-naturally occurring D- and L-a-amino acids represented by the formula H$_2$NCHR$^5$COOH where R$^5$ is 1) a lower alkyl group, 2) a cycloalkyl group of from 3 to 7 carbon atoms, 3) a heterocycle of from 3 to 7 carbon atoms and 1 to 2 heteroatoms selected from the group consisting of oxygen, sulfur, and nitrogen, 4) an aromatic residue of from 6 to 10 carbon atoms optionally having from 1 to 3 substituents on the aromatic nucleus selected from the group consisting of hydroxyl, lower alkoxy, amino, and carboxyl, 5) -alkylene-Y where alkylene is an alkylene group of from 1 to 7 carbon atoms and Y is selected from the group consisting of (a) hydroxy, (b) amino, (c) cycloalkyl and cycloalkenyl of from 3 to 7 carbon atoms, (d) aryl of from 6 to 10 carbon atoms optionally having from 1 to 3 substituents on the aromatic nucleus selected from the group consisting of hydroxyl, lower alkoxy, amino and carboxyl, (e) heterocyclic of from 3 to 7 carbon atoms and 1 to 2 heteroatoms selected from the group consisting of oxygen, sulfur, and nitrogen, (f) —C(O)R$^2$ where R$^2$ is selected from the group consisting of hydrogen, hydroxy, lower alkyl, lower alkoxy, and —NR$^3$R$^4$ where R$^3$ and R$^4$ are independently selected from the group consisting of hydrogen and lower alkyl, (g) —S(O)$_n$R$^6$ where n is an integer from 1 to 2 and R$^6$ is lower alkyl and with the proviso that R$^5$ does not define a side chain of a naturally occurring amino acid.

Other preferred synthetic amino acids include amino acids wherein the amino group is separated from the carboxyl group by more than one carbon atom such as b-alanine, g-aminobutyric acid, and the like.

Particularly preferred synthetic amino acids include, by way of example, the D-amino acids of naturally occurring L-amino acids, L-1-napthyl-alanine, L-2-naphthylalanine, L-cyclohexylalanine, L-2-amino isobutyric acid, the sulfoxide and sulfone derivatives of methionine (i.e., HOOC—(H$_2$NCH)CH$_2$CH$_2$—S(O)$_n$R$^6$) where n and R$_6$ are as defined above as well as the lower alkoxy derivative of methionine (i.e., HOOC—(H$_2$NCH)CH$_2$CH$_2$—OR$^6$ where R$^6$ is as defined above).

"Detectable label" refers to materials, which when covalently attached to the peptides and peptide mimetics of this invention, permit detection of the peptide and peptide mimetics in vivo in the patient to whom the peptide or peptide mimetic has been administered. Suitable detectable labels are well known in the art and include, by way of example, radioisotopes, fluorescent labels (e.g., fluorescein), and the like. The particular detectable label employed is not critical and is selected relative to the amount of label to be employed as well as the toxicity of the label at the amount of label employed. Selection of the label relative to such factors is well within the skill of the art.

Covalent attachment of the detectable label to the peptide or peptide mimetic is accomplished by conventional methods well known in the art. For example, when the $^{125}$I radioisotope is employed as the detectable label, covalent attachment of $^{125}$I to the peptide or the peptide mimetic can be achieved by incorporating the amino acid tyrosine into the peptide or peptide mimetic and then iodating the peptide. If tyrosine is not present in the peptide or peptide mimetic, incorporation of tyrosine to the N or C terminus of the peptide or peptide mimetic can be achieved by well known chemistry. Likewise, $^{32}$p can be incorporated onto the peptide or peptide mimetic as a phosphate moiety through, for example, a hydroxyl group on the peptide or peptide mimetic using conventional chemistry.

II. Overview

The present invention provides compounds that bind to and activate the TPO-R or otherwise behave as a TPO agonist. These compounds include "lead" peptide compounds and "derivative" compounds constructed so as to have the same or similar molecular structure or shape as the lead compounds but that differ from the lead compounds either with respect to susceptibility to hydrolysis or proteolysis and/or with respect to other biological properties, such as increased affinity for the receptor. The present invention also provides compositions comprising an effective amount of a TPO agonist, and more particularly a compound, that is useful for treating hematological disorders, and particularly, thrombocytopenia associated with chemotherapy, radiation therapy, or bone marrow transfusions.

III. Identification of TPO-Agonists

Peptides having a binding affinity to TPO-R can be readily identified by random peptide diversity generating systems coupled with an affinity enrichment process.

Specifically, random peptide diversity generating systems include the "peptides on-plasmids" system described in U.S. Pat. Nos. 5,270,170 and 5,338,665; the "peptides on phage" system described in U.S. patent application Ser. No. 07/718,577, filed Jun. 20, 1991 which is a continuation in part application of U.S. patent application Ser. No. 07/541,108, filed Jun. 20, 1990, and in Cwirla et al., *Proc. Natl. Acad. Sci. USA* 87:6378–6382 (1980); the "polysome system" described in U.S. patent application Ser. No. 08/300,262, filed Sep. 2, 1994, which is a continuation-in-part application based on U.S. patent application Ser. No. 08/144,775, filed Oct. 29, 1993 and PCT WO 95/11992; "the encoded synthetic library (ESL)" system described in U.S. patent application Ser. No. 08/146,886, filed Nov. 12, 1993 which is a continuation in part application of U.S. patent application Ser. No. 07/946,239, filed Sep. 16, 1992, which is a continuation in part application of U.S. patent application Ser. No. 07/762,522, filed Sep. 18, 1991; and the "very large scale immobilized polymer synthesis" system described in U.S. Pat. No. 5,143,854; PCT Patent Publication No. 90/15070, published Dec. 13, 1990; U.S. patent application Ser. No. 07/624,120, filed Dec. 6, 1990; Fodor et al. *Science* 251:767–773 (February/1991); Dower and Fodor *Ann. Rep. Med. Chem.* 26:271–180 (1991); and U.S. patent application Ser. No. 805,727, filed Dec. 6, 1991.

Using the procedures described above, random peptides were generally designed to have a defined number of amino acid residues in length (e.g., 12). To generate the collection of oligonucleotides encoding the random peptides, the codon motif (NNK)x, where N is nucleotide A, C, G, or T (equimolar; depending on the methodology employed, other nucleotides can be employed), K is G or T (equimolar), and x is an integer corresponding to the number of amino acids in the peptide (e.g., 12) was used to specify any one of the 32 possible codons resulting from the NNK motif: 1 for each of 12 amino acids, 2 for each of 5 amino acids, 3 for each of 3 amino acids, and only one of the three stop codons. Thus, the NNK motif encodes all of the amino acids, encodes only one stop codon, and reduces codon bias.

In the systems employed, the random peptides were presented either on the surface of a phage particle, as part of a fusion protein comprising either the pIII or the pVIII coat protein of a phage fd derivative (peptides on phage) or as a fusion protein with the LacI peptide fusion protein bound to a plasmid (peptides on plasmids).

The phage or plasmids, including the DNA encoding the peptides, were identified and isolated by an affinity enrichment process using immobilized TPO-R. The affinity enrichment process, sometimes called "spanning," involves multiple rounds of incubating the phage, plasmids, or polysomes with the immobilized receptor, collecting the phage, plasmids, or polysomes that bind to the receptor (along with the accompanying DNA or mRNA), and producing more of the phage or plasmids (along with the accompanying LacI-peptide fusion protein) collected. The extracellular domain (ECD) of the TPO-R typically was used during panning.

After several rounds of affinity enrichment, the phage or plasmids and accompanying peptides were examined by ELISA to determine if the peptides bind specifically to TPO-R. This assay was carried out similarly to the procedures used in the affinity enrichment process, except that after removing unbound phage, the wells were typically treated with rabbit anti-phage antibody, then with alkaline phosphatase (AP)-conjugated goat anti-rabbit antibody. The amount of alkaline phosphatase in each well was determined by standard methods. A similar ELISA procedure for use in the peptides on plasmids system is described in detail below.

By comparing test wells with control wells (no receptor), one can determine whether the fusion proteins bind to the receptor specifically. The phage pools found to bind to TPO-R were screened in a colony lift probing format using radiolabelled monovalent receptor. This probe can be produced using protein kinase A to phosphorylate a kemptide sequence fused to the C-terminus of the soluble receptor. The "engineered" form of the TPO receptor is then expressed in host cells, typically CHO cells. Following PI-PLC harvest of the receptors, the receptor was tested for binding to TPO or TPO-R specific phage clones. The receptor is then labeled to high specific activity with $^{33}$p for use as a monovalent probe to identify high affinity ligands using colony lifts.

Peptides found to bind specifically to the receptor were then synthesized as the free peptide (e.g., no phage) and tested in a blocking assay. The blocking assay was carried out in similar fashion to the ELISA, except that TPO or a reference peptide was added to the wells before the fusion protein (the control wells were of two types: (1) no receptor; and (2) no TPO or reference peptide). Fusion proteins for which the binding to the receptor was blocked by TPO or the reference peptide contain peptides in the random peptide portion that are preferred compounds of the invention.

TPO-R, as well as its extracellular domain, were produced in recombinant host cells. One useful form of TPO-R is constructed by expressing the protein as a soluble protein in baculovirus transformed host cells using standard methods; another useful form is constructed with a signal peptide for protein secretion and for glycophospholipid membrane anchor attachment. This form of anchor attachment is called "PIG-tailing". See Caras and Wendell *Science* 243:1196–1198 (1989) and Lin et al. *Science* 249:677–679 (1990).

Using the PIG-tailing system, one can cleave the receptor from the surface of the cells expressing the receptor (e.g., transformed CHO cells selected for high level expression of receptor with a cell sorter) with phospholipase C. The cleaved receptor still comprises a carboxy terminal sequence of amino acids, called the "HPAP tail", from the signal protein for membrane attachment and can be immobilized without further purification. The recombinant receptor protein can be immobilized by coating the wells of microtiter plates with an anti-HPAP tail antibody (Ab 179 or MAb 179), blocking non-specific binding with bovine serum albumin (BSA) in PBS, and then binding cleaved recombinant receptor to the antibody. Using this procedure, one should perform the immobilization reaction in varying concentrations of receptor to determine the optimum amount for a given preparation, because different preparations of recombinant protein often contain different amounts of the desired protein. In addition, one should ensure that the immobilizing antibody is completely blocked (with TPO or some other blocking compound) during the affinity enrichment process. Otherwise, unblocked antibody can bind undesired phage during the affinity enrichment procedure. One can use peptides that bind to the immobilizing antibody to block unbound sites that remain after receptor immobilization to avoid this problem or one can simply immobilize the receptor directly to the wells of microtiter plates, without the aid of an immobilizing antibody. See U.S. patent application Ser. No. 07/947,339, filed Sep. 18, 1992, incorporated herein by reference.

When using random peptide generation systems that allow for multivalent ligand-receptor interaction, one must recognize that the density of the immobilized receptor is an important factor in determining the affinity of the ligands that can bind to the immobilized receptor. At higher receptor densities (e.g., each anti-receptor antibody-coated well treated with 0.25 to 0.5 mg of receptor), multivalent binding is more likely to occur than at lower receptor densities (e.g., each anti-receptor antibody-coated well treated with 0.5 to 1 ng of the receptor), If multivalent binding is occurring, then one will be more likely to isolate ligands with relatively lower affinity, unless one uses high densities of immobilized receptor to identify lead compounds and uses lower receptor densities to isolate higher affinity derivative compounds.

To discriminate among higher affinity peptides, a monovalent receptor probe frequently is used. This probe can be produced using protein kinase A to phosphorylate a kemptide sequence fused to the C-terminus of the soluble receptor. The "engineered" form of the TPO receptor is then expressed in host cells, typically CHO cells. Following PI-PLC harvest of the receptors, the receptor was tested for binding to TPO or TPO-R specific phage clones. The receptor is then labeled to high specific activity with $^{33}$p for use as a monovalent probe to identify high affinity ligands using colony lifts.

Preferred screening methods to facilitate identification of peptides which bind TPO-R involve first identifying lead peptides which bind to the extracellular domain of the receptor and then making other peptides which resemble the lead peptides. Specifically, using a pill or pVIII-based peptides on phage system, a random library can be screened to discover a phage that presents a peptide that binds to TPO-R. The phage DNAs are sequenced to determine the sequences of the peptides displayed on the surface of the phages.

Clones capable of specific binding to the TPO-R were identified from a random linear 10-mer pVIII library and a random cyclic 10-mer and 12-mer pVIII libraries. The sequences of these peptides serve as the basis for the construction of other peptide libraries designed to contain a high frequency of derivatives of the initially identified peptides. These libraries can be synthesized so as to favor the production of peptides that differ from the binding peptide in only a few residues. This approach involves the synthesis of an oligonucleotide with the binding peptide coding sequence, except that rather than using pure preparations of each of the four nucleoside triphosphates in the synthesis, one uses mixtures of the four nucleoside triphosphates (i.e., 55% of the "correct" nucleotide, and 15%, each of the other three nucleotides is one preferred mixture for this purpose and 70% of the "correct" nucleotide and 10% of each of the other three nucleotides is another preferred mixture for this purpose) so as to generate derivatives of the binding peptide coding sequence.

A variety of strategies were used to derivatize the lead peptides by making "mutagenesis on a theme" libraries. These included a pVIII phagemid mutagenesis library based on the consensus sequence mutagenized at 70:10:10:10 frequency and extended on each terminus with random residues to produce clones which enclode the sequence (SEQ ID NO:20) XXXX (C, S, P, or R) TLREWL XXXXXX (C or S). A similar extended/mutagenized library was constructed using the peptides-on-plasmids system to produce clones which enclode the sequence (SEQ ID NO:22) XXXXX (C, S, P, or R) TLREWL XXXXXXX. An additional extended/mutagenized library (SEQ ID NO:23), XXXX (C, S, P, or R) TLREWL XXXXXX (C or S), was constructed using the polysome display system. All three libraries were screened with peptide elution and probed with radiolabeled monovalent receptor.

The "peptides on plasmids" techniques was also used for peptide screening and mutagenesis studies and is described in greater detail in U.S. Pat. No. 5,338,665, which is incorporated herein by reference for all purposes. According to this approach, random peptides are fused at the C-terminus of LacI through expression from a plasmid vector carrying the fusion gene. Linkage of the LacI-peptide fusion to its encoding DNA occurs via the lacO sequences on the plasmid, forming a stable peptide-LacI-plasmid complex that can be screened by affinity purification (panning) on an immobilized receptor. The plasmids thus isolated can then be reintroduced into *E. coli* by electroporation to amplify the selected population for additional rounds of screening, or for the examination of individual clones.

In addition, random peptide screening and mutagenesis studies were performed using a modified C-terminal Lac-T display system in which display valency was reduced ("headpiece dimer" display system). The libraries were screened and the resulting DNA inserts were cloned as a pool into a maltose binding protein (MBP) vector allowing their expression as a C-terminal fusion protein. Crude cell lysates from randomly picked individual MBP fusion clones were then assayed for TPO-R binding in an ELISA format, as discussed above.

Peptide mutagenesis studies were also conducted using the polysome display system, as described in co-pending application U.S. patent application Ser. No. 08/300,262, filed Sep. 2, 1994, which is a continuation-in-part application based on U.S. patent application Ser. No. 08/144,775, filed Oct. 29, 1993 and PCT WO 95/11992, each of which is incorporated herein by references for all purposes. A mutagenesis library was constructed based on the sequence (SEQ ID NO:24) X X X X (C,P,R, or S) t l r e f l X X X X X X (C or S), in which X represents a random NNK codon, and the lower case letters represent amino acid codons containing 70:10:10:10 mutagenesis at positions 1 and 2 and K (G or T) at position 3 of the codon. The library was panned for 5 rounds against TPO receptor which had been immobilzed on magnetic beads. After the fifth round, the PCR amplified pool was cloned into pAFF6 and the ELISA positive clones were sequenced. The sequences were subcloned into an MBP vector and their binding affinities were determined by an MBP ELISA.

To imobilize the TPO-R for polysome screening, Ab 179 was first chemically conjugated to tosyl-activated magnetic beads (available from Dynal Corporation) as described by the manufacturer. The beads were incubated with antibody in 0.5 M borate buffer (pH 9.5) overnight at room temperature. The beads were washed and combined with TPO-R containing the "HPAP" tail. The antibody coated beads and receptor were incubated for 1 hour at 4° C., and the beads were washed again prior to adding the polysome library.

Screening of the various libraries described above yielded the TPO receptor binding peptides shown in Tables 1 and 2 below, as well as others not listed herein.

TABLE 1

SEQ ID

TABLE 2-continued

SEQ ID NOS 59–167, respectively

Peptide

A C E G C T L R Q W L E Y V R V G C
A Q R G C T L Q Y F V S Y G X D M C
G V C G C T L R E F L A I P H T S C
S E G G C T L R E W V A S S L A N C
S N S R C T L R E W I I Q G C D F S
S N S R C T L R E W I I Q G C D F S
C L G C T L S Q W R K R T R C D T H
Y R G C S R A Q L L G G E C R K K
G R G C T L K Q W K Q G D C G R S
V R G G C A L R D W V A G E C F D W T
L W R G C T L N G F K S R H C G S P E
C T L R S W K H R G C A P
G R G C T R A Q W L A G C C T G H
R A G C T L R E F R K G C L A L
K R G C T L A E M I R G C N R S N
G R G C T L K Q W K Q G D C G R S
R W R G C S L A K L K K G A A C G R G
R G G C T L R E W R R V R V I N
G R G C T L K Q W K Q G D C G R S
R Y G C T R H Q W L V G T C V R H

IC$_{50}$ values for some additional representative peptides are given in the table below. A variety of methods can be used to evaluate IC$_{50}$ values. for example, an equilibrium binding ELISA assay, using either MBP-TPO or lacI-peptide tracer, was used to determine whether the peptides inhibit the binding of TPO to the extracellular domain of the TPO receptor. Typically, the IC$_{50}$ value were determined using the free peptide. The IC$_{50}$ value can be determined using the free peptide, which optionally can be C-terminally amidated, or can be prepared as an ester or other carboxy amide.

To recreate the exact sequence displayed on the phage, the N-terminal and C-terminal amino acids of the synthetic peptides are often preceded by one or two glycine residues. These glycines are not believed to be necessary for binding or activity. Likewise, to mimic the exact sequence of peptides displayed on polysomes, the C-terminal amino acids of the synthetic peptides are often preceded by the sequence M A S. Again, this sequence is not believed to be necessary for binding or activity.

IC$_{50}$ values are indicated symbolically by the symbols "−" and "+", and "++". For examples, those peptides which showed IC$_{50}$ values in excess of 200 μM are indicated with a "−". Those peptides which gave IC$_{50}$ values of less than or equal to 200 μM are given a "+", while those which gave IC$_{50}$ values of 500 nm or less are indicated with a "++", Those peptides which gave IC$_{50}$ values at or near the cutoff point for a particular symbol are indicated with a hybrid designator, e.g., "+/−". Those peptides for which IC$_{50}$ values were not determined are listed as "N.D.". The IC$_{50}$ value for peptides having the structure: (SEQ ID NO:15) G G C T L R E W L H G G F C G G was 500 nm or less. (Note the N-terminal and C-terminal amino acids were preceded by two glycines to recreate the exact sequence displayed by the phage. These glycines are not believed to be necessary for binding or activity.)

TABLE 3

SEQ ID NOS 6, 7, 8, 9, 168, 11 & 10, respectively

| Peptide | Affinity |
|---|---|
| G G C A D G P T L R E W I S F C G G | ++ |
| G N A D G P T L R Q W L E G R R P K N | ++ |
| G G C A D G P T L R E W I S F C G G K | ++ |
| T I K G P T L R Q W L K S R E H T S | ++ |
| G P T L R Q W L | − |
| L A I E G P T L R Q W L H G N G R D T | ++ |
| S I E G P T L R E W L T S R T P H S | ++ |

The tables above, especially Table 3, illustrate that a preferred core peptide comprises a sequence of amino acids (SEQ ID NO:2):

X$_1$ X$_2$ X$_3$ X$_4$ X$_5$ X$_6$ X$_7$ where X$_1$ is C, L, M, P, Q, V; X$_2$ is F, K, L, N, Q, R, S, T or V; X$_3$ is C, F, I, L, M, R, S, V or W; X$_4$ is any of the 20 genetically coded L-amino acids; X$_5$ is A, D, E, G, K, M, Q, R, S, T, V or Y; X$_6$ is C, F, G, L, M, S, V, W or Y; and X$_7$ is C, G, I, K, L, M, N, R or V.

In a preferred embodiment the core peptide comprises a sequence of amino acids (SEQ ID NO:3):

X$_8$ G X$_1$ X$_2$ X$_3$ X$_4$X$_5$ W X$_7$ where X$_1$ is L, M, P, Q, or V; X$_2$ is F, R, S, or T; X$_3$ is F, L, V, or W; X$_4$ is A, K, L, M, R, S, V, or T; X$_5$ is A, E, G, K, M, Q, R, S, or T; X$_7$ is C, I, K, L, M or V; and each X$_8$ residue is independently selected from any of the 20 genetically coded L-amino acids, their stereoisomeric D-amino acids; and non-natural amino acids. Preferably, each X$_8$ residue is independently selected from any of the 20 genetically coded L-amino acids and their stereoisomeric D-amino acids. In a preferred embodiment (SEQ ID NO:4), X$_1$ is P; X$_2$ is T; X$_3$ is L; X$_4$ is R; X$_5$ is E or Q; and X$_7$ is I or L.

More preferably, the core peptide comprises a sequence of amino acids (SEQ ID NO:5):

X$_9$ X$_8$ G X$_1$ X$_2$ X$_3$ X$_4$ X$_5$ W X$_7$ where X$_9$ is A, C, E, G, I, L , M, P, R, Q, S, T, or V; and X$_8$ is A, C, D, E, K, L, Q, R, S, T, or V. More preferably, X$_9$ is A or I; and X is D, E, or K.

Particularly preferred peptides include (SEQ ID NOS 6–13, respectively): G G C A D G P T L R E W I S F C G G; G N A D G P T L R Q W L E G R R P K N; G G C A D G P T L R E W I S F C G G K; T I K G P T L R Q W L K S R E H T S; S I E G P T L R E W L T S R T P H S; L A I E G P T L R Q W L H G N G R D T; C A D G P T L R E W I S F C; and I E G P T L R Q W L A A R A.

In further embodiments of the invention, preferred peptides for use in this invention include peptides having a core structure comprising sequence of amino acids: sequence of amino acids (SEQ ID NO:14):

C X$_2$ X$_3$ X$_4$ X$_5$ X$_6$ X$_7$ where X$_2$ is K, L, N, Q, R, S, T or V; X$_3$ is C, F, I, L, M, R, S or V; X$_4$ is any of the 20 genetically coded L-amino acids; X$_5$ is A, D, E, G, S, V or Y; X$_6$ is C, F, G, L, M, S, V, W or Y; and X$_7$ is C, G, I, K, L, M, N, R or V. In a more preferred embodiment, X$_4$ is A, E, G, H, K, L, M, P, Q, R, S, T, or W. In a further embodiment, X$_2$ is S or T; X$_3$ is L or R; X$_4$ is R; X$_5$ is D, E, or G; X$_6$ is F, L, or W; and X$_7$ is I, K, L, R, or V. Particularly preferred peptides include (SEQ ID NO:15): G G C T L R E W L H G G F C G G.

In a further embodiment, preferred peptides for use in this invention include peptides having a structure comprising a sequence of amino acids (SEQ ID NO:16):

X$_8$ C X$_2$ X$_3$ X$_4$ X$_5$ X$_6$ X$_7$ where X$_2$ is F, K, L, N, Q, R, S, T or V; X$_3$ is C, F, I, L, M, R, S, V or W; X$_4$ is any of the 20 genetically coded L-amino acids; $X_5$ is A, D, E, G, K, M, Q, R, S, T, V or Y; $X_6$ is C, F, G, L, M, S, V, W or Y; $X_7$ is C, G, I, K, L, M, N, R or V; and $X_8$ is any of the 20 genetically coded L-amino acids. In some embodiments, $X_8$ is preferably G, S, Y, or R.

Peptides and peptidomimetics having an $IC_{50}$ of greater than about 100 mM lack sufficient binding to permit use in either the diagnostic or therapeutic aspects of this invention. Preferably, for diagnostic purposes, the peptides and peptidomimetics have an $IC_{50}$ of about 2 mM or less and, for pharmaceutical purposes, the peptides and peptidomimetics have an $IC_{50}$ of about 100 $\mu$M or less.

The binding peptide sequence also provides a means to determine the minimum size of a TPOR binding compound of the invention. Using the "encoded synthetic library" (ESL) system or the "very large scale immobilized polymer synthesis" system, one can not only determine the minimum size of a peptide with such activity, but one can also make all of the peptides that form the group of peptides that differ from the preferred motif (or the minimum size of that motif) in one, two, or more residues. This collection of peptides can then be screened for ability to bind to TPO-receptor. These immobilized polymers synthesis systems or other peptide synthesis methods can also be used to synthesize truncation analogs, deletion analogs, substitution analogs, and combinations thereof all of the peptide compounds of the invention.

The peptides and peptide mimetics of the present invention were also evaluated in a thrombopoietin dependent cell proliferation assay, as described in greater detail in Example 2 below. Cell proliferation is measured by techniques known in the art, such as an MTT assay which correlates with $^3$H-thymidine incorporation as an indication of cell proliferation (see Mossmann *J. Immunol. Methods* 65:55 (1983)). The peptides tested stimulated proliferation of TPO-R transfected Ba/F3 cells in a dose dependent manner as shown in FIG. 1A. These peptides have no effect on the parental cell line as shown in FIG. 1B.

FIGS. 7 to 9 show the results of a further assay evaluating activity of the peptides and peptide mimetics of the invention. In this assay mice are made thrombocytopenic with carboplatin. FIG. 7 depicts typical results when Balb/C mice are treated with carboplatin (125 mg/kg intraperitoneally) on Day 0. The dashed lines represent untreated animals from three experiments. The solid line represent carboplatin-treated groups in three experiments. The heavy solid lines represent historical data. FIG. 8 depicts the effect of carboplatin titration on platelet counts in mice treated with the indicated amounts of carboplatin (in mg/kg, intraperitoneally (ip) on Day 0). FIG. 9 depicts amelioration of carboplatin-induced thrombocytopenia on Day 10 by peptide AF12513 (513). Carboplatin (CBP; 50–125 mg/kg, intraperitoneally) was administered on Day 0. AF12513 (1 mg/kg, ip) was given on Days 1–9. These results show the peptides of the invention can ameliorate thrombocytopenia in a mouse model.

In addition, certain peptides of the present invention can be dimerized or oligomerized, thereby increasing the affinity and/or activity of the compounds. To investigate the effect that peptide dimerization/oligomerization has on TPO mimetic potency in cell proliferation assays, a C-terminally biotinylated analog of the peptide (SEQ ID NO:6) G G C A D G P T L R E W I S F C G G was synthesized (SEQ ID NO:8) (G G C A D G P T L R E W I S F C G G K (Biotin)). The peptide was preincubated with streptavidin in serum-free HEPES-buffered RPMI at a 4:1 molar ratio. The complex was tested for stimulation of cell proliferation of TPO-R transfected Ba/F3 cells, as above, alongside free biotinylated peptide and the unbiotinylated parental peptide. FIG. 2A shows the results of the assay for the complexed biotinylated peptide (AF 12885 with streptavidin (SA)) for both the transfected and parental cell lines. FIG. 2B shows the results of the assay for the free biotinylated peptide (AF 12285) for both the transfected and parental cell lines. FIG. 2C shows the results of the assay for streptavidin alone for both the transfected and parental cell lines. These figures illustrate that the pre-formed complex was approximately 10 times as potent as the free peptide.

The specificity of the binding and activity of the peptides of the invention was also examined by studying the cross reactivity of the peptides for the erythropoieitin receptor (EPO-R). The EPO-R is also a member of the haematopoietin growth factor receptor family, as is TPO-R. The peptides of the invention, as well as TPO, EPO, and a known EPO-binding peptide, were examined in a cell proliferation assay using an EPO-dependent cell line. This assay utilized FDCP-1, a growth factor dependent murine multi-potential primitive haematopoietic progenitor cell line (see, e.g., Dexter et al. *J. Exp. Med.* 152:1036–1047 (1981)) as the parental cell line. This cell line can proliferate, but not differentiate when supplemented with WEHI-3-conditioned media (a medium that contains IL-3, ATCC number T1B68). The parental cell line is transfected with human or murine EPO-R to produce the FDCP-1-EPO-R cell line. These transfected cell lines can proliferate, but not differentiate in the presence of human or murine EPO.

The cells were grown to half stationary density in the presence of the necessary growth factors. The cells are then washed in PBS and starved for 16–24 hours in whole media without the growth factors. After determining the viability of the cells, stock solutions (in whole media without the growth factors) are made to give about $10^5$ cells per 50 microliters. Serial dilutions of the compounds (typically, the free solution phase peptide as opposed to a phage-bound or other bound or immobilized peptide) to be tested are made in 96-well tissue culture plates for a final volume of 50 microliters per well. Cells (50 microliters) are added to each well and the cells are incubated for 24–48 hours, at which point the negative controls should die or be quiescent. Cell proliferation is then measured by techniques known in the art, such as an MTT assay.

FIGS. 3A–G show the results of a series of control experiments showing the activity of TPO, the peptides of the present invention, EPO, and EPO-R binding peptides in a cell proliferation assay using either the TPO-R transfected Ba/F3 cell line and its corresponding parental line, or an EPO-dependent cell line and its corresponding parental line. FIG. 3A depicts the results for TPO in the cell proliferation assay using the TPO-R transfected Ba/F3 cell line and its corresponding parental line. FIG. 3B depicts the results for EPO in the cell proliferation assay using the TPO-R transfected Ba/F3 cell line and its corresponding parental line. FIG. 3C depicts the results for complexed biotinylated peptide (AF 12285 with streptavidin (SA)) and a completed form of a biotinylated EPO-R binding peptide (AF 11505 with SA) in the TPO-R transfected Ba/F3 cell line. The results for the corresponding parental cell line are shown in FIG. 3D. FIG. 3E depicts the results for TPO in the cell proliferation assay using the EPO-dependent cell line. FIG. 3F depicts the results for EPO in the cell proliferation assay using the EPO-dependent cell line. FIG. 3G depicts the results for complexed biotinylated peptide (AF 12285 with streptavidin (SA)) and the complexed form of a biotinylated EPO-R binding peptide (AF 11505 with SA) in the EPO-dependent cell line. These results show that the peptides of the invention bind and activate the TPO-R with a high degree of specificity.

IV. Preparation of Peptides and Peptide Mimetics

A. Solid Phase Synthesis

The peptides of the invention can be prepared by classical methods known in the art, for example, by using standard solid phase techniques. The standard methods include exclusive solid phase synthesis, partial solid phase synthesis methods, fragment condensation, classical solution synthesis, and even by recombinant DNA technology. See, e.g., Merrifield *J. Am. Chem. Soc.* 85:2149 (1963), incorporated herein by reference. On solid phase, the synthesis is typically commenced from the C-terminal end of the peptide using an alpha-amino protected resin. A suitable starting material can be prepared, for instance, by attaching the required alpha-amino acid to a chloromethylated resin, a hydroxymethyl resin, or a benzhydrylamine resin. One such chloromethylated resin is sold under the tradename BIO-BEADS SX-1 by Bio Rad Laboratories, Richmond, Calif., and the preparation of the hydroxymethyl resin is described by Bodonszky et al. *Chem. Ind.* (London) 38:1597 (1966). The benzhydrylamine (BHA) resin has been described by Pietta and Marshall *Chem. Commn.* 650 (1970) and is commercially available from Beckman Instruments, Inc., Palo Alto, Calif., in the hydrochloride form.

Thus, the compounds of the invention can be prepared by coupling an alpha-amino protected amino acid to the chloromethylated resin with the aid of, for example, cesium bicarbonate catalyst, according to the method described by Gisin *Helv. Chim. Acta.* 56:1467 (1973). After the initial coupling, the alpha-amino protecting group is removed by a choice of reagents including trifluoroacetic acid (TFA) or hydrochloric acid (HCl) solutions in organic solvents at room temperature.

The alpha-amino protecting grounds are those known to be useful in the art of stepwise synthesis of peptides. Included are acyl type protecting groups (e.g. formyl, trifluoroacetyl, acetyl), aromatic urethane type protecting groups (e.g. benzyloxycarboyl (Cbz) and substituted Cbz), aliphatic urethane protecting groups (e.g. t-butyloxycarbonyl (Boc), isopropyloxycarbonyl, cyclohexyloxycarbonyl) and alkyl type protecting groups (e.g. benzyl, triphenylmethyl). Boc and Fmoc are preferred protecting groups. The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

The side chain protecting groups for Tyr include tetrahydropyranyl, tert-butyl, trityl, benzyl, Cbz, Z-Br-Cbz, and 2,5-dichlorobenzyl. The side chain protecting groups for Asp include benzyl, 2,6-dichlorobenzyl, methyl, ethyl, and cyclohexyl. The side chain protecting groups for Thr and Ser include acetyl, benzoyl, trityl, tetrahydropyranyl, benzyl, 2,6-dichlorobenzyl, and Cbz. The side chain protecting group for Thr and Ser is benzyl. The side chain protecting groups for Arg include nitro, Tosyl (Tos), Cbz, adamantyloxycarbonyl mesitoylsulfonyl (Mts), or Boc. The side chain protecting groups for Lys include Cbz, 2-chlorobenzyloxycarbonyl (2-Cl—Cbz), 2-bromobenzyloxycarbonyl (2-BrCbz), Tos, or Boc.

After removal of the alpha-amino protecting group, the remaining protected amino acids are coupled stepwise in the desired order. An excess of each protected amino acid is generally used with an appropriate carboxyl group activator such as dicyclohexylcarbodiimide (DCC) in solution, for example, in methylene chloride ($CH_2Cl_2$), dimethyl formamide (DMF) mixtures.

After the desired amino acid sequence has been completed, the desired peptide is decoupled from the resin support by treatment with a reagent such as trifluoroacetic acid or hydrogen fluoride (HF), which not only cleaves the peptide from the resin, but also cleaves all remaining side chair, protecting groups. When the chloromethylated resin is used, hydrogen fluoride treatment results in the formation of the free peptide acids. When the benzhydrylamine resin is used, hydrogen fluoride treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides.

These solid phase peptide synthesis procedures are well known in the art and further described in Stewart *Solid Phase Peptide Syntheses* (Freeman and Co., San Francisco, (1969)).

Using the "encoded synthetic library" or "very large scale immobilized polymer synthesis" system described in U.S. patent application Ser. Nos. 07/492,462, filed Mar. 7, 1990; Ser. No. 07/624,120, filed Dec. 6, 1990; and Ser. No. 07/805,727, filed Dec. 6, 1991; one can not only determine the minimum size or a peptide with such activity, one can also make all of the peptides that form the group of peptides that differ from the preferred motif (or the minimum size of that motif) in one, two, or more residues. This collection of peptides can then be screened for ability to bind to TPO-R. This immobilized polymer synthesis system or other peptide synthesis methods can also be used to synthesize truncation analogs and deletion analogs and combination of truncation and deletion analogs of all of the peptide compounds of the invention.

B. Synthetic Amino Acids

These procedures can also be used to synthesize peptides in which amino acids other than the 20 naturally occurring, genetically encoded amino acids are substituted at one, two, or more positions of any of the compounds of the invention. For instance, naphthylalanine can be substituted for tryptophan, facilitating synthesis. Other synthetic amino acids that can be substituted into the peptides of the present invention include L-hydroxypropyl, L-3, 4-dihydroxyphenylalanyl, d amino acids such as L-d-hydroxylysyl and D-d-methylalanyl, L-a-methylalanyl, b amino acids, and isoquinolyl. D amino acids and non-naturally occurring synthetic amino acids can also be incorporated into the peptides of the present invention.

One can replace the naturally occurring side chains of the 20 genetically encoded amino acids (or D amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered hetereocyclic. In particular, proline analogs in which the ring size of the proline residue is changed from 5 members to 4, 6, or 7 members can be employed. cyclic groups can be saturated or unsaturated, and if unsaturated, can be aromatic or non-aromatic.

Cyclic groups can be saturated or unsaturated, and if unsaturated, can be aromatic or non-aromatic. Heterocyclic groups preferably contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups can be substituted or unsubstituted. Where a group is substituted, the substituent can be alkyl, alkoxy, halogen, oxygen, or substituted or unsubstituted phenyl.

One can also readily modify the peptides of the instant invention by phosphorylation, and other methods for making peptide derivatives of the compounds of the present invention are described in Hruby et al.[42] Thus, the peptide compounds of the invention also serve as a basis to prepare peptide mimetics with similar biological activity.

The peptide compounds of the invention, including peptidomimetics, can be covalently modified to one or more of a variety of nonproteinaceous polymers, e.g., polyethylene glycol, polypropylene glycol, or polyoxyalkenes, in the manner set forth in U.S. Pat. Nos. 4,640,835; 4,496,689; 4,301,144; 4,670,417; 4,791,192; or 4,179,337, all which are incorporated by reference in their entirety herein.

C. Terminal Modifications

Those of skill in the art recognize that a variety of techniques are available for constructing peptide mimetics with the same or similar desired biological activity as the corresponding peptide compound but with more favorable activity than the peptide with respect to solubility, stability, and susceptibility to hydrolysis and proteolysis. See, for example, Morgan and Gainor *Ann. Rep. Med. Chem.* 24:243–252 (1989). The following describes methods for preparing peptide mimetics modified at the N-terminal amino group, the C-terminal carboxyl group, and/or changing one or more of the amido linkages in the peptide to a non-amido linkage. It being understood that two or more such modifications can be coupled in one peptide mimetic structure (e.g., modification at the C-terminal carboxyl group and inclusion of a —$CH_2$-carbamate linkage between two amino acids in the peptide).

1. N-Terminal Modifications

The peptides typically are synthesized as the free acid but, as noted above, could be readily prepared as the amide or ester. One can also modify the amino and/or carboxy terminus of the peptide compounds of the invention to produce other compounds of the invention. Amino terminus modifications include methylating (i.e., —$NHCH_3$ or —$NH(CH_3)_2$), acetylating, adding a carbobenzoyl group, or blocking the amino terminus with any blocking group containing a carboxylate functionality defined by RCOO—, where R is selected from the group consisting of naphthyl, acridinyl, steroidyl, and similar groups. Carboxy terminus modifications include replacing the free acid with a carboxamide group or forming a cyclic lactam at the carboxy terminus to introduce structural constraints.

Amino terminus modifications are as recited above and include alkylating, acetylating, adding a carbobenzoyl group, forming a succinimide group, etc. Specifically, the N-terminal amino group can then be reacted as follows:

(a) to form an amide group of the formula RC(O)NH— where R is as defined above by reaction with an acid halide [e.g., RC(O)Cl] or acid anhydride. Typically, the reaction can be conducted by contacting about equimolar or excess amounts (e.g., about 5 equivalents) of an acid halide to the peptide in an inert diluent (e.g., dichloromethane) preferably containing an excess (e.g., about 10 equivalents) of a tertiary amine, such as diisopropylethylamine, to scavenge the acid generated during reaction. Reaction conditions are otherwise conventional (e.g., room temperature for 30 minutes). Alkylation of the terminal amino to provide for a lower alkyl N-substitution followed by reaction with an acid halide as described above will provide for N-alkyl amide group of the formula RC(O)NR—;

(b) to form a succinimide group by reaction with succinic anhydride. As before, an approximately equimolar amount or an excess of succinic anhydride (e.g., about 5 equivalents) can be employed and the amino group is converted to the succinimide by methods well known in the art including the use of an excess (e.g., ten equivalents) of a tertiary amine such as diisopropylethylamine in a suitable inert solvent (e.g., dichloromethane). See, for example, Wollenberg, et al., U.S. Pat. No. 4,612,132 which is incorporated herein by reference in its entirety. It is understood that the succinic group can be substituted with, for example, $C_2$–$C_6$ alkyl or —SR substituents which are prepared in a conventional manner to provide for substituted succinimide at the N-terminus of the peptide. Such alkyl substituents are prepared by reaction of a lower olefin ($C_2$–$C_6$) with maleic anhydride in the manner described by Wollenberg, et al., supra. and —SR substituents are prepared by reaction of RSH with maleic anhydride where R is as defined above;

(c) to form a benzyloxycarbonyl-NH— or a substituted benzyloxycarbonyl-NH— group by reaction with approximately an equivalent amount or an excess of CBZ—Cl (i.e., benzyloxycarbonyl chloride) or a substituted CBZ—Cl in a suitable inert diluent (e.g., dichloromethane), preferably containing a tertiary amine to scavenge the acid generated during the reaction;

(d) to form a sulfonamide group by reaction with an equivalent amount or an excess (e.g., 5 equivalents) of R—$S(O)_2$Cl in a suitable inert diluent (dichloromethane) to convert the terminal amine into a sulfonamide where R is as defined above. Preferably, the inert diluent contains excess tertiary amine (e.g., ten equivalents) such as diisopropylethylamine, to scavenge the acid generated during reaction. Reaction conditions are otherwise conventional (e.g., room temperature for 30 minutes);

(e) to form a carbamate group by reaction with an equivalent amount or an excess (e.g., 5 equivalents) of R—OC(O)Cl or R—OC(O)O$C_6H_4$-p-$NO_2$ in a suitable inert diluent (e.g., dichloromethane) to convert the terminal amine into a carbamate where R is as defined above. Preferably, the inert diluent contains an excess (e.g., about 10 equivalents) of a tertiary amine, such as diisopropylethylamine, to scavenge any acid generated during reaction. Reaction conditions are otherwise conventional (e.g., room temperature for 30 minutes); and (f) to form a urea group by reaction with an equivalent amount or an excess (e.g., 5 equivalents) of R—N=C=O in a suitable inert diluent (e.g., dichloromethane) to convert the terminal amine into a urea (i.e., RNHC(O)NH—) group where R is as defined above. Preferably, the inert diluent contains an excess (e.g., about 10 equivalents) of a tertiary amine, such as diisopropylethylamine. Reaction conditions are otherwise conventional (e.g., room temperature for about 30 minutes).

2. C-Terminal Modifications

In preparing peptide mimetics wherein the C-terminal carboxyl group is replaced by an ester (i.e., —C(O)OR where R is as defined above), the resins used to prepare the peptide acids are employed, and the side chain protected peptide is cleaved with base and the appropriate alcohol, e.g., methanol. Side chain protecting grounds are then removed in the usual fashion by treatment with hydrogen fluoride to obtain the desired ester.

In preparing peptide mimetics wherein the C-terminal carboxyl group is replaced by the amide —C(O)NR$^3$R$^4$, a benzhydrylamine resin is used as the solid support for peptide synthesis. Upon completion of the synthesis, hydrogen fluoride treatment to release the peptide from the support results directly in the free peptide amide (i.e., the C-terminus is —C(O)NH$_2$). Alternatively, use of the chloromethylated resin during peptide synthesis coupled with reaction with ammonia to cleave the side chain protected peptide from the support yields the free peptide amide and reaction with an alkylamine or a dialkylamine yields a side chain protected alkylamide or dialkylamide (i.e., the C-terminus is —C(O)NRR$^1$ where R and R$^1$ are as defined above). Side chain protection is then removed in the usual fashion by treatment with hydrogen fluoride to give the free amides, alkylamides, or dialkylamides.

In another alternative embodiment, the C-terminal carboxyl group or a C-terminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl groups activator such as dicyclohexylcarbodiimide (DCC) in solution, for example, in methylene chloride (CH$_2$Cl$_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Such methods are well known in the art.

One can also cyclize the peptides of the invention, or incorporate a desamino or descarboxy residue at the terminii of the peptide, so that there is no terminal amino or carboxyl group, to decrease susceptibility to proteases or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and the pharmaceutically acceptable salts thereof.

D. Backbone Modifications

Other methods for making peptide derivatives of the compounds of the present invention are described in Hruby et al. *Biochem J.* 268(2):249–262 (1990), incorporated herein by reference. Thus, the peptide compounds of the invention also serve as structural models for non-peptide compounds with similar biological activity. Those of skill in the art recognize that a variety of techniques are available for constricting compounds with the same or similar desired biological activity as the lead peptide compound but with more favorable activity than the lead with respect to solubility, stability, and susceptibility to hydrolysis and proteolysis. See Morgan and Gainor *Ann. Rep. Med. Chem.* 24:243–252 (1989), incorporated herein by reference. These techniques include replacing the peptide backbone with a backbone composed of phosphonates, amidates, carbamates, sulfonamides, secondary amines, and N-methylamino acids.

Peptide mimetics wherein one or more of the peptidyl linkages [—C(O)NH—] have been replaced by such linkages as a —Cl$_2$-carbamate linkage, a phosphonate linkage, a —CH$_2$-sulfonamide linkage, a urea linkage, a secondary amine (—CH$_2$NH—) linkage, and an alkylated peptidyl linkage [—C(O)NR$^6$— where R$^6$ is lower alkyl] are prepared during conventional peptide synthesis by merely substituting a suitably protected amino acid analogue for the amino acid reagent at the appropriate point during synthesis.

Suitable reagents include, for example, amino acid analogues wherein the carboxyl group of the amino acid has been replaced with a moiety suitable for forming one of the above linkages. For example, if one desires to replace a —C(O)NR— linkage in the peptide with a —CH$_2$-carbamate linkage (—CH$_2$OC(O)NR—), then the carboxyl (—COOH) group of a suitably protected amino acid is first reduced to the —CH$_2$OH group which is then converted by conventional methods to a —OC.(O)Cl functionality or a para-nitrocarbonate —OC(O)O—C$_6$H$_4$-p-NO$_2$ functionality. Reaction of either of such functional groups with the free amine or an alkylated amine on the N-terminus of the partially fabricated peptide found on the solid support leads to the formation of a —CH$_2$OC(O)NR— linkage. For a more detailed description of the formation of such —CH$_2$-carbamate linkages, see Cho et al *Science*, 261:1303–1305 (1993).

Similarly, replacement of an amido linkage in the peptide with a phosphonate linkage can be achieved in the manner set forth in U.S. patent application Ser. Nos. 07/943,805, 08/081,577, and 08/119,700, the disclosures of which are incorporated herein by reference in their entirety.

Replacement of an amido linkage in the peptide with a —CH$_2$-sulfonamide linkage can be achieved by reducing the carboxyl (—COOH) group of a suitably protected amino acid to the —CH$_2$OH group and the hydroxyl group is then converted to a suitable leaving group such as a tosyl group by conventional methods. Reaction of the tosylated derivative with, for example, thioacetic acid followed by hydrolysis and oxidative chlorination will provide for the —CH$_2$—S(O)$_2$Cl functional group which replaces the carboxyl group of the otherwise suitably protected amino acid. Use of this suitably protected amino acid analogue in peptide synthesis provides for inclusion of an —CH$_2$S(O)$_2$NR— linkage which replaces the amido linkage in the peptide thereby providing a peptide mimetic. For a more complete description on the conversion of the carboxyl group of the amino acid to a —CH$_2$S(O)$_2$Cl group, see, for example, Weinstein, Boris *Chemistry & Biochemistry of Amino Acids, Peptides and Proteins* Vol. 7, pp. 267–357, Marcel Dekker, Inc., New York (1983) which is incorporated herein by reference.

Replacement of an amido linkage in the peptide with a urea linkage can be achieved in the manner set forth in U.S. patent application Ser. No. 08/147,805 which application is incorporated herein by reference in its entirety.

Secondary amine linkages wherein a —CH$_2$NH— linkage replaces the amido linkage in the peptide can be prepared by employing, for example, a suitably protected dipeptide analogue wherein the carbonyl bond of the amido linkage has been reduced to a CH$_2$ group by conventional methods. For example, in the case of diglycine, reduction of the amide to the amine will yield after deprotection H$_2$NCH$_2$CH$_2$NHCH$_2$COOH which is then used in N-protected form in the next coupling reaction. The preparation of such analogues by reduction of the carbonyl group of the amido linkage in the dipeptide is well known in the art.

The suitably protected amino acid analogue is employed in the conventional peptide synthesis in the same manner as would the corresponding amino acid. For example, typically about 3 equivalents of the protected amino acid analogue are employed in this reaction. An inert organic diluent such as methylene chloride or DMF is employed and, when an acid is generated as a reaction by-product, the reaction solvent will typically contain an excess amount of a tertiary amine to scavenge the acid generated during the reaction. One particularly preferred tertiary amine is diisopropylethylamine which is typically employed in about 10 fold excess. The reaction results in incorporation into the peptide mimetic of an amino acid analogue having a non-peptidyl linKage. Such substitution can be repeated as desired such that from zero to all of the amido bonds in the peptide have been replaced by non-amido bonds.

One can also cyclize the peptides of the invention, or incorporate a desamino or descarboxy residue at the terminal of the peptide, so that there is no terminal amino or carboxyl group, to decrease susceptibility to proteases or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and the pharmaceutically acceptable salts thereof. Examples of cyclized compounds are provided in Tables 4, 5, 6, 8, and 9.

E. Disulfide Bond Formation

The compounds of the present invention may exist in a cyclized form with an intramolecular disulfide bond between the thiol groups of the cysteines. Alternatively, an intermolecular disulfide bond between the thiol groups of the cysteines can be produced to yield a dimeric (or higher oligomeric) compound. One or more of the cysteine residues may also be substituted with a homocysteine. These intramolecular or intermolecular disulfide derivatives can be represented schematically as shown below:

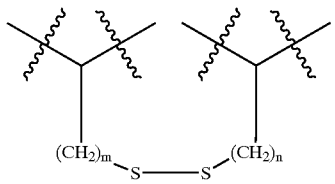

wherein m and n are independently 1 or 2.

Other embodiments of this invention provide for analogs of these disulfide derivatives in which one of the sulfurs has been replaced by a $CH_2$ group or other isostere for sulfur. These analogs can be made via an intramolecular or intermolecular displacement, using methods known in the arc as shown below:

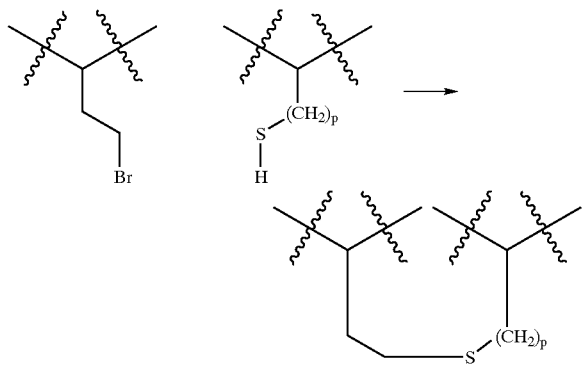

wherein p is 1 or 2. One of skill in the art will readily appreciate that this displacement can also occur using other homologs of the a-amino-g-butyric acid derivative shown above and homocysteine.

Alternatively, the amino-terminus of the peptide can be capped with an alpha-substituted acetic acid, wherein the alpha substituent is a leaving group, such as an a-haloacetic acid, for example, a-chloroacetic acid, a-bromoacetic acid, or a-iodoacetic acid. The compounds of the present invention can be cyclized or dimerized via displacement of the leaving group by the sulfur of the cysteine or homocysteine residue. See, e.g., Barker et al. *J. Med. Chem.* 35:2040–2048 (1992) and Or et al. *J. Org. Chem.* 56:3146–3149 (1991), each of which is incorporated herein by reference. Examples of dimerized compounds are provided in Tables 7, 9, and 10.

V. Utility

The compounds of the invention are useful in vitro as unique tools for understanding the biological role of TPO, including the evaluation of the many factors thought to influence, and be influenced by, the production of TPO and the receptor binding process. The present compounds are also useful in the development of other compounds that bind to and activate the TPO-R, because the present compounds provide important information on the relationship between structure and activity that should facilitate such development.

The compounds are also useful as competitive binders in assays to screen for new TPO receptor agonists. In such assay embodiments, the compounds of the invention can be used without modification or can be modified in a variety of ways; for example, by labeling, such as covalently or non-covalently joining a moiety which directly or indirectly provides a detectable signal. In any of these assays, the materials thereto can be labeled either directly or indirectly. Possibilities for direct labeling include label groups such as: radiolabels such as $^{125}I$, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups. The compounds may also include spacers or linkers in cases where the compounds are to be attached to a solid support.

Moreover, based on their ability to bind to the TPO receptor, the peptides of the present invention can be used as reagents for detecting TPO receptors on living cells, fixed cells, in biological fluids, in tissue homogenates, in purified, natural biological materials, etc. For example, by labelling such peptides, one can identify cells having TPO-R on their surfaces. In addition, based on their ability to bind the TPO receptor, the peptides of the present invention can be used in in situ staining, FACS (fluorescence-activated cell sorting), Western blotting, ELISA, etc. In addition, based on their ability to bind to the TPO receptor, the peptides of the present invention can be used in receptor purification, or in purifying cells expressing TPO receptors on the cell surface (or inside permeabilized cells).

The compounds of the present invention can also be utilized as commercial reagents for various medical research and diagnostic uses. Such uses include but are not limited to: (1) use as a calibration standard for quantitating the activities of candidate TPO agonists in a variety of functional assays; (2) use to maintain the proliferation and growth of TPO-dependent cell lines; (3) use in structural analysis of the TPO-receptor through co-crystallization; (4) use to investigate the mechanism of TPO signal transduction/ receptor activation; and (5) other research and diagnostic applications wherein the TPO-receptor is preferably activated or such activation is conveniently calibrated against a known quantity of a TPO agonist, and the like.

The compounds of the present invention can be used for the in vitro expansion of megakaryocytes and their committed progenitors, both in conjunction with additional cytokines or on their own. See, e.g., DiGiusto et al. PCT Publication No. 95/05843, which is incorporated herein by reference. Chemotherapy and radiation therapies cause thrombocytopenia by killing the rapidly dividing, more mature population of megakaryocytes. However, these therapeutic treatments can also reduce the number and viability of the immature, less mitotically active megakaryocyte precursor cells. Thus, amelioration of the thrombocytopenia by TPO or the compounds of the present invention can be hastened by infusing patients post chemotherapy or radiation therapy with a population of his or her own cells enriched for megakaryocytes and immature precursors by in vitro culture.

The compounds of the invention can also be administered to warm blooded animals, including humans, to activate the TPO-R in vivo. Thus, the present invention encompasses methods for therapeutic treatment of TPO related disorders that comprise administering a compound of the invention in amounts sufficient to mimic the effect of TPO on TPO-R in vivo. For example, the peptides and compounds of the invention can be administered to treat a variety of hematological disorders, including but not limited to platelet disorders and thrombocytopenia, particularly when associated with bone marrow transfusions, radiation therapy, and chemotherapy.

In some embodiments of the invention, TPO antagonists are preferably first administered to patients undergoing chemotherapy or radiation therapy, followed by administration of the tpo agonists of the invention.

The activity of the compounds of the present invention can be evaluated either in vitro or in vivo in one of the numerous models described in McDonald *Am. J. of Pediatric Hematology/Oncology* 14:8–21 (1992), which is incorporated herein by reference.

According to one embodiment, the compositions of the present invention are useful for treating thrombocytopenia associated with bone marrow transfusions, radiation therapy, or chemotherapy. The compounds typically will be administered prophylactically prior to chemotherapy, radiation therapy, or bone marrow transplant or after such exposure.

Accordingly, the present invention also provides pharmaceutical compositions comprising, as an active ingredient, at least one of the peptides or peptide mimetics of the invention in association with a pharmaceutical carrier or diluent. The compounds of this invention can be administered by oral, pulmonary, parental (intramuscular, intraperitoneal, intravenous (IV) or subcutaneous injection), inhalation (via a fine powder formulation), transdermal, nasal, vaginal, rectal, or sublingual routes of administration and can be formulated in dosage forms appropriate for each route of administration. See, e.g., Bernstein et al. PCT Patent Publication No. WO 93/25221; Pitt et al. PCT Patent Publication No. WO 94/17784; and Pitt et al. European Patent Application 613, 683, each of which is incorporated herein by reference.

Solid dosage forms for oral administration include capsules, tablets, pills, powders, and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e g., lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parental administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose". Amounts effective for this use will depend on the severity of the disease and the weigh, and general state of the patient.

The compositions of the invention can also be microencapsulated by, for example, the method of Tice and Bibi (in Treatise on Controlled Drug Delivery, ed. A. Kydonieus, Marcel Dekker, N.Y. (1992), pp. 315–339).

In prophylactic applications, compositions containing the compounds of the invention are administered to a patient susceptible to or otherwise at risk of a particular disease. Such an amount is defined to be a "prophylactically effective dose". In this use, the precise amounts again depend on the patient's state of health and weight.

The quantities of the TPO agonist necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman et al. (eds), *Goodman and Gilman's: The Pharmacological Basis of Therapeutics,* 8th ed., Pergamon Press (1990); and *Remington's Pharmaceutical Sciences,* 7th ed., Mack Publishing Co., Easton, Pa. (1985); each of which is hereby incorporated by reference.

The peptides and peptide mimetics of this invention are effective in treating TPO mediated conditions when administered at a dosage range of from about 0.001 mg to about 10 mg/kg of body weight per day. The specific dose employed is regulated by the particular condition being treated, the route of administration as well as by the judgement of the attending clinician depending upon factors such as the severity of the condition, the age and general condition of the patient, and the like.

Although only preferred embodiments of the invention are specifically described above, it will be appreciated that modifications and variations of the invention are possible without departing from the spirit and intended scope of the invention.

EXAMPLE 1

Solid Phase Peptide Synthesis

Various peptides of the invention were synthesized using the Merrifield solid phase synthesis techniques (See Steward and Young, *Solid Phase Peptide Synthesis*, 2d. edition, Pierce Chemical, Rockford, Ill. (1984) and Merrifield *J. Am. Chem. Soc.* 85:2149 (1963)) on a Milligen/Biosearch 9600 automated instrument or an Applied Biosystems Inc. Model 431A peptide synthesizer. The peptides were assembled using standard protocols of the Applied Biosystems Inc. System Software version 1.01. Each coupling was performed for one-two hours with BOP (benzotriazolyl N-oxtrisdimethylaminophosphonium hexafluorophosphate) and HOBt (1-hydroxybenzotriazole).

The resin used was HMP resin or PAL (Milligen/ Biosearch), which is a cross-linked polystyrene resin with 5-(4'-Fmoc-aminomethyl-3,5'-dimethyoxyphenoxy) valeric acid as a linker. Use of PAL resin results in a carboxyl terminal amide functionality upon cleavage of the peptide from the resin. Upon cleavage, the HMP resin produces a carboxylic acid moiety at the C-terminus of the final product. Most reagents, resins, and protected amino acids (free or on the resin) were purchased from Millipore or Applied Biosystems Inc.

The Fmoc group was used for amino protection during the coupling procedure. Primary amine protection on amino acids was achieved with Fmoc and side chain protection groups were t-butyl for serine, tyrosine, asparagine, glutamic acid, and threonine; trityl for glutamine; Pmc (2,2,5,7,8-pentamethylchroma sulfonate) for arginine; N-t-butyloxycarbonyl for tryptophan; N-trityl for histidine and glutamine; and S-trityl for cysteine.

Removal of the peptides from the resin and simultaneous deprotection of the side chain functions were achieved by treatment with reagent K or slight modifications of it. Alternatively, in the synthesis of those peptides, with an amidated carboxyl terminus, the fully assembled peptide was cleaved with a mixture of 90% trifluoroacetic acid, 5% ethanedithiol, and 5%, water, initially at 4° C., and gradually increasing to room temperature. The deprotected peptides were precipitated with diethyl ether. In all cases, purification was by preparative, reverse-phase, high performance liquid chromatography on a $C_{18}$ bonded silica gel column with a gradient of acetonitrile/water in 0.1% trifluoroacetic acid. The homogeneous peptides were characterized by Fast Atom Bombardment mass spectrometry or electrospray mass spectrometry and amino acid analysis when applicable.

EXAMPLE 2

Bioassays

Bioactivity of the peptides can be measured using a thrombopoietin dependent cell proliferation assay. Murine IL-3 dependent Ba/F3 cells were transfected with full length human TPO-R. In the absence of IL-3 (WEHI-3 conditioned media), these cells are dependent on TPO for proliferation. The parental, untransfected cell line does not respond to human TPO, but remains IL-3 dependent.

Bioassays have been performed on both of the above cell lines using synthetic peptides derived from library screening. The cells were grown in complete RPMI-10 media, containing 10% WEHI-3 conditioned media, then washed twice in PBS, resuspended in media which lacked WEHI-3 conditioned media, and added to wells containing dilutions of peptide or TPO at $2 \times 10^4$ cells/well. The cells were incubated for 48 hours at 37° C. in a humidified 5% $CO_2$ atmosphere and metabolic activity was assayed by the reduction of MTT to formazan, with absorbance at 570 nM measured on an ELISA plate reader The peptides tested stimulated proliferation of TPO-R transfected Ba/F3 cells in a dose dependent manner as shown in FIG. 1. These peptides have no effect on the parental cell line.

EXAMPLE 3

Binding Affinity

Binding affinities of chemically synthesized peptides for TPO-R were measured in a competition binding assay. The wells of a microtiter plate were coated with 1 mg streptavidin, blocked with PBS/1% BSA, followed by 50 ng of biotinylated anti-receptor immobilizing antibody (Ab179). The wells were then treated with a 1:10 dilution of soluble TPO-R harvest. Various concentrations of peptide or peptide mimetic were mixed with a constant amount of a truncated form of TPO consisting of residues 1–156 fused to the C-terminus of maltose binding protein (MBP-$TPO_{156}$), The peptide MBP-$TPO_{156}$ mixtures were added to the TPO-R coated wells, incubated for 2 hours at 4° C. and then washed with PBS. The amount of MBP-$TPO_{156}$ that was bound at equilibrium was measured by adding a rabbit anti-sera directed against MBP, followed by alkaline phosphatase conjugated goat anti-rabbit IgG. The amount of alkaline phosphatase in each well was then determined using standard methods.

The assay is conducted over a range of peptide concentrations and the results are graphed such that the y axis represents the amount of bound MBP-$TPO_{156}$ and the x axis represents the concentration of peptide or peptide mimetic. One can then determine the concentration at which the peptide or peptide mimetic will reduce by 50% ($IC_{50}$) the amount of MBP-$TPO_{156}$ bound to immobilized TPO-R. The dissociation constant (Kd) for the peptide should be similar to the measured $IC_{50}$ using the assay conditions described above.

EXAMPLE 4

"Peptides on Plasmids"

The pJS142 vector is used for library construction and is shown in FIG. 4. Three oligonucleotide sequences (SEQ ID NOS 169–171, respectively) are needed for library construction: ON-829 (5' ACC ACC TCC GG); ON-830 (5' TTA CTT AGT TA) and a library specific oligonucleotide of interest (5' GA GGT GGT {NNK}$_n$ TAA CTA AGT AAA GC), where {NNK}$_n$ denotes a random region of the desired length and sequence. The oligonucleotides can be 5' phosphorylated chemically during synthesis or after purification with polynucleotide kinase. They are then annealed at a 1:1:1 molar ratio and ligated to the vector.

The strain of *E. coli* which is preferably used for panning has the genotype: Δ(srl-recA) endA1 nupG lon-11 slaw1 hsdR17 Δ(ompT-fepC)266 ΔclpA319::kan ΔlacI lac ZU118 which can be prepared from an *E. coli* strain from the *E. coli* Genetic Stock Center at Yale University (*E. coli* b/r, stock center designation CGSC:6573) with genotype lon-11 sulA1. The above *E. coli* strain is prepared for use in electroporation as described by Dower et al. *Nucleic Acids Res.* 16:6127 (1988), except that lot glycerol is used for all wash steps. The cells are tested for efficiency using 1 pg of a Bluescript plasmid (Stratagene). These cells are used for growth of the original library and for amplification of the enriched population after each round of panning.

Peptides on plasmids are released from cells for panning by gentle enzymatic digestion of the cell wall using lysozyme. After pelleting of the cell debris, the crude lysate can be used directly on most receptors. If some additional purification of the plasmid complexes is needed, a gel filtration column can be used to remove many of the low molecular weight contaminants in the crude lysate.

Panning is carried out in a buffer (HEKL) of a lower salt concentration than most physiological buffers. The panning can be conducted in microtiter wells with a receptor immobilized on a nonblocking monoclonal antibody (MAb) or by panning on beads or on columns. More specifically, in the first round of panning, 24 wells, each coated with receptor, can be used. For the second round, six wells coated with receptor (PAN sample) and 6 wells without receptor (NC sample) are typically used. Comparison of the number of plasmids in these two samples can give an indication of whether receptor specific clones are being enriched by panning. "Enrichment" is defined as the ratio of PAN transformants to those recovered from the NC sample. Enrichment of 10 fold is usually an indication that receptor specific clones are present.

In later rounds of panning, it is useful to reduce the input of lysate into the wells to lower nonspecific background binding of the plasmid complexes. In round 2, usually 100 μl of lysate per well is used. In round 3, 100 μl of lysate per well diluted with 1/10 in HEKL/BSA is used. For further rounds of panning, typically an input of plasmid transforming units of at least 1000 fold above the estimated remaining diversity is used.

The binding properties of the peptides encoded by individual clones are typically examined after 3, 4, or 5 rounds of panning, depending on the enrichment numbers observed. Typically, an ELISA that detects receptor specific binding by LacI-peptide fusion proteins is used. LacI is normally a tetramer and the minimum functional DNA binding species is a dimer. The peptides are thus displayed multivalently on the fusion protein. Assuming that a sufficient density of receptor can be immobilized in wells, the peptides fused to LacI will bind to the surface in a cooperative, multivalent fashion. This cooperative binding permits the detection of binding events of low intrinsic affinity. The sensitivity of this assay is an advantage in that initial hits of low affinity can be easily identified, but is a disadvantage in that the signal in the ELISA is not correlated with the intrinsic affinity of the peptides. Fusion of the peptides to maltose binding protein (MBP) as described below permits testing in an ELISA format where signal strength is better correlated with affinity. See FIGS. 5A–B.

DNA from clones of interest can be prepared in double stranded form using any standard miniprep procedure. The coding sequences of interesting single clones or populations of clones can be transferred to vectors that fuse those sequences in frame with the gene encoding MBP, a protein that generally occurs as a monomer in solution. The cloning of a library into pJS142 creates a BspEI restriction site near the beginning of the random coding region of the library. Digestion with BspEI and ScaI allows the purification of a ~900 bp DNA fragment that can be subcloned into one of two vectors, pELM3 (cytoplasmic) or pELM15 (periplasmic), which are simple modifications of the pMALc2 and pMALp2 vectors, respectively, available commercially from New England Biolabs. See FIGS. 5A–B. Digestion of pELM3 and pELM15 with AgeI and ScaI allows efficient cloning of the BspEI-ScaI fragment from the pJS142 library. The BspEI and AgeI ends are compatible for ligation. In addition, correct ligation of the ScaI sites is essential to recreate a functional b1a (Amp resistance) gene, thus lowering the level of background clones from undesired ligation events. Expression of the tac promoter-driven MBP-peptide fusions can then be induced with IPTG.

Lysates for the LacI or MBP ELISAs are prepared from individual clones by lysing cells using lysozyme and removing insoluble cell debris by centrifugation. The lysates are then added to wells containing immobilized receptor and to control wells without receptor. Binding by the LacI or MBP peptide fusions is detected by incubation with a rabbit polyclonal antiserum directed against either LacI or MBP followed by incubation with alkaline phosphatase labeled goat anti rabbit second antibody. The bound alkaline phosphatase is detected with D-nitrophenyl phosphate chromagenic substrate.

EXAMPLE 5

"Headpiece Dimer" System

A variant of the LacI peptides-on-plasmids technique utilizes a DNA binding protein called "headpiece dimer". DNA binding by the *E. coli* lac regressor is mediated by the approximately 60 amino acid "headpiece" domain. The dimer of the headpiece domains that binds to the lac operator is normally formed by association of the much larger approximately 300 amino acid C-terminal domain. The "headpiece dimer" system utilizes headpiece dimer molecules containing two headpieces connected via short peptide linker. These proteins bind DNA with sufficient stability to allow association of a peptide epitope displayed at the C-terminus of the headpiece dimer with the plasmid encoding that peptide.

The random peptides are fused to the C-terminus of the headpiece dimer, which binds to the plasmid that encoded it to make a peptide-headpiece dimer-plasmid complex that can be screened by panning. The headpiece dimer peptides-on-plasmids system allows greater selectivity for high affinity ligands than the LacI system. Thus, the headpiece dimer system is useful for making mutagenesis libraries based on initial low-affinity hits, and selecting higher affinity variants of those initial sequences.

The libraries are constructed as with peptides on plasmids using headpiece dimer vector pCMG14 (see FIGS. 6A–C). The presence of the lac operator is not required for plasmid binding by the headpiece dimer protein. The libraries were introduced into bacterial strain comprising *E. coli* (lon-11 sulA1 hsd17 (ompT-fepC) ΔclpA319::kan ΔlacI lac ZU118 Δ(srl-recA) 306::Tn10 and amplified under conditions of basal (A) promoter induction. Panning of headpiece dimer libraries is carried out by similar procedures to those used for LacI libraries, except that HEK buffer is used instead of HEKL buffer and elution of plasmids from the wells is performed with aqueous phenol instead of with IPTG. Sequences from headpiece dimer panning are often characterized after transfer to the MBP vector so that they can be tested in the affinity sensitive MBP ELISA and also so that populations of clones can be screened by colony lifts with labeled receptor.

EXAMPLE 6

In this example cyclized compounds were subjected to three assays. First, $IC_{50}$ valves were obtained as described above. Additionally, an MTT cell proliferation assay as described above was performed to calculate $EC_{50}$ values. Finally, a microphysiometer (Molecular Devices Corp.) assay was performed. Basically, in this assay the rate of acidification of the extracellular medium in response to TPO receptor stimulation by the compounds of the invention was determined. The ranges for $EC_{50}$ are symbolically indicated as for $IC_{50}$ described above. The results are summarized in Table 4.

TABLE 4

| Structure | EC50 (nM) Proliferation | EC50 (nM) Microphys. | IC50 (nM) | |
|---|---|---|---|---|
| {H}-{Pen}ADGPTLREWISF{Cys}-{NH₂} (S—S bridge) | + + | + + | + + | (SEQ ID NO: 172) |
| {O═C—NH}-ADGPTLREWISF{Cys}-{NH₂} (CH₂—S bridge) | + + | + + | + + | (SEQ ID NO: 173) |
| {H}-{Homocys}ADGPTLREWISF{Cys}-{NH₂} (S—S bridge) | + + | + + | ND | (SEQ ID NO: 174) |
| {O═C—N}-ADGPTLREWISF-{Cys}-{NH₂} (CH₂—S—O bridge) | + | + − | + − | (SEQ ID NO: 173) |
| {H}-{D-Cys}ADGPTLREWISF{D-Cys}-{NH2} (S—S bridge) | + | + − | ND | (SEQ ID NO: 175) |
| {H}-{Cys}ADGPTLREWISF{D-Cys}-{NH₂} (S—S bridge) | + − | + | + + | (SEQ ID NO: 176) |
| {H}-{D-Pen}ADGPTLREWISF{D-Cys}-{NH2} (S—S bridge) | + | + | + + | (SEQ ID NO: 177) |
| {H}-{Homocys}ADGPTLREWISF{Homocys}-{NH₂} (S—S bridge) | + | + | + + | (SEQ ID NO: 178) |
| {O═C—NH}-ADGPTLREWISF{Homocys}-{NH2} (CH₂—S bridge) | + | + | + + | (SEQ ID NO: 179) |
| {O═C—NH}-ADGPTLREWISF{Pen}-{NH₂} (CH₂—S bridge) | + | + − | + + | (SEQ ID NO: 180) |
| {O═C—NH}-ADGPTLREWISF{Cys}-{NH₂} (Ph—CH—S bridge) | + + | + − | + + | (SEQ ID NO: 173) |
| {H}-KADGPTLREWISFE-{NH₂} (NH—C═O bridge) | + | + − | ND | (SEQ ID NO: 181) |
| {H}-EADGPTLREWISFK-{NH₂} (O═C—NH bridge) | + | + | ND | (SEQ ID NO: 182) |
| {O═C—NH}-ADGPTLREWISF{Cys}-{NH₂} (alkyl—S bridge) | + + | + | ND | (SEQ ID NO: 173) |

TABLE 4-continued

| Structure | EC50 (nM) Proliferation | EC50 (nM) Microphys. | IC50 (nM) | |
|---|---|---|---|---|
| {O=C—NH}-ADGPTLREWISF{Cys}-{NH₂} (with S bridge) | + + | + − | ND | (SEQ ID NO: 173) |
| {HN}-ADGPTLREWISFE-{NH₂} (with C=O bridge) | + − | + − | + − | (SEQ ID NO: 183) |
| {H}-{Pen}ADGPTLREWISF{Pen}-{NH₂} (S—S bridge) | + − | + − | ND | (SEQ ID NO: 184) |

EXAMPLE 7

In this example amino acid substitutes at positions D, E, I, S, or F in the cyclized compound (SEQ ID NO:12)

CADGPTLREWISFC were assayed for $EC_{50}$ and $IC_{50}$ values as described above. Microphysiometer results are given in parentheses. The results are summarized in Table 5 below.

TABLE 5

CADGPILREWISFC (SEQ ID No: 12) [cyclized]

| Substitution | EC50 (nM) Cell Prolif. | IC50 (nM) |
|---|---|---|
| E - Q | + +(+) | + + |
| D - A | +(+) | + + |
| I - A | + −(+) | + |
| S - A | + +(+ +) | + + |
| S - D-Ala | + | + − |
| S - Sar | + − | + + |
| S - Aib | + +(+) | + + |
| S - D-Ser | + + | + + |
| S - Nva | + +(+ +) | + + |
| S - Abu | + + | + + |
| S - (N-Me-Ala) | + − | + |
| S - (N-Me-Val) | + | + − |
| S - (N-Me-Ala)* | + − | + − |
| S - (Nor-Leu) | + + | + + |
| S - (t-Bu-Gly) | + − | + + |
| S - [N-Me-Ser(Bzl)] | | + |
| S - (Homoser) | ND | ND |
| S - (N-Me-Leu) | + | ND |
| F - A | + −(+) | + + |
| F - D-Ala | + | + + |
| F - D-Phe | + | + + |
| F - Homo-Phe | + +(+ +) | + + |
| F - CHA | + +(+ +) | + + |
| F - Thi | + + | + + |
| F - (Ser(Bzl)) | + + | + + |
| F - (N-Me-Ala) | + − | + − |
| F - (Phenylgly) | + +(+ +) | + + |
| F - (Pyridylala) | + + | + + |
| F - (p-Nitrophe) | + +(+ +) | + + |
| F - (3,4-di-Cl-Phe) | + +(+) | + + |
| F - (p-Cl-Phe) | + + | + + |
| F - (2-Nal) | + +(+ +) | + + |
| F - (1-Nal) | + + | + + |
| F - (DiPh - Ala) | + + | + + |
| F - (N-Me-Phe) | + + | ND |
| S,F - Ava (thioether) | + − | + + |

TABLE 5-continued

CADGPILREWISFC (SEQ ID No: 12) [cyclized]

| Substitution | EC50 (nM) Cell Prolif. | IC50 (nM) |
|---|---|---|
| S,F - Ava (cys-cys) | + | + + |
| S,F - Ava | + − | + + |
| AD - deletion | + −(+) | ND |
| ADG - deletion | (+) | + |

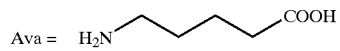
Ava = H₂N~~~COOH

EXAMPLE 8

In this example, amino acid substitutions in the compound (SEQ ID NO:173)

[O=C—NH]—ADGPTLREWISF (CYS)
   |                              |
   CH₂————————————————————S were evaluated at positions D, S, or F as indicated in Table 6 below $EC_{50}$ and $IC_{50}$ values were calculated as described above. Microphysiometer results are in parentheses.

TABLE 6

{O=C—NH}-ADGPTLREWISF{Cys} (SEQ ID NO: 173)
   |                              |
   CH2————————————————————S

| Substitution | EC50 (nM) Cell Prolif. | IC50 (nM) |
|---|---|---|
| D - E | (+) | ND |
| free acid form | + +(+) | ND |
| C-term, Gly addition | + + | + + |
| S - Abu | + +(+ +) | ND |
| F - DiPh-Ala | (+ +) | + + |
| S,F - Abu, DiPh-Ala | + −(+) | + + |

EXAMPLE 9

In this example $EC_{50}$ and $IC_{50}$ values were calculated as described above for the dimer compounds listed in Table 7 below. The cyclized monomer (SEQ ID NO:12)

CADGPTLREWISFC
|_____| is included as a comparison.

The compounds of Table 8 were inactive at the maximum concentration tested of 10 μm.

In Table 9, EC$_{50}$ and IC$_{50}$ values determined as described above for cyclized and dimerized variants of (SEQ ID NO:193) I E G P T L R Q W L A A R A are compared.

In Table 10, truncations of the dimer (SEQ ID NOS 17 & 18, respectively)

(H)—I E G P T L R Q W L A A R A (SEQ ID NO: 193)
                                    |
(H)—I E G P T L R Q W L A A R A (βala) K—(NH$_2$) (SEQ ID NO: 193)

are compared. EC$_{50}$ and IC$_{50}$ values were calculated as described above. Microphysiometer results are given in parentheses.

TABLE 7

| | EC50 (nM) | | | |
| --- | --- | --- | --- | --- |
| | Microphys. | Prolif. | IC50 (nM) | |
| {Br + C(=O)—NH}—ADGPTLREWISFC—{NH$_2$} | ++ | ++ | ++ | (SEQ ID NO: 173) |
| {Br + C(=O)—NH}-ADGPTLREWISFC-{NH$_2$} | | | | (SEQ ID NO: 173) |
| {H}-IEGPTLRQWLAARA<br>                         \|<br>{H}-IEGPTLRQWLAARA{β-Ala}K-{NH$_2$} | ++ | ++ | ++ | (SEQ ID NO: 17)<br>(SEQ ID NO: 18) |
| {H}-CIEGPTLRQWLAARA-{NH$_2$}<br>  \|<br>{H}-CIEGPTLRQWLAARA-{NH$_2$} | ++ | ++ | ++ | (SEQ ID NO: 185)<br>(SEQ ID NO: 185) |
| {H}-CADGPTLREWISF-{NH$_2$}<br>  \|<br>{H}-CADGPTLREWISF-{NH$_2$} | ++ | ++ | ++ | (SEQ ID NO: 186)<br>(SEQ ID NO: 186) |
| {H}-SVQCGPTLRQWLAARNHLS-{NH$_2$}<br>    \|<br>{H}-SVQCGPTLRQWLAARNHLS-{NH$_2$} | ++ | ++ | ++ | (SEQ ID NO: 187)<br>(SEQ ID NO: 187) |
| {H}-MVGPTLRSGC-{NH2}<br>         \|<br>{H}-MVGPTLRSGC-{NH2} | ND | + | +− | (SEQ ID NO: 188)<br>(SEQ ID NO: 188) |
| CADGPTLREWISFC<br>\|_____\| | ++ | ++ | ++ | (SEQ ID NO: 12) |
| {Ac}-ADGPTLREWISFC<br>             \|<br>{Ac}-ADGPTLREWISFC | ND | ++ | ++ | (SEQ ID NO: 173)<br>(SEQ ID NO: 173) |
| ADGPTLREWISFC<br>        \|<br>ADGPTLREWISFC | ++ | ++ | ++ | (SEQ ID NO: 173)<br>(SEQ ID NO: 173) |
| {Ac}-DGPTLREWISFC<br>           \|<br>{Ac}-DGPTLREWISFC | ++ | ++ | ++ | (SEQ ID NO: 189)<br>(SEQ ID NO: 189) |
| {Ac}-GPTLREWISFC<br>          \|<br>{Ac}-GPTLREWISFC | ND | ++ | ++ | (SEQ ID NO: 190)<br>(SEQ ID NO: 190) |
| GPTLREWISFC<br>      \|<br>GPTLREWISFC | ++ | ++ | + | (SEQ ID NO: 190)<br>(SEQ ID NO: 190) |
| {Ac}-PTLREWISFC<br>         \|<br>{Ac}-PTLREWISFC | ND | ++ | ++ | (SEQ ID NO: 191)<br>(SEQ ID NO: 191) |

TABLE 7-continued

| | EC50 (nM) | | | |
|---|---|---|---|---|
| | Microphys. | Prolif. | IC50 (nM) | |
| PTLREWISFC<br>\|<br>PTLREWISFC | + + | + + | + − | (SEQ ID NO: 191)<br>(SEQ ID NO: 191) |
| {Ac}-TLREWISFC<br>\|<br>{Ac}-TLREWISFC | + − | + − | + − | (SEQ ID NO: 192)<br>(SEQ ID NO: 192) |
| TLREWISFC<br>\|<br>TLREWISFC | + + | + − | + − | (SEQ ID NO: 192)<br>(SEQ ID NO: 192) |

TABLE 8

(SEQ ID NOS 205–222, respectively)

{H}-CTRAQFLKGC-{NH$_2$}

{H}-CNINQLRSIC-{NH$_2$}

{H}-CNRSQLLAAC-{NH$_2$}

{H}-CTSTQWLLAC-{NH$_2$}

{H}-CQRADLINFC-{NH$_2$}

{H}-CLLSEFLAGQQC-{NH$_2$}

{H}-CTFQVWKLARNC-{NH$_2$}

{H}-CTGQWLQMGMC-{NH$_2$}

{H}-CLTGPFVTQWLYEC-{NH$_2$}

TABLE 8-continued (SEQ ID NOS 205–222, respectively)

{H}-CTLREFLDPTTAVC-{NH$_2$}

{H}-CGTEGPTLSTWLDC-{NH$_2$}

{H}-CELVGPSLMSWLTC-{NH$_2$}

{H}-CSLKEFLHSGLMQC-{NH$_2$}

{H}-CTLAEFLASGVEQC-{NH$_2$}

{H}-CTLKEWLVSHEVWC-{NH$_2$}

{H}-CIEGPTLRQWLAARAC-{NH$_2$}    (SEQ ID NO. 194)

[H]—REGPTLRQWM—[NH$_2$]
[H]—REGPTLRQWLMSRS—[NH$_2$]

TABLE 9

| | EC50 (nM) | | | |
|---|---|---|---|---|
| | Microphys. | Prolif. | IC50 (nM) | |
| [H]—IEGPTLRQWLAARA—[NH$_2$] | N.D. | + + | + + | (SEQ ID NO: 193) |
| {H}-CIEGPTLRQWLAARAC-{NH$_2$} | N.D. | + + | + + | (SEQ ID NO: 194) |
| {H}-IEGPTLRQWLAARA<br>\|<br>{H}-IEGPTLRQWLAARA(β-Ala)K-{NH$_2$} | + + | + + | + + | (SEQ ID NO: 17)<br>(SEQ ID NO: 18) |
| {H}-CIEGPTLRQWLAARA-{NH$_2$}<br>\|<br>{H}-CIEGPTLRQWLAARA-{NH$_2$} | + + | + + | + + | (SEQ ID NO: 185)<br>(SEQ ID NO: 185) |

TABLE 10

{H}-IEGPTLRQWLAARA
|
{H}-IEGPTLRQWLAARA(β-Ala)K-{NH₂}  (SEQ ID NOS 17 & 18)

| Sequence | EC50 (nM) Cell Prolif. | IC50 (nM) |
|---|---|---|
| {Ac}-IEGPTLRQWLAARA<br>\|<br>{Ac}-IEGPTLRQWLAARA-βA-K{NH}  (SEQ ID NOS 17 & 18) | + + | ND |
| {H}-IEGPTLRQWLAAR<br>\|<br>{H}-IEGPTLRQWLAAR-βA-K{NH₂}  (SEQ ID NOS 195 & 196) | + + | ND |
| {H}-IEGPTLRQWLAA<br>\|<br>{H}-IEGPTLRQWLAA-βA-K{NH₂}  (SEQ ID NOS 197 & 198) | + +(+ +) | ND |
| {Ac}-EGPTLRQWLAARA<br>\|<br>{Ac}-EGPTLRQWLAARA-βA-K{NH₂}  (SEQ ID NOS 199 & 200) | ND | ND |
| {H}-EGPTLRQWLAARA<br>\|<br>{H}-EGPTLRQWLAARA-βA-K{NH₂}  (SEQ ID NOS 199 & 200) | + + | ND |
| {H}-EGPTLRQWLAAR<br>\|<br>{H}-EGPTLRQWLAAR-βA-K{NH₂}  (SEQ ID NOS 201 & 202) | + +(+ +) | ND |
| {Ac}-EGPTLRQWLAA<br>\|<br>{Ac}-EGPTLRQWLAA-βA-K{NH₂}  (SEQ ID NOS 203 & 204) | + + | ND |
| {H}-EGPTLRQWLAA<br>\|<br>{H}-EGPTLRQWLAA-βA-K{NH₂}  (SEQ ID NOS 203 & 204) | + + | ND |

EXAMPLE 10

In this example various substitutions were introduced at positions G, P, and W in the cyclized compound (SEQ ID NO:12)

Table 11 lists examples of the substituted compounds that show TPO agonist activity. The substitutions abbreviated in the table are as follows:

TABLE 11

[H] - C A D G P T L R E W I S F C - [NH₂]

| G | P | W |
|---|---|---|
| Sar | Hyp(OBn) | Nal |
| Sar | Hyp(OBn) | Nal |
| Gly | Pro | Trp |
| Gly | Pro | Trp |
| Sar | Hyp(OBn) | Nal |
| Gaba | Pro | Trp |
| Cpr—Gly | Pro | Trp |
| Sar | Hyp(OBn) | Nal |
| Gly | Pro | Trp |
| Gly | Pro | Nal |
| Sar | Pro | Trp |
| Cpr—Gly | L-Tic | Nal |
| Gly | D-Tic | D-Trp |

TABLE 11-continued

[H] - C A D G P T L R E W I S F C - [NH₂]

| G | P | W |
|---|---|---|
| Cpr—Gly | D-Tic | Trp |
| Gaba | Hyp(OBn) | Trp |

Proline Replacements

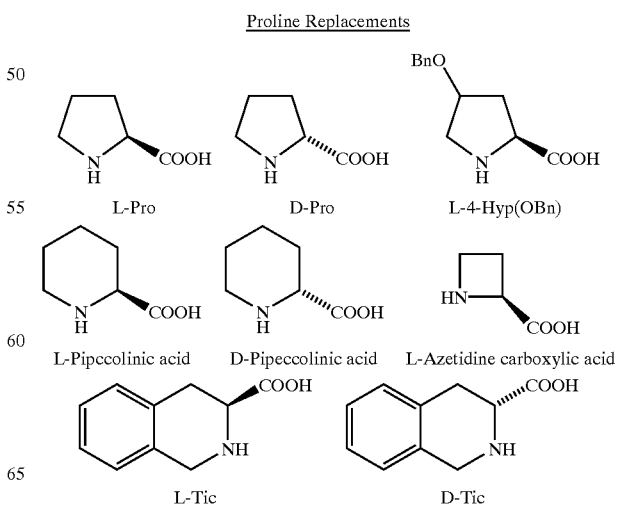

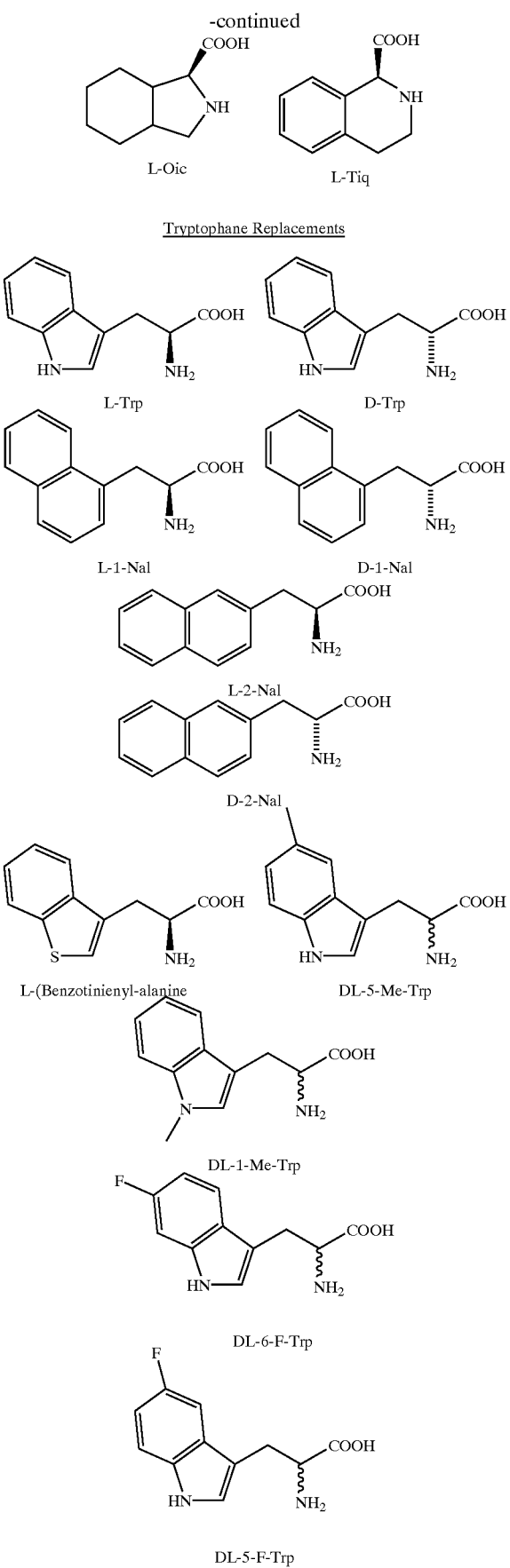

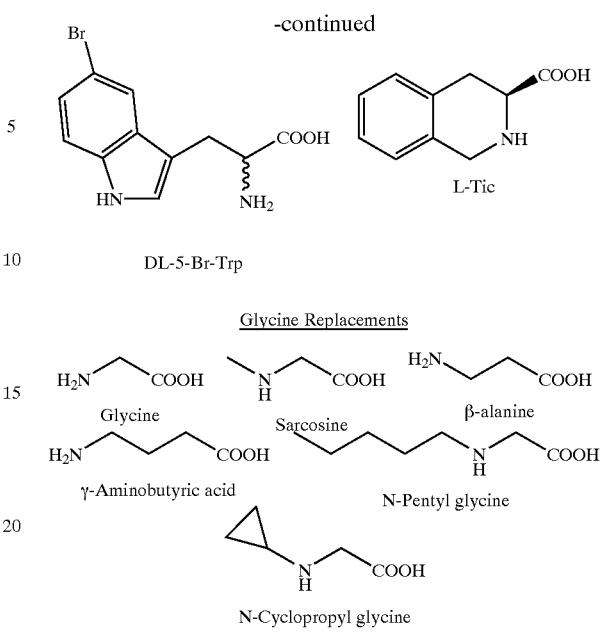

EXAMPLE 11

To assess the feasibility of mice as a convenient test species, several in vitro experiments, designed to measure the activity of the test compounds on the mouse receptor, have been done. First, marrow cells, harvested from the femurs of 8 to 9 week one Balb/C mice, were incubated for 7 days in liquid culture with either rhuTPO or various concentrations of the test peptides. At the end of the incubation period, the cultures were concentrated by Cytospin, stained for acetylcholinesterase (AChE, a diagnostic of mouse megakaryocytes), and counted by microscopic analysis. One (1) nM rhuTPO gave rise to the outgrowth of very large (>40 um) non-adherent cells that stain for ACHE. These cells appear to be mature megakaryocytes. From an initial seeding of $10^6$ total marrow cells/ml (in 50 ml cultures) an estimated 1 to $2 \times 10^6$ megakaryocytes developed. This responce to TPO was designated as "maximal". Control cultures containing no added growth factors produced very few AChE-positive cells. Several of the peptide compounds were tested at high concentration in this assay and the results are summarized in Table 12. Peptide A at 10 uM produced a maximal response of the mouse marrow. This finding was the first evidence that this peptide family is active on the murine receptor. In a second experiment, marrow cells were harvested and cultured in semi-solid medium (methylcellulose) containing either no factors, 1 nM rhuTPO, or 10 uM Peptide A. After 7 days in culture, colonies of large cell (presumed to be megakaryocytes) were counted and grouped into small colonies (3–5 cells) or large colonies (greater than 6 cells). The results are shown in Table 13. TPO and the test peptides both produced substantially more colonies of both sized than did the negative control cultures. This indicates that the peptides mimic TPO in their ability to stimulate the expansion of the Mk precursor cell population.

To obtain a more quantitative comparison of the activity of the test compounds on murine and human receptors, the muTPO receptor was cloned and transfected into BaF3 cells. A TPO dependent population of cells was isolated.

TABLE 12

| Peptide | Concentration Tested (nM) | Response |
|---|---|---|
| D | 100,000 | none |
| C | 40,000 | maximal** |
| C + S.A.* | 1000 | maximal** |
| S.A. alone | 1000 | none |
| B | 100,000 | minimul |
| A | 10,000 | maximal** |
| TPO (R & D) | 1 | "maximal" |

*Streptavidin complexed to biotinylated peptide — concentration of putative 1:4 complex.
**Compared to recombinant human TPO
**25–30% ACE staining cells on cytopspin
No factor cultures — ca. 5% AChE staining cells (lower cellularity)

TABLE 13

| Compound | | 3–5 large cells | 6–12 large cells |
|---|---|---|---|
| No factors | 1 | 2 | 1 |
| No factors | 2 | 1 | 1 |
| 1 nM TPO | #1-1 | 15 | 6 |
| 1 nM TPO | #1-2 | 12 | 1 |
| 1 nM TPO | #2-1 | 16 | 8 |
| 1 nM TPO | #2-2 | 13 | 3 |
| 10 uM Peptide | #1-1 | 25 | 10 |
| 10 uM Peptide | #1-2 | 22 | 8 |
| 10 uM Peptide | #2-1 | 22 | 7 |
| 10 uM Peptide | #2-2 | 21 | 10 |

The disclosures in this application of all articles and references, including patent documents, are incorporated herein by reference in their entirety for all purposes.

---

That which is claimed is:

1. A method of activating a thrombopoietin receptor in a cell, comprising contacting said cell with an effective amount of a peptide having a molecular weight of less than about 8000 daltons, and comprising a sequence of amino acids (SEQ ID NO:2):

$X_1 X_2 X_3 X_4 X_5 X_6 X_7$ where $X_1$ is C, L, M, P, Q, V; $X_2$ is F, K, L, N, Q, R, S, T or V; $X_3$ is C, F, I, L, M, R, S, V or W; $X_4$ is any of the 20 genetically coded L-amino acids; $X_5$ is A, D, E, G, K, M, Q, R, S, T, V or Y; $X_6$ is C, F, G, L, M, S, V, W or Y; and $X_7$ is C, G, I, K, L, M, N, R or V.

2. A method according to claim 1, wherein from zero to all of the —C(O)NH— linkages of the peptide have been replaced by a linkage selected from the group consisting of a —CH$_2$OC(O)NR— linkage; a phosphonate linkage; a —CH$_2$S(O)$_2$NR— linkage; a —CH$_2$NR— linkage; a —C(O)NR$^6$— linkage; and a —NHC(O)NH— linkage; and wherein R is hydrogen or lower alkyl and R$^6$ is lower alkyl, further wherein the N-terminus of said peptide is selected from the group consisting of a —NRR$^1$ group; a —NRC(O)R group; a —NRC(O)OR group; a —NRS(O)$_2$R group; a —NHC(O)NHR group; a succinimide group; a benzyloxycarbonyl-NH— group; and a benzyloxycarbonyl-NH— group having from 1 to 3 substituents on the phenyl ring selected from the group consisting of lower alkyl, lower alkoxy, chloro, and bromo;

and wherein R and R$^1$ are independently selected from the group consisting of hydrogen and lower alkyl, and still further wherein the C-terminus of said peptide has the formula —C(O)R$^2$ where R$^2$ is selected from the group consisting of hydroxy, lower alkoxy, and —NR$^3$R$^4$ where R$^3$ and R$^4$ are independently selected from the group consisting of hydrogen and lower alkyl and where the nitrogen atom of the —NR$^3$R$^4$ group can optionally be the amine group of the N-terminus of the peptide so as to form a cyclic peptide, and physiologically acceptable salts thereof.

3. the method of claim 1, wherein said peptide is cyclized.

4. The method of claim 1, wherein said peptide is dimerized.

5. The method of claim 1, wherein said peptide comprises a sequence of amino acids (SEQ ID NO:3):

X$_8$ G X$_1$ X$_2$ X$_3$ X$_4$ X$_5$ W X$_7$ where X$_1$ is L, M, P, Q, or V; X$_2$ is F, R, S, or T; X$_3$ is F, L, V, or W; X$_4$ is A, K, L, M, R, S, V, or T; X$_5$ is A, E, G, K, M, Q, R, S, or T; X$_7$ is C, I, K, L, M or V; and X$_8$ is any of the 20 genetically coded L-amino acids.

6. The method of claim 5, wherein X$_1$ is P; X$_2$ is T; X$_3$ is L; X$_4$ is R; X$_5$ is E or Q; X$_7$ is I or L (SEQ ID NO:4).

7. The method of claim 6, wherein said peptide comprises a sequence of amino acids (SEQ ID NO:5):

X$_9$ X$_8$ G X$_1$ X$_2$ X$_3$ X$_4$ X$_5$ W X$_7$ where X$_8$ is A, C, D, E, K, L, Q, R, S, T, or V; and X$_9$ is A, C, E, G, I, L, M, P, R, Q, S, T, or V.

8. The method of claim 7, wherein X$_8$ is D, E, or K; and X$_9$ is A or I.

9. The method of claim 8, wherein said amino acid sequence is selected from the group consisting of (SEQ ID NOs 6–13, respectively): G G C A D G P T L R E W I S F C G G; G N A D G P T L R Q W L E G R R P K N; G G C A D G P T L R E W I S F C G G K; T I K G P T L R Q W L K S R E H T S; S I E G P T L R E W L T S R T P H S; L A I E G P T L R Q W L H G N G R D T; C A D G P T L R E W I S F C; and I E G P T L R Q W L A A R A.

10. A method of activating a thrombopoietin receptor in a cell, comprising contacting said cell with an effective amount of a compound selected from the group consisting of

C A D G P T L R E W I S F C; (SEQ ID NO: 12)
|_____|

[Ac]—C A D G P T L R E W I S F C—[amide]; (SEQ ID NO: 12)
    |_____|

-continued

O=C A D G P T L R E W I S F C—NH$_2$; and (SEQ ID NO: 12)
 |                          |
 CH$_2$---------S I E G P T L R Q W L A A R A (SEQ ID NO: 17)
                         |
I E G P T L R Q W L A A R A (βala)—K [NH$_2$] (SEQ ID NO: 18)

11. A method according to claim 1 wherein said cells comprise human megakaryocytes or committed human megakaryocyte progenitor cells.

12. A method according to claim 10 wherein said cells comprise human megakaryocytes or committed human megakaryocyte progenitor cells.

13. A method according to claim 1 where said cells are in vitro.

14. A method according to claim 10 where said cells are in vitro.

15. A method of treating thrombocytopenia in a subject, comprising:

(a) obtaining a population of said subject's cells comprising megakaryocyte precursor cells;

(b) treating said cells in vitro according to the method of claim 1; and (c) administering said treated cells to said subject, to increase the number of megakaryocytes present in said subject compared to that which would occur without such treatment.

16. A method of treating thrombocytopenia in a subject, comprising:

(a) obtaining a population of said subject's cells comprising megakaryocyte precursor cells;

(b) treating said cells in vitro according to the method of claim 10; and (c) administering said treated cells to said subject, to increase the number of megakaryocytes present in said subject compared to that which would occur without such treatment.

17. A method of prophylactically treating a subject at risk of thrombocytopenia, comprising carrying out the method of claim 15 prior to development of thrombocytopenia.

18. A method according to claim 17 where said method is carried out prior to bone marrow transplantation, chemotherapy, or radiation therapy.

19. A method of prophylactically treating a subject at risk of thrombocytopenia, comprising carrying out the method of claim 16 prior to development of thrombocytopenia.

20. A method according to claim 19 where said method is carried out prior to bone marrow transplantation, chemotherapy, or radiation therapy.

* * * * *